(12) United States Patent
Rajasekaran

(10) Patent No.: US 12,152,279 B2
(45) Date of Patent: *Nov. 26, 2024

(54) PHOTOACTIVE COMPOUNDS AND METHODS FOR BIOMOLECULE DETECTION AND SEQUENCING

(71) Applicant: Vibrant Holdings LLC, San Carlos, CA (US)

(72) Inventor: John J. Rajasekaran, Hillsborough, CA (US)

(73) Assignee: Vibrant Holdings, LLC, Santa Clara, CA (US)

( * ) Notice: Subject to any disclaimer, the term of this patent is extended or adjusted under 35 U.S.C. 154(b) by 519 days.

This patent is subject to a terminal disclaimer.

(21) Appl. No.: 17/492,189

(22) Filed: Oct. 1, 2021

(65) Prior Publication Data

US 2022/0162698 A1 May 26, 2022

Related U.S. Application Data

(60) Continuation of application No. 16/709,423, filed on Dec. 10, 2019, which is a division of application No. 15/991,706, filed on May 29, 2018, now Pat. No. 10,538,808.

(60) Provisional application No. 62/511,786, filed on May 26, 2017.

(51) Int. Cl.
| | | |
|---|---|---|
| *C12Q 1/6876* | (2018.01) | |
| *C12Q 1/6837* | (2018.01) | |
| *C12Q 1/6874* | (2018.01) | |
| *C40B 30/04* | (2006.01) | |

(52) U.S. Cl.
CPC ......... *C12Q 1/6876* (2013.01); *C12Q 1/6837* (2013.01); *C12Q 1/6874* (2013.01); *C40B 30/04* (2013.01)

(58) Field of Classification Search
CPC .. C12Q 1/6876; C12Q 1/6837; C12Q 1/6874; C12Q 2523/319; C12Q 2527/119; C12Q 2535/101; C12Q 2565/607; C40B 30/04
See application file for complete search history.

(56) References Cited

U.S. PATENT DOCUMENTS

| | | | |
|---|---|---|---|
| 4,780,405 A | 10/1988 | Kaiser et al. | |
| 5,069,996 A | 12/1991 | Rogler | |
| 5,143,854 A | 9/1992 | Pinrung et al. | |
| 5,240,811 A | 8/1993 | Taylor et al. | |
| 5,310,687 A | 5/1994 | Bard et al. | |
| 5,866,434 A | 2/1999 | Massey et al. | |
| 5,919,523 A | 7/1999 | Sundberg et al. | |
| 5,945,286 A | 8/1999 | Krihak et al. | |
| 6,017,696 A | 1/2000 | Heller | |
| 6,040,138 A | 3/2000 | Lockhart et al. | |
| 6,083,697 A | 7/2000 | Beecher et al. | |
| 6,140,045 A | 10/2000 | Wohlstadter et al. | |
| 6,316,230 B1 | 11/2001 | Egholm et al. | |
| 6,319,726 B1 | 11/2001 | Schuppan et al. | |
| 6,359,125 B1 | 3/2002 | Kim et al. | |
| 6,395,474 B1 | 5/2002 | Buchardt et al. | |
| 6,469,151 B1 | 10/2002 | Egholm et al. | |
| 6,506,558 B1 | 1/2003 | Fodor et al. | |
| 6,521,181 B1 | 2/2003 | Northrup et al. | |
| 6,861,216 B2 | 3/2005 | Neriishi et al. | |
| 6,943,034 B1 | 9/2005 | Winkler et al. | |
| 6,969,766 B2 | 11/2005 | Kim et al. | |
| 7,022,851 B2 | 4/2006 | Kim et al. | |
| 7,041,453 B2 | 5/2006 | Yang | |
| 7,125,994 B2 | 10/2006 | Kim et al. | |
| 7,145,006 B2 | 12/2006 | Kim et al. | |
| 7,179,896 B2 | 2/2007 | Kim et al. | |
| 7,211,668 B2 | 5/2007 | Kim et al. | |
| 7,320,864 B2 | 1/2008 | Yang | |
| 7,476,504 B2 | 1/2009 | Turner | |
| 7,510,841 B2 | 3/2009 | Stuelpnagel et al. | |
| 7,527,912 B2 | 5/2009 | Ohsawa et al. | |
| 7,544,638 B2 | 6/2009 | Gao et al. | |
| 7,553,943 B2 | 6/2009 | Ellis et al. | |
| 7,608,397 B2 | 10/2009 | Densham | |
| 7,622,279 B2 | 11/2009 | Ju | |
| 7,659,064 B2 | 2/2010 | Park et al. | |
| 7,862,996 B2 | 1/2011 | Kuimelis et al. | |
| 7,956,011 B2 | 6/2011 | Serafinowski et al. | |
| 8,128,908 B2 | 3/2012 | Santra et al. | |
| 8,133,985 B2 | 3/2012 | Lee et al. | |
| 8,252,533 B2 | 8/2012 | Park et al. | |

(Continued)

FOREIGN PATENT DOCUMENTS

| | | |
|---|---|---|
| CN | 103234948 | 8/2013 |
| CN | 103675291 A | 3/2014 |

(Continued)

OTHER PUBLICATIONS

US 6,200,755 B1, 08/2006, Gordon et al. (withdrawn)

(Continued)

*Primary Examiner* — Narayan K Bhat

(74) *Attorney, Agent, or Firm* — Goodwin Procter LLP

(57) ABSTRACT

Disclosed herein are compositions, probes, devices, and processes useful for detecting specific reactions and binding interactions with biological molecules. In certain embodiments, methods of binding one or more biomolecules to a solid support are disclosed. Methods of generating site-specific sequences for one or more biomolecules from a solid support are also disclosed. Biological complexes generated by these methods are also disclosed.

29 Claims, 23 Drawing Sheets

Specification includes a Sequence Listing.

(56) References Cited

U.S. PATENT DOCUMENTS

| | | |
|---|---|---|
| 8,546,437 B2 | 10/2013 | Quart et al. |
| 8,969,002 B2 | 3/2015 | Esfandyarpour et al. |
| 9,216,399 B2 | 12/2015 | Rajasekaran et al. |
| 9,417,236 B2 | 8/2016 | Rajasekaran et al. |
| 9,631,231 B2 | 4/2017 | Shaffer et al. |
| 9,766,200 B2 | 9/2017 | Toumazou et al. |
| 10,006,909 B2 | 6/2018 | Rajasekaran et al. |
| 10,040,818 B2 | 8/2018 | Jayaraman |
| 10,316,363 B2 | 6/2019 | Ansari et al. |
| 10,538,808 B2 | 1/2020 | Rajasekaran |
| 2002/0076834 A1 | 6/2002 | Detlef et al. |
| 2002/0086319 A1 | 7/2002 | Ellson et al. |
| 2003/0068446 A1 | 4/2003 | Mirkin et al. |
| 2003/0082294 A1 | 5/2003 | Bruhn et al. |
| 2003/0124029 A1 | 7/2003 | Webb et al. |
| 2003/0148401 A1 | 8/2003 | Agrawal et al. |
| 2003/0228605 A1 | 12/2003 | Slootstra et al. |
| 2004/0027093 A1 | 2/2004 | Tashiro et al. |
| 2004/0038388 A1 | 2/2004 | Yamamoto et al. |
| 2004/0110133 A1 | 6/2004 | Xu et al. |
| 2005/0221351 A1 | 10/2005 | Ryu |
| 2005/0240811 A1 | 10/2005 | Safford et al. |
| 2005/0244863 A1 | 11/2005 | Mir |
| 2005/0260611 A1 | 11/2005 | Wang et al. |
| 2006/0088863 A1 | 4/2006 | Yamamoto et al. |
| 2006/0147949 A1 | 7/2006 | Ha et al. |
| 2006/0172340 A1 | 8/2006 | Wohlstadter et al. |
| 2007/0122841 A1 | 5/2007 | Rajasekaran et al. |
| 2007/0122842 A1 | 5/2007 | Rajasekaran et al. |
| 2007/0154946 A1 | 7/2007 | Rajasekaran et al. |
| 2007/0161778 A1 | 7/2007 | Kuimelis et al. |
| 2007/0231794 A1 | 10/2007 | Dill et al. |
| 2008/0108149 A1 | 5/2008 | Sundararajan et al. |
| 2009/0311727 A1 | 12/2009 | Watkins et al. |
| 2009/0325816 A1 | 12/2009 | Mirkin et al. |
| 2010/0028559 A1 | 2/2010 | Yan et al. |
| 2010/0093554 A1 | 4/2010 | Chu |
| 2010/0120630 A1 | 5/2010 | Huang et al. |
| 2010/0222547 A1 | 9/2010 | Rajagopalan et al. |
| 2010/0240555 A1 | 9/2010 | Sundararajan et al. |
| 2010/0245057 A1 | 9/2010 | Chamarti et al. |
| 2010/0304303 A1 | 12/2010 | Maeda et al. |
| 2011/0097762 A1 | 4/2011 | Gao et al. |
| 2011/0190210 A1 | 8/2011 | Adini et al. |
| 2011/0281766 A1 | 11/2011 | Cooper |
| 2011/0293644 A1 | 12/2011 | Anderson et al. |
| 2011/0303027 A1 | 12/2011 | Shirazi et al. |
| 2012/0172309 A1 | 7/2012 | Dal Farra et al. |
| 2012/0183981 A1 | 7/2012 | Norman et al. |
| 2012/0238477 A1 | 9/2012 | Albert et al. |
| 2012/0245057 A1 | 9/2012 | Albert et al. |
| 2013/0084532 A1 | 4/2013 | Wu et al. |
| 2014/0031239 A1 | 1/2014 | Kotsbak |
| 2014/0072963 A1 | 3/2014 | Qin |
| 2014/0073511 A1 | 3/2014 | Wong et al. |
| 2014/0349888 A1 | 11/2014 | Rajasekaran et al. |
| 2015/0038373 A1 | 2/2015 | Banyai et al. |
| 2015/0246336 A1 | 9/2015 | Somoza et al. |
| 2016/0009737 A1 | 1/2016 | Ikeda et al. |
| 2016/0144368 A1 | 5/2016 | Isami et al. |
| 2016/0186252 A1 | 6/2016 | Esfandyarpour et al. |
| 2016/0193608 A1 | 7/2016 | Isami et al. |
| 2017/0168047 A1 | 6/2017 | Aghvanyan et al. |
| 2017/0192007 A1 | 7/2017 | Rajasekaran et al. |
| 2018/0106795 A1 | 4/2018 | Rajasekaran et al. |
| 2018/0218250 A1 | 8/2018 | David et al. |
| 2019/0194745 A1 | 6/2019 | Rajasekaran |
| 2019/0217704 A1 | 7/2019 | Tschanz |
| 2019/0262794 A1 | 8/2019 | Rajasekaran |
| 2019/0366291 A1 | 12/2019 | Rajasekaran et al. |
| 2020/0095635 A1 | 3/2020 | Rajasekaran |
| 2021/0380629 A1 | 12/2021 | Rajasekaran et al. |

FOREIGN PATENT DOCUMENTS

| | | |
|---|---|---|
| EP | 1077264 A2 | 2/2001 |
| EP | 1517178 A1 | 3/2005 |
| EP | 0854937 B1 | 5/2005 |
| EP | 1198594 B1 | 5/2005 |
| EP | 1470114 B1 | 8/2009 |
| EP | 1651642 B1 | 11/2009 |
| EP | 1501812 B1 | 12/2009 |
| EP | 2174936 A1 | 4/2010 |
| EP | 1025120 B1 | 8/2010 |
| EP | 2003501 B1 | 10/2010 |
| EP | 2094863 B1 | 8/2014 |
| EP | 3790985 A1 | 3/2021 |
| JP | H05294995 A | 11/1993 |
| JP | H06500308 A | 1/1994 |
| JP | 2001503856 A | 3/2001 |
| JP | 2002500362 A | 1/2002 |
| JP | 2002502698 A | 1/2002 |
| JP | 2002520618 A | 7/2002 |
| JP | 2002525577 A | 8/2002 |
| JP | 2003517149 A | 5/2003 |
| JP | 2003523348 A | 8/2003 |
| JP | 2003524193 A | 8/2003 |
| JP | 2003342354 A | 12/2003 |
| JP | 2006519285 | 9/2004 |
| JP | 2004534226 A | 11/2004 |
| JP | 2005512032 A | 4/2005 |
| JP | 2005513999 A | 5/2005 |
| JP | 2005521032 A | 7/2005 |
| JP | 2005264156 A | 9/2005 |
| JP | 2005530983 A | 10/2005 |
| JP | 2006512893 A | 4/2006 |
| JP | 2006275152 A1 | 10/2006 |
| JP | 2007504946 A | 3/2007 |
| JP | 2008157952 A | 7/2008 |
| JP | 2008170449 A | 7/2008 |
| JP | 2009510786 A | 3/2009 |
| JP | 2009075131 A | 4/2009 |
| JP | 2009534200 A | 9/2009 |
| JP | 2010507099 A | 3/2010 |
| JP | 2010215816 A | 9/2010 |
| JP | 2011013118 A | 1/2011 |
| JP | 2011017711 A | 1/2011 |
| JP | 2011519168 A | 6/2011 |
| JP | 2011234723 A | 11/2011 |
| JP | 2012510431 A | 5/2012 |
| JP | 2012163491 A | 8/2012 |
| JP | 2012518294 A | 8/2012 |
| WO | 1994/28075 A1 | 12/1994 |
| WO | 98/03872 A2 | 1/1998 |
| WO | 98/12539 A1 | 3/1998 |
| WO | 1999/41007 A2 | 8/1999 |
| WO | 2000/16089 A1 | 3/2000 |
| WO | 2001/43870 A2 | 6/2001 |
| WO | 2003/001889 A2 | 1/2003 |
| WO | 2003/023360 A2 | 3/2003 |
| WO | 2003/038033 A2 | 5/2003 |
| WO | 2003/104273 A2 | 12/2003 |
| WO | 2004/027093 A1 | 4/2004 |
| WO | 2005/014696 A1 | 2/2005 |
| WO | 2007/038647 A2 | 4/2007 |
| WO | 2007/078868 A1 | 7/2007 |
| WO | 2008/097370 A2 | 8/2008 |
| WO | 2008/118167 A1 | 10/2008 |
| WO | 2008/151146 A2 | 12/2008 |
| WO | 2009/132321 A1 | 10/2009 |
| WO | 2010/060155 A1 | 6/2010 |
| WO | 2010/085763 A1 | 7/2010 |
| WO | 2010/096593 A2 | 8/2010 |
| WO | 2011/027048 A1 | 3/2011 |
| WO | 2011/034620 A2 | 3/2011 |
| WO | 2011/058136 A1 | 5/2011 |
| WO | 2012/122929 A1 | 9/2012 |
| WO | 2012/122959 A1 | 9/2012 |
| WO | 2012/154594 A1 | 11/2012 |
| WO | 2012/174479 A1 | 12/2012 |
| WO | 2013/119845 A1 | 8/2013 |
| WO | 2014/052989 A2 | 4/2014 |

(56) References Cited

FOREIGN PATENT DOCUMENTS

| WO | 2014/078606 A2 | 5/2014 |
|---|---|---|
| WO | 2014/127328 A2 | 8/2014 |
| WO | 2014/150851 A1 | 9/2014 |
| WO | 2015/016315 A1 | 2/2015 |
| WO | 2015/029691 A1 | 3/2015 |
| WO | 2015/127409 A1 | 8/2015 |
| WO | 2016145434 A1 | 9/2016 |
| WO | 2017/117292 A1 | 7/2017 |
| WO | 2018218250 | 11/2018 |
| WO | 2019217704 A1 | 11/2019 |

OTHER PUBLICATIONS

Zivic et al, Recent Advances and Challenges in the Design of Organic Photoacid and Photobase Generators for Polymerizations, 2019, Angew. Chem. Int. Ed. 2019, 58, 10410-10422. (Year: 2019).*
Nielsen, P. et al., "Sequence-Selective Recognition of DNA by Strand Displacement with a Thymine-Substituted Polyamide," Science, vol. 254, Iss. 5037, Dec. 6, 1991, pp. 1497-1500.
PCT/US2016/069017—International Search Report and Written Opinion, Apr. 21, 2017, 14 pages.
Seo et al., Four-color DNA sequencing by synthesis on a chip using photocleavable fluorescent nucleotides, 2005, PNAS, 102, 5926-5931.
Golubev, O. et al., "Formation of Mixed-Ligand Complexes of Pd2+ with Nucleoside 5'-Monophosphates and Some Metal-Ion-Binding Nucleoside Surrogates," Molecules, Oct. 22, 2014, vol. 19, No. 10, pp. 16976-16986.
PCT/US18/34939—International Search Report and Written Opinion, Nov. 15, 2018, 25 pages.
PCT/US18/34939—Invitation to Pay Additional Fees, Sep. 18, 2018, 2 pages.
Rothberg, J. et al., "An Integrated Semiconductor Device Enabling Non-Optical Genome Sequencing," Nature, vol. 475, Jul. 21, 2011, pp. 348-352.
Roy, B. et al., "Recent Trends in Nucleotide Synthesis," Chemical Reviews, 116(14), Jun. 20, 2016, pp. 7854-7897.
Shirai, M. et al., "Photoacid and Photobase Generators: Chemistry and Applications to Polymeric Materials," Progress in Polymer Science, vol. 21, Iss. 1, 1996, pp. 1-45.
Singh, Y. et al., "Recent Developments in Oligonucleotide Conjugation," Chemical Society Reviews, Iss. 6, Apr. 14, 2010, pp. 2054-2070.
Alawode, O. E. et al., "Clean Photodecomposition of 1-Methyl-4-Phenyl-1HTetrazole-5(4H)-Thiones to Carbodiimides Proceeds Via a Biradical," The Journal of Organic Chemistry, Jan. 7, 2011, pp. 216-222, vol. 76, No. 1.
Arimitsu K. et al., "Development of Highly Sensitive Photoreactive Materials Utilizing Photobase-generating Reactions and Base Proliferation Reactions", Journal Of Synthetic Organic Chemistry Japan, Jan. 1, 2012, pp. 508-516, vol. 70(5), Yuki Gosei Kagaku Kaokai, Tokyo, JP (with English Abstract).
Balakirev, M et al., "Photochemical Patterning of Biological Molecules Inside a Glass Capillary," Analytical Chemistry, vol. 77, No. 17, Sep. 1, 2005, pp. 5474-5479.
Ballew, J.T., "Antibody Biomarker Discovery Through in Vitro Directed Evolution of Consensus Recognition Epitopes," Proceedings of the National Academy of Sciences of the United States of America, Nov. 26, 2013, pp. 19330-19335, vol. 110, No. 48.
Beyer et al., "Combinatorial Synthesis of Peptide Arrays Onto a Microchip," Science, Dec. 21, 2007, p. 1888, vol. 318, 1 page and Sci. vol. 318 p. 1888 supporting online material, 6 pp.
Buus, S. et al., "High-Resolution Mapping of Linear Antibody Epitopes Using Ultrahigh-Density Peptide Microarrays," Molecular & Cellular Proteomics, Dec. 2012, pp. 1790-1800, vol. 11, No. 12.
Camarero, J., "Recent Developments in the Site-Specific Immobilization of Proteins Onto Solid Supports," Biopolymers, 2008, pp. 450-458, vol. 90, No. 3.
Carra, C. et al., "Proton-Coupled Electron Transfer in a Model for Tyrosine Oxidation in Photosystem II," Journal of the American Chemical Society, 2003, pp. 10429-10436, vol. 125.
Chen, "Solid-Phase Peptide Synthesis (SPPS) and Applications of Synthetic Peptides," Proteomics 2010, Jan. 2010, 63 pages [Online] [Retrieved on Sep. 16, 2015] Retrieved from the Internet<URL:http://bas.niu.edu.tw/download.php?filename=12155_cf09f16c.ppt&dir=communicty_forum/31&title=Topic+10-SPPS>.
Choung, R.S. et al., "Determination of B-Cell Epitopes in Patients with Celiac Disease: Peptide Microarrays," PLOS One, Jan. 29, 2016, e0147777, pp. 1-16, vol. 11, No. 1.
"Compound Summary for: CID 44140593, Tris(2,2'-bipyridine)ruthenium(II) dichloride," PubChem Compound, 2009 Retrieved from the Internet Jun. 29, 2014: <http://pubchem.ncbi.nlm.gov.summary/summary.cgi?cid=44140593&loc=ec res>.
Fathalla, E., et al., "Efficient Synthesis of 1-Substituted-4-phenyl-1, 4-dihydro-SH-tetrazole-5-thione and (1-Phenyl-1H-tetrazol-5-yl)thiozcetyl Derivatives," Heteroatom Chemistry, 2007, vol. 18, No. 6, pp. 637-643.
Fan et al., Polyglutamine (PolyQ) diseases genetics to treatments Cell Transplant 23: 441-458, 2014.
Gomez-Zavaglia, A., et al., "Molecular structure, vibrational spectra and photochemistry of 5-mercapto-1-methyltetrazole," Journal of Molecular Structure, 2006, vol. 786, pp. 182-192.
Gunda, N. et al., "Micro-Spot with Integrated Pillars (MSIP) for Detection of Dengue Virus NS1," Biomed Microdevices, vol. 15, 2013, pp. 959-971.
Gundagola, A.S.V., Synthesis, Photochemistry, and DNA Photocleavage of Compounds Containing Tetrazolethione Scaffolds, Kansas State University, 2011, 3 pages, [Online] [Retrieved on May 1, 2015] Retrieved from the Internet <URL: http://krex.kstate.edu/dspace/handle/2097/12022>.ex.kstate.edu/dspace/handle/2097/12022>, 2 pages.
Han, S-Y. et al., "Recent Development of Peptide Coupling Reagents in Organic Synthesis," Tetrahedron, 2004, pp. 2447-2467, vol. 60.
Lim, J-H. et al., "Direct-Write Dip-Pen Nanolithography of Proteins on Modified Silicon Oxide Surfaces," Angewandte Chemie International Edition, Wiley—VCH Verlag GmbH & Co., May 25, 2003, pp. 2309-2312, vol. 42, No. 20.
Lin et al., "Synthesis of Water Soluble Photoinitiators of Thioxanthone Derivatives III" Huadong Ligong Daxue Xuebao, Journal of East China University of Science and Technology, 2000, pp. 212-214, 220, vol. 26, No. 2 (with English abstract).
Meinl, E. et al., "Myelin Basic Protein-Specific T Lymphocyte Repertoire in Multiple Sclerosis, Complexity of the Response and Dominance of Nested Epitopes Due to Recruitment of Multiple T Cell Clones," The Journal of Clinical Investigation, Dec. 1993, pp. 2633-2643, vol. 92, No. 6.
Merrifield, R.B., "Solid Phase Peptide Synthesis. I. The Synthesis of a Tetrapeptide," J Am. Chem. Soc., Jul. 20, 1963, pp. 2149-2154, vol. 85, No. 14.
Pellois, J.P. et al., "Individually Addressable Parallel Peptide Synthesis on Microchips". Nature Biotechnology, Sep. 2002, pp. 922-926, vol. 20, No. 9.
Piehler, J. et al., "Protein Interactions in Covalently Attached Dextran Layers," Colloid and Surfaces B: Biointerfaces 13 (1999), pp. 325-336.
Resch-Genger et al., "Quantum Dots Versus Organic Dyes as Fluorescent Labels," Nature Methods, Sep. 2008, pp. 763-775, vol. 5, No. 9.
Sardesai, N.P. et al., "A Microfluidic Electrochemiluminescent Device for Detecting Cancer Biomarker Proteins," Anal. Bioanal. Chem. Epub Jan. 11, 2013, pp. 3831-3138, vol. 405, No. 11.
Shin, D-S. et al., "Automated Maskless Photolithography System for Peptide Microarray Synthesis on a Chip," J. Comb. Chem., 2010, pp. 463-471, vol. 12.
Sun, X. et al., "Bicyclic Guanidinium Tetraphenylborate: A Photobase Generator and a Photocatalyst for Living Anionic Ring-Opening Polymerization and Cross-Linking of Polymeric Materials Containing Ester and Hydroxy Groups," Journal of the American Chemical Society, Jul. 2008, pp. 8130-8131, vol. 130, No. 26.

(56) References Cited

OTHER PUBLICATIONS

Suyama K. et al., "Photobase Generators: Recent Progress and Application Trend in Polymer Systems", Progress In Polymer Science, Feb. 1, 2009, pp. 194-209, vol. 34(2), Pergamon Press, Oxford, GB.
Tapia, V. et al., "Evaluating the Coupling Efficiency of Phosphorylated Amino Acids for Spot Synthesis," J. Peptide Sci., 2008, pp. 1309-1314, vol. 14, No. 12.
Takahashi et al., Polyglutamne diseases: Where does toxicity come from? What is Toxicity? Where are we going? (J Mol Cell Biol 2: 180-191, 2010.
Thermofisher Scientific, "Molecular Probes™ Handbook: A Guide to Fluorescent Probes and Labeling Technologies," 11th edition, 2010, pp. 170-188.
Uddayasankar, U., "Towards a Surface Microarray Based Multiplexed Immunoassay on a Digital Microfluidics Platform," 2010, pp. 1-69, Master of Science Thesis. [Retrieved from the Internet Jun. 29, 2014: <https://cipweb.cardinal-ip.com/PCTSRS/PCTSRS DAT A/PCT-US%2014-16737/PRIOR_ART PCTPCTUS14-16737 Uddavasankar Master Thesis 2010.pdf>.
Wagner, "Quality Control for Peptide Chip Array Production," PHD Thesis, 2011, 140 pages, [Online] [Retrieved on Jun. 14, 2013] Retrieved from the Internet<URL:http://archiv.ub.uni-heidelberg.de/volltextserver/12602/1/report.pdf>.
Wang et al, Microfluidic DNA microarray analysis: A review, 2011, Analytica Chimica Acta, 687, 12-27.
Wei, H. et al., "Electrochemiluminescence of tris(2, 2'-bipyridyl)ruthenium and Its Applications in Bioanalysis: A Review," Luminescence, Mar.-Apr. 2011, pp. 77-85, vol. 26, Issue 2.
Young, J.D. et al., "Coupling Efficiencies of Amino Acids in the Solid Phase Synthesis of Peptides," Peptide Research, Jul. 1990, pp. 194-200, vol. 3, No. 4.
Yuan et al., "Integrated Tyramide and Polymerization-Assisted Signal Amplification for a Highly-Sensitive Immunoassay," Anal. Chem., 2012, pp. 10737-10744, vol. 84, No. 24.
Zhao, Y. et al., "A Fluorescent Amino Acid Probe to Monitor Efficiency of Peptide Conjugation to Glass Surfaces for High Density Microarrays," Mol. Biosyst., Epub Jan. 13, 2012, pp. 879-887, vol. 8, No. 3.
U.S. Appl. No. 15/977,951—Office Action, dated Aug. 30, 2019, 21 pages.
U.S. Appl. No. 14/941,404—Office Action, Dec. 11, 2018, 9 pages.
U.S. Appl. No. 15/120,452—Office Action, Sep. 18, 2017, 14 pages.
U.S. Appl. No. 16/019,449—Office Action, Apr. 29, 2019, 7 pages.
U.S. Appl. No. 16/287,968—Office Action, Jan. 6, 2020, 8 pages.
PCT/US18/34939—International Preliminary Report on Patentability, Dec. 5, 2019, 15 pages.
Uhlmann E., "Peptide nucleic acids (PNA) and PNA-DNA chimeras: from high binding affinity towards biological function", Biol Chem, 1998, vol. 379, No. 8-9, pp. 1045-1052.
PCT/US2019/031555—International Preliminary Report on Patentability, Nov. 19, 2020, 10 pages.
Ucar, Ultraviolet (UV) Radiation, Center for Science Education, 2017, 1-3. (Year: 2017).

* cited by examiner

Nucleic Acid Binding
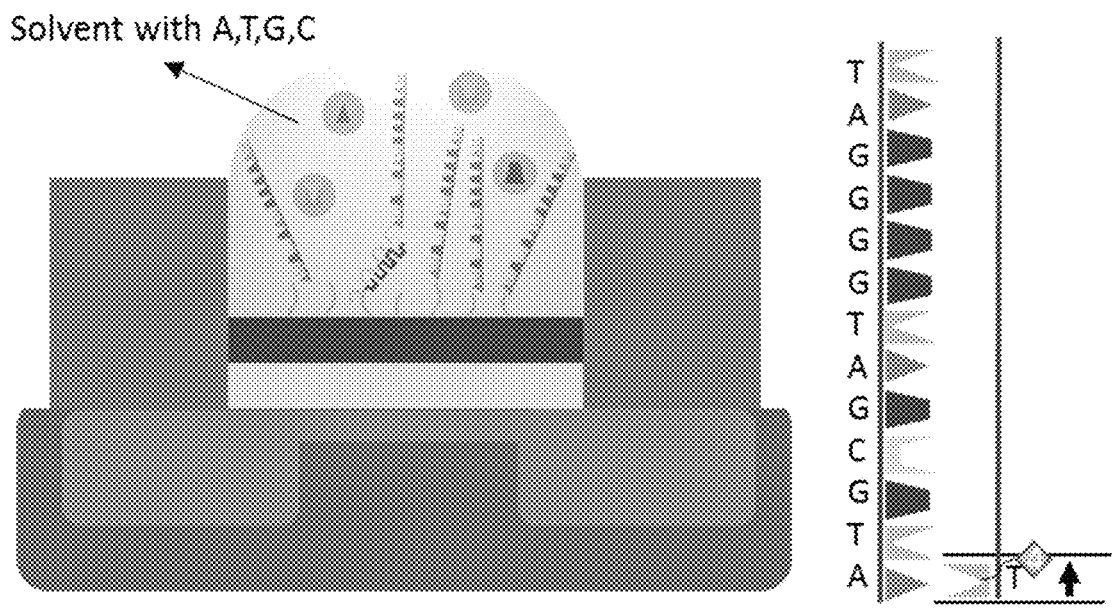
UV Light Exposure
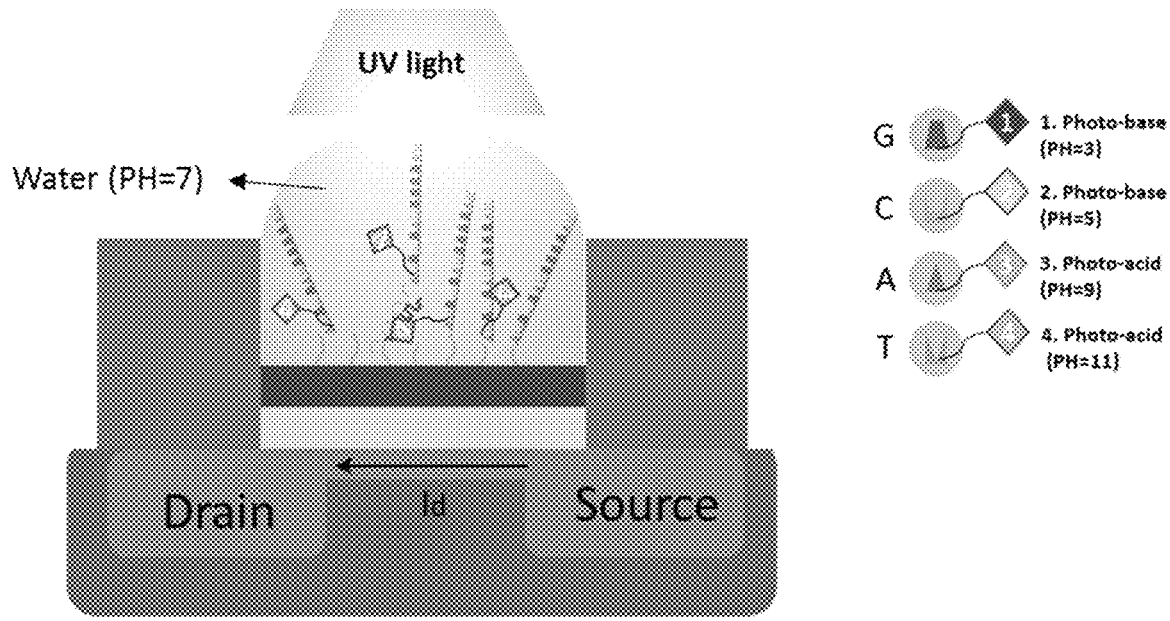
($pH$ change according to its binding nucleic acid. $\Delta pH \propto \Delta I_d$)
Figure 7

| Primer Extension | Sample | Call | ph Reading | | Primer Extension | Sample | Call | ph Reading | |
|---|---|---|---|---|---|---|---|---|---|
| | | | WT Adapter | MT Adapter | | | | WT Adapter | MT Adapter |
| PEM1 | Sample 1 | Homozygous Wild | 2.3 | 7.35 | PEM3 | Sample 1 | Homozygous Wild | 12.21 | 7.33 |
| | Sample 2 | Homozygous Wild | 2.36 | 7.4 | | Sample 2 | Homozygous Wild | 12.21 | 7.49 |
| | Sample 3 | Homozygous Wild | 2.41 | 7.41 | | Sample 3 | Homozygous Wild | 12.27 | 7.46 |
| | Sample 4 | Homozygous Wild | 2.49 | 7.34 | | Sample 4 | Homozygous Wild | 12.37 | 7.37 |
| | Sample 5 | Hetrozygous | 2.36 | 2.48 | | Sample 5 | Hetrozygous | 12.27 | 12.2 |
| | Sample 6 | Hetrozygous | 2.42 | 2.44 | | Sample 6 | Hetrozygous | 12.27 | 12.29 |
| | Sample 7 | Hetrozygous | 2.31 | 2.42 | | Sample 7 | Hetrozygous | 12.37 | 12.34 |
| | Sample 8 | Homozygous Mutant | 7.47 | 2.39 | | Sample 8 | Homozygous Mutant | 7.49 | 12.25 |
| | Sample 9 | Homozygous Mutant | 7.35 | 2.45 | | Sample 9 | Homozygous Mutant | 7.45 | 12.29 |
| | Sample 10 | Homozygous Mutant | 7.35 | 2.46 | | Sample 10 | Homozygous Mutant | 7.35 | 12.38 |
| PEM2 | Sample 1 | Homozygous Wild | 3.81 | 7.48 | PEM4 | Sample 1 | Homozygous Wild | 11 | 7.49 |
| | Sample 2 | Homozygous Wild | 3.86 | 7.42 | | Sample 2 | Homozygous Wild | 11.06 | 7.49 |
| | Sample 3 | Homozygous Wild | 3.9 | 7.39 | | Sample 3 | Homozygous Wild | 11.08 | 7.49 |
| | Sample 4 | Homozygous Wild | 3.73 | 7.3 | | Sample 4 | Homozygous Wild | 10.92 | 7.4 |
| | Sample 5 | Hetrozygous | 3.78 | 3.74 | | Sample 5 | Hetrozygous | 11.1 | 10.94 |
| | Sample 6 | Hetrozygous | 3.74 | 3.83 | | Sample 6 | Hetrozygous | 11.05 | 11.06 |
| | Sample 7 | Hetrozygous | 3.9 | 3.87 | | Sample 7 | Hetrozygous | 10.97 | 10.97 |
| | Sample 8 | Homozygous Mutant | 7.43 | 3.81 | | Sample 8 | Homozygous Mutant | 7.37 | 11.06 |
| | Sample 9 | Homozygous Mutant | 7.39 | 3.7 | | Sample 9 | Homozygous Mutant | 7.47 | 11.09 |
| | Sample 10 | Homozygous Mutant | 7.4 | 3.87 | | Sample 10 | Homozygous Mutant | 7.49 | 11.06 |

| Sample ID | Mutation | Original Result | pH Reading | HM Call | Calculated Result |
|---|---|---|---|---|---|
| MT1 | rs1801133 | Homozygous Wild C/C | 2.71 | HM5 | Homozygous Wild C/C |
| MT2 | rs1801133 | Homozygous Wild C/C | 2.75 | HM5 | Homozygous Wild C/C |
| MT3 | rs1801133 | Homozygous Wild C/C | 2.87 | HM5 | Homozygous Wild C/C |
| MT12 | rs1801133 | Heterozygous C/T | 6.84 | HM5, HM7 | Heterozygous C/T |
| MT13 | rs1801133 | Heterozygous C/T | 6.79 | HM5, HM7 | Heterozygous C/T |
| MT14 | rs1801133 | Heterozygous C/T | 6.855 | HM5, HM7 | Heterozygous C/T |
| MT15 | rs1801133 | Homozygous Mutant T/T | 11.04 | HM7 | Homozygous Mutant T/T |
| MT16 | rs1801133 | Homozygous Mutant T/T | 11.01 | HM7 | Homozygous Mutant T/T |
| MT17 | rs1801133 | Homozygous Mutant T/T | 11.12 | HM7 | Homozygous Mutant T/T |
| No Template | rs1801133 | No Template Control | 7.34 | None | No Template Control |

Figure 24A

| Sample ID | Mutation | Original Result | pH Reading | HM Call | Calculated Result |
|---|---|---|---|---|---|
| P91 | rs10757274 | Homozygous Wild A/A | 3.92 | HM6 | Homozygous Wild A/A |
| P92 | rs10757274 | Homozygous Wild A/A | 3.93 | HM6 | Homozygous Wild A/A |
| P93 | rs10757274 | Homozygous Wild A/A | 3.92 | HM6 | Homozygous Wild A/A |
| P912 | rs10757274 | Heterozygous A/G | 7.065 | HM6, HM8 | Heterozygous A/G |
| P913 | rs10757274 | Heterozygous A/G | 7.05 | HM6, HM8 | Heterozygous A/G |
| P914 | rs10757274 | Heterozygous A/G | 7.085 | HM6, HM8 | Heterozygous A/G |
| P915 | rs10757274 | Homozygous Mutant G/G | 10.11 | HM8 | Homozygous Mutant G/G |
| P916 | rs10757274 | Homozygous Mutant G/G | 10.1 | HM8 | Homozygous Mutant G/G |
| P917 | rs10757274 | Homozygous Mutant G/G | 10.24 | HM8 | Homozygous Mutant G/G |
| No Template | rs10757274 | No Template Control | 7.38 | None | No Template Control |

Figure 24B

SEQUENCE LISTING

<160> NUMBER OF SEQ ID NOS: 29

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggctagga aggtgtctgc gggagc                                          26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcgattgga aggtgtctgc gggagt                                          26

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

```
<400> SEQUENCE: 6

000

<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(31)
<223> OTHER INFORMATION: Peptide nucleic acid

<400> SEQUENCE: 7
gtggaaattt gacatagtct cagatgccta ttat                                   34

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aataataggc atctgagact atgtcaaatt tccac                                  35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cataataggc atctgagact atgtcaaatt tccac                                  35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gataataggc atctgagact atgtcaaatt tccac                                  35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tataataggc atctgagact atgtcaaatt tccac                                  35

<210> SEQ ID NO 12
<211> LENGTH: 41
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: Peptide nucleic acid

<400> SEQUENCE: 12
ggagaaggtg tctgcgggag ccgatttcat catcacgcag c                            41

<210> SEQ ID NO 13
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: Peptide nucleic acid

<400> SEQUENCE: 13
ggagaaggtg tctgcgggag tcgatttcat catcacgcag c                            41

<210> SEQ ID NO 14
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: Peptide nucleic acid

<400> SEQUENCE: 14
ggaggagctg accagtgaag aaagtgtctt tgaagtcttc g                            41

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(41)
<223> OTHER INFORMATION: Peptide nucleic acid

<400> SEQUENCE: 15
ggaggagctg accagtgaag caagtgtctt tgaagtcttc g                            41

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(31)
<223> OTHER INFORMATION: Peptide nucleic acid

<400> SEQUENCE: 16
ctgaagcact tgaaggagaa ggtgtctgcg ggag                                    34
```

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(31)
<223> OTHER INFORMATION: Peptide nucleic acid

<400> SEQUENCE: 17
ctgaagatgt gggggagga gctgaccagt gaag                                  34

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(16)
<223> OTHER INFORMATION: Peptide nucleic acid

<400> SEQUENCE: 18
atgcaccgac atgggc                                                     16

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(24)
<223> OTHER INFORMATION: Peptide nucleic acid

<400> SEQUENCE: 19
atgcaccgac atgggcatca cttg                                            24

<210> SEQ ID NO 20
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 atcacttg                                                               8

<210> SEQ ID NO 21
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 caagtgat                                                               8

```
<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cctattggca ggttacccca                                                  20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggcaagtgat gcccatgtcg                                                  20

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(30)
<223> OTHER INFORMATION: Peptide nucleic acid

<400> SEQUENCE: 24
ctcccccgtg ggtcaaatct aagctgagtg ttg                                   33

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Lys Trp Leu Asp Ser Phe Thr Glu Gln
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Lys Trp Leu Arg His Phe Thr Glu Gln
1               5                   10

<210> SEQ ID NO 27
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 27 tagggggtagc gta                                                          13

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
atacgattac                                                               10

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
taggtaatcg tat                                                           13
```

PHOTOACTIVE COMPOUNDS AND METHODS FOR BIOMOLECULE DETECTION AND SEQUENCING

CROSS-REFERENCE TO RELATED APPLICATIONS

This application is a continuation of U.S. application Ser. No. 16/709,423, filed Dec. 10, 2019, which application is a divisional of U.S. application Ser. No. 15/991,706, filed on May 29, 2018, which claims the benefit of U.S. Provisional Patent Application No. 62/511,786, filed May 26, 2017, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Jul. 27, 2018, is named 40697US_CFR_sequencelisting.txt and is 6,997 bytes in size.

BACKGROUND

Microarray technologies can facilitate detection of many features per square centimeter. This can include detection via probe binding methodologies to detect or accurately quantify the presence of biomolecules and to characterize these biomolecules, e.g., by determining a specific conformation or sequence. As more information continues to be processed at faster rates, certain features start to become problematic as limiting to the amount of information that can be obtained. For example, many detection technologies, such as probe detection and sequencing rely on monitoring fluorophores and distinguishing fluorophores bound to known probes. The use of fluorophore tags limits the size of the features on a chip due to the diffraction limit, and also can be difficult to detect at small concentrations. Alternative detection technologies exist, but they need further development to provide a suitable improvement to fluorophore-based detection technologies. Therefore, what are needed are alternatives to fluorophore-based detection technologies to improve detection accuracy and facilitate a reduction of feature size for higher throughput and more efficient detection.

As one example, a typical solid support-based detection assay is generally comprised of probes that bind to biologically relevant or active molecules for example, RNA, DNA, or peptides. Probes that bind to target molecules or the target molecules themselves can be covalently attached to a solid planar surface for example, glass, polymer (bead or even plastic composites), or most often, a silicon chip. Additionally, instruments are needed to handle samples (automated robotics), to read the reporter molecules (scanners) and analyze the data (bioinformatic tools). Recently, science has moved toward a unitary machine to perform these much need analyses. In order to marry the chemistry and biology with electronics, silicon wafers are most often used as the solid support or substrate. The term "lab on a chip" has since been coined to describe such an arrangement.

Microarrays technology can facilitate monitoring of many probes per square centimeter. The advantages of using multiple probes include, but are not limited to, speed, adaptability, comprehensiveness and the relatively cheaper cost of high volume manufacturing. The uses of such an array include, but are not limited to, diagnostic microbiology, including the detection and identification of pathogens, investigation of anti-microbial resistance, epidemiological strain typing, investigation of oncogenes, analysis of microbial infections using host genomic expression, and polymorphism profiles.

Recent advances in genomics have culminated in sequencing of entire genomes of several organisms, including humans. Genomics alone, however, cannot provide a complete understanding of cellular processes that are involved in disease, development, and other biological phenomena; because such processes are often directly mediated by polypeptides. Given that huge numbers of polypeptides are encoded by the genome of an organism, the development of high throughput technologies for analyzing polypeptides, amongst many other diverse biomolecules, is of paramount importance.

Peptide arrays with distinct analyte-detecting regions or probes can be assembled on a single substrate by techniques well known to one skilled in the art. A variety of methods are available for creating a peptide microarray. These methods include: (a) chemo selective immobilization methods; and (b) in situ parallel synthesis methods which can be further divided into (1) SPOT synthesis and (2) photolithographic synthesis. These methods are labor intensive and not suited for high throughput. These peptide arrays are expensive to manufacture, have low repeatability, may be unstable, require stringent storage conditions, take a long time to manufacture, and are limited in other ways. Further, while peptide-nucleic acid arrays are useful for identifying biomolecules, there is currently no way to deduce the binding strength or sequence.

What is needed therefore, are improved substrates or arrays and methods to elucidate and replicate biomolecule sequences and measure the binding of one or more biomolecules.

As another specific example, next generation sequencing technologies, including sequencing-by-synthesis, continue to pursue the goal of providing rapid sequencing data at a reasonable cost. This can be used to provide improved health care through individualized medicine and improved diagnostics. Despite many improvements in the past decades, this technology still has limitations in cost and throughput that prevent widespread use. Overcoming these limitations can provide a dramatic impact in several fields, including comparative genomics, high-throughput polymorphism detection, mutation screening, metagenomics, and transcriptome profiling.

Sequencing by synthesis of template DNA bound to a surface is commonly done using fluorophore-labeled, reversible terminator nucleotides. These nucleotides generate a signal corresponding to the sequence of a surface-bound template strand when incorporated into a complementary growing strand. For example, U.S. Pat. No. 7,622,279 teaches a fluorescence-based method for sequencing four modified nucleotides with photocleavable fluorescence molecules bound to the side chain of the four nucleic acid bases.

However, optical detection methods have a limited minimum feature size due to diffraction limited detection of fluorophores. Furthermore, imaging of an array of signals and processing the image to generate discrete endpoints can take time and be computationally demanding. Thus, alternative methods of nucleotide identity detection, such as electronic detection are also being explored.

One such method of electronic detection, Ion Sensitive Field Effect Transistors (ISFET), is able to detect small changes in the pH of a reaction volume. Non-optical genome sequencing using ISFET has been performed by adding a single nucleotide at a time to detect the release of an H+ ion upon incorporation of a correct base pair by a polymerase into a growing strand. However, this method is limited by the requirement of separate sequential addition of four individual nucleotides to determine the identity of the next nucleotide. Using ISFET detection, samples can be distributed on an array at the sub-micron level, and multiple arrays can be read simultaneously in a single device.

What is needed therefore, are improved methods, compositions, substrates and arrays for determining a polynucleotide sequence based on electronic detection to allow reduce feature size on an array for increased information density with output that allows for more efficient analysis.

Furthermore, arrays comprising primers or probes to bind to target sequences to allow sequencing are also needed to enable efficient binding of target polynucleotides for to an array for subsequent sequencing. Also needed are methods and compositions for manufacturing arrays comprising the probes.

SUMMARY

According to some embodiments, provided herein is a probe capable of binding specifically to a target biomolecule, wherein said probe is bound to a photoactive group. In some embodiments, the photoactive group is a photoacid generator or a photobase generator.

In some embodiments, the photobase generator produces an organic compound having a pKa of 9 or higher, 10 or higher, 11 or higher, 12 or higher, 13 or higher, or 14 or higher upon exposure to an activating radiation. In some embodiments, the photoacid generator produces an organic compound having a pKa of 5 or lower, 4 or lower, 3 or lower, 2 or lower, or 1 or lower upon exposure to an activating radiation.

In some embodiments, the photoacid generator is selected from the group consisting of: an o-acyloxime, a benzoyloxycarbonyl derivative, a photoactive carbamates, an oxime ester compounds, an ammonium compound, a benzoin compound, a dimethoxybenzyl urethane compound, an orthonitrobenzyl urethane compound, an aromatic sulfonamide, an alpha-lactams, and an N-(2-arylethenyl) amide. In some embodiments, the photoacid generator is selected from: the photoactive group of PM1 and the photoactive group of PM2.

In some embodiments, the photobase generator is selected from the group consisting of: a 2-hydroxy-2-phenylacetophenone N-cyclohexyl carbamate, an o-nitrobenzyl N-cyclohexyl carbamate, an N-cyclohexyl-2-naphthalene sulfonamide, a 3,5-dimethoxybenzyl N-cyclohexyl carbamate, an N-cyclohexyl p-toluene sulfonamide; and a dibenzoin isophorone dicarbamate. In some embodiments, the photobase generator is selected from the group consisting of: the photoactive group of PM3 and the photoactive group of PM4.

In some embodiments, the photoactive group is cleaved upon exposure to an activating radiation. In some embodiments, the cleavage is homolytic cleavage. In some embodiments, the photoactive group initiates a downstream reaction upon exposure to an activating radiation.

In some embodiments, the photoactive group comprises an ionic organic salt. In some embodiments, the photoactive group comprises an onium salt.

In some embodiments, the probe comprises a polypeptide. In some embodiments, the photoactive group is bound to said polypeptide. In some embodiments, the photoactive group is bound to a histidine side chain, a proline side chain, or a tyrosine side chain of said polypeptide.

In some embodiments, the probe is a polynucleotide or a single nucleotide. In some embodiments, the photoactive group is bound to a nucleobase of said polynucleotide or said single nucleotide. In some embodiments, the photoactive group is bound to a 2' or 5' carbon of said polynucleotide or said single nucleotide. In some embodiments, the single nucleotide comprises a removable blocking group. In some embodiments, the single nucleotide comprises a dideoxy terminator.

In some embodiments, the probe is selected from the group consisting of: a protein, a polypeptide, a glycoprotein, an oligosaccharide, and a glycolipid. In some embodiments, the probe is an antibody.

In some embodiments, provided herein is a composition comprising a nucleotide according to Formula I:

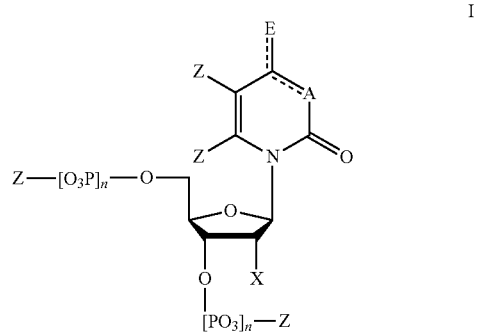

wherein n is from 0-3;

X is selected from the group consisting of: H, OPg, and a photoactive group, where Pg is a protecting group;

A is NH when

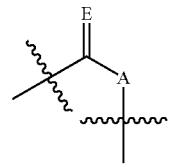

and A is N when

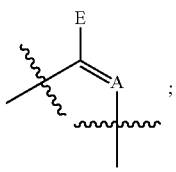

;

E is O when

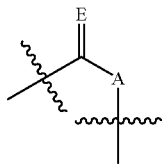

and E is NHZ when

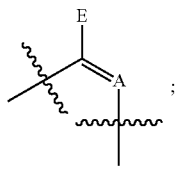

and
  each Z is independently selected from the group consisting of: H, Me, and a photoactive group;
  wherein at least one of said Z or X is said photoactive group.

In some embodiments, provided herein is a composition comprising a nucleotide according to Formula II:

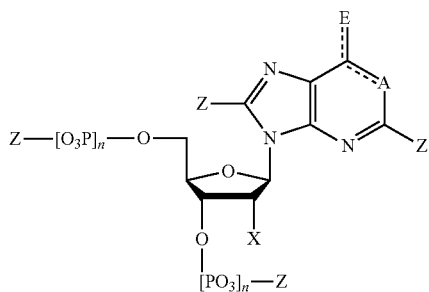

II wherein
n is from 0-3;
X is selected from the group consisting of: H, OPg, and a photoactive group, where
Pg is a protecting group;
A is NH when

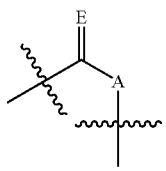

and A is N when

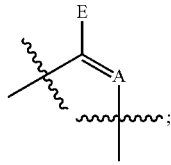

E is O when

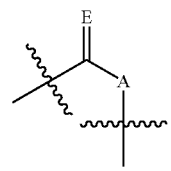

and E is NHZ when

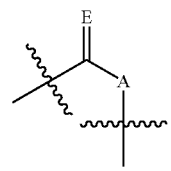

and
  each Z is independently selected from the group consisting of: H, Me, and a photoactive group;
  wherein at least one of said Z or X is said photoactive group.

Also provided herein, according to some embodiments, is a composition comprising a modified nucleotide comprising a photoacid or photobase generator.

Also provided herein, according to some embodiments, is a composition comprising a modified nucleotide selected from the group consisting of: PM1, PM2, PM3, PM4, PM5, PM6, PM7, and PM8.

In some embodiments, the modified nucleotide is bound to a removable blocking group. In some embodiments, the removable blocking group is a reversible terminator.

Also provided herein, according to some embodiments, is a polynucleotide comprising the modified nucleotide comprising a photoactive group provided herein.

Also provided herein, according to some embodiments, is an array comprising a one or more polynucleotides comprising the modified nucleotide comprising the photoactive group as provided herein, wherein the one or more polynucleotides are immobilized to the surface of the array. In some embodiments, the polynucleotide comprises PNA or LNA. In some embodiments, the array comprises a reaction area comprising said polynucleotide, wherein said reaction area comprises a set of electrodes for electronic monitoring of the pH of a solution. In some embodiments, the array comprises at least 100, at least 1,000, or at least 10,000 of said reaction areas.

Also provided herein, according to some embodiments, is a substrate comprising one or more compositions comprising the modified nucleotide comprising the photoactive group as provided herein, wherein the composition is immobilized to the surface of the substrate. In some embodiments, the substrate comprises an electrosensor capable of detecting a signal from said probe. In some embodiments, the electrosensor is an ion-sensitive field effect transistor.

Also provided herein, according to some embodiments, is an array of probes comprising the modified nucleotide comprising the photoactive group as provided herein.

Also provided herein, according to some embodiments, is a system an array of probes comprising the modified nucleotide comprising the photoactive group as provided herein, wherein said array is in electronic communication with a reader configured to receive an electronic signal from said set of electrodes.

Also provided herein, according to some embodiments, is a method for detecting a target biomolecule, comprising: providing probe capable of binding specifically to a target biomolecule, wherein said probe is bound to a photoacid generator or a photobase generator; contacting a sample suspected of comprising said target biomolecule with said probe; removing unbound probes from said sample; exposing said sample to an wavelength of light capable of activating said photoacid generator or said photobase generator, such that said probe, if bound to said target biomolecule, releases an acid or a base upon exposure to said wavelength of light; and detecting a concentration of ions in the sample, thereby identifying the presence or absence of said target analyte based on a change of said concentration of ions.

In some embodiments, the probe comprises a polynucleotide or a polypeptide. In some embodiments, the probe is an antibody.

In some embodiments, the concentration of ions is determined by measuring an ionic strength of the sample. In some embodiments, the ionic strength is measured using an ion-sensitive field effect transistor.

In some embodiments, the sample is immobilized on the surface of a substrate. In some embodiments, the substrate is an array. In some embodiments, the array comprises a plurality of wells, wherein said wells each comprise a sensor for detecting an ionic strength of a solution in said wells. In some embodiments, the sensor is an ion-sensitive field effect transistor.

Also provided herein, according to some embodiments, is a method of detecting a sequence identity of a target polynucleotide, comprising: providing a substrate comprising an immobilized target polynucleotide hybridized to a primer or probe; contacting said immobilized target polynucleotide with a solution comprising reagents for performing a polymerase extension reaction, said solution comprising a set of modified nucleotides comprising a photoactive group and a blocking group; exposing said substrate to conditions to promote incorporation of one of said modified nucleotides at the 3' end of said primer or probe; washing said substrate to remove unbound modified nucleotides; exposing said immobilized target polynucleotide to a wavelength of light to induce said photoactive group to generate an acid or a base, thereby generating a detectable change in ion concentration in a solution surrounding said immobilized target polynucleotide if said modified nucleotide is incorporated into said target polynucleotide; detecting said change in ion concentration; and determining a sequence identity of said target polynucleotide from said detected change in ion concentration.

Also provided herein, according to some embodiments, is a method of determining a sequence of a target polynucleotide, comprising: providing an array comprising a plurality of wells, wherein said wells comprise a target polynucleotide to be sequenced bound to a surface of said well, and wherein said plurality of wells each comprise a sensor for detecting an electronic signal from said wells; performing a sequencing reaction comprising performing at least one cycle, each cycle comprising: contacting said wells with a solution comprising reagents for performing a polymerase extension reaction, said solution comprising a set of modified nucleotides comprising a photoactive group and a removable blocking group; exposing said well to conditions to promote incorporation of one of said modified nucleotides at the 3' end of a primer or probe hybridized to said single polynucleotide; washing said well to remove unbound modified nucleotides; exposing said well to a wavelength of light to induce said photoactive group to generate and acid or a base, thereby generating a detectable change in ion concentration; detecting the change in ion concentration with said sensor; and if another cycle of the sequencing reaction is to be performed, removing said terminator from said incorporated nucleotide.

In some embodiments, the electronic signal is specific to the identity of the base of the modified nucleotide added to the primer at each cycle. In some embodiments, the electronic signal represents the pH of a solution in said well. In some embodiments, the electronic signal is analyzed to determine a sequence of the target polynucleotide. In some embodiments, the sensor is an ion-sensitive field effect transistor.

In some embodiments, the photoactive group is photocleavable. In some embodiments, the photoactive group is a photoacid or photobase generator. In some embodiments, the removable blocking group is a reversible terminator. In some embodiments, the reversible terminator is photocleavable.

In some embodiments, the nucleotide set comprises only one of the group consisting of: nucleotides comprising adenine, nucleotides comprising guanine, nucleotides comprising thymine, nucleotides comprising cytosine, and nucleotides comprising uracil.

In some embodiments, the nucleotide set comprises nucleotides comprising adenine, guanine, cytosine, and thymine or uracil. In some embodiments, the solution comprises a plurality of random primers. In some embodiments, the reagents for performing a polymerase extension reaction comprise a primer capable of hybridizing to said single polynucleotide.

In some embodiments, if another cycle is to be performed, the method further includes neutralizing the solution in the wells.

In some embodiments, the plurality of wells each comprise only a single target polynucleotide. In some embodiments, the plurality of wells each comprise a clonal population of a target polynucleotide.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 7 shows steps in a sequencing by synthesis reaction using the modified nucleotides comprising photobase or photoacid generators, according to an embodiment of the invention (SEQ ID NO: 27).

FIG. 18 shows a table of results of an assay to detect incorporation of each of the four modified nucleotides into a sequence.

FIGS. 24A and 24B show the results of detection of incorporation and identity of a single modified nucleotide (for each of PM5-PM8) for sequencing.

DETAILED DESCRIPTION

Figure 1:
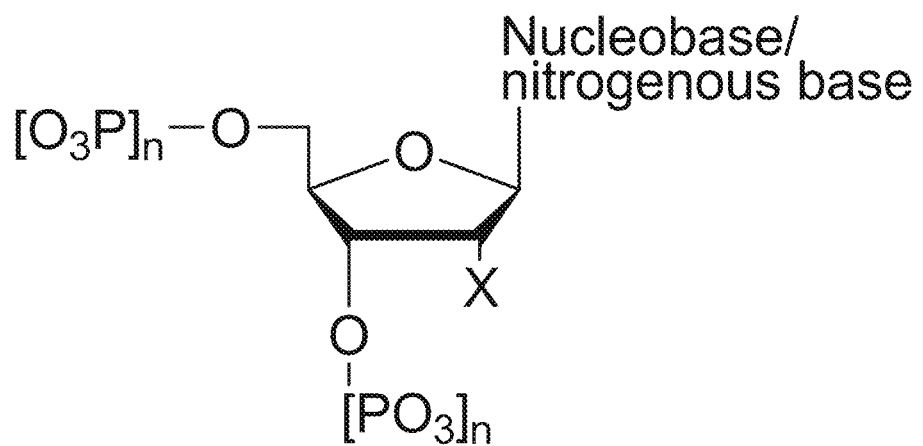
FIG. 1 shows a general structure of a modified nucleotide comprising a photoactive group at the 2' carbon, according to some embodiments.

The details of various embodiments of the invention are set forth in the description below. Other features, objects, and advantages of the invention will be apparent from the description and the drawings, and from the claims.

Definitions

Terms used in the claims and specification are defined as set forth below unless otherwise specified.

As used herein, the term "photoactive group" refers to a functional group that undergoes a lysis reaction when exposed to electromagnetic radiation, heat, or an initiator species, thereby generating an acid or a base. Compounds or functional groups that generate an acid when exposed to electromagnetic radiation within a spectrum of wavelength and/or energy are referred to herein as photoacid generators. Compounds or functional groups that generate an acid when exposed to electromagnetic radiation within a spectrum of wavelength and/or energy are referred to herein as photobase generators. As used herein, photoactive groups can be bound to probes, such as antibodies, polynucleotides, or incoming pairing nucleotides during sequence-directed polymerization such that the compounds can be specifically detected due to the generation of an acid or a base when exposed to an activating radiation.

As used herein, the terms "photoactive compound" or "photoactive molecule" refer to an organic compound or molecule comprising a photoactive group. In some embodiments, an organic compound comprising a photoactive functional group undergoes a lysis reaction upon exposure to radiation to generate an acid or a base. In some embodiments, the lysis reaction is a homolysis reaction. In some embodiments, a photoactive group or compound converts electromagnetic radiation into chemical energy and may need an initiator to start the photochemical or otherwise homolysis reaction, i.e. a compound is added to the composition that initiates homolysis by reacting with the electromagnetic radiation, or even heat, to form an intermediate initiating species, e.g., free radicals or cations, that react further with the photoactive group. The radical product from an initiator need not react directly, or next in sequence with a photoactive group. The initiating species may react with another compound in a chain reaction to produce the desired chemical reaction with a photoactive group.

Photoactive compounds or groups include, for example, cationic photoinitiators such as photoacid generators (PAGs) or photobase generators (PBGs), which generate a corresponding photoacid or photobase, respectively, when exposed to electromagnetic radiation. Examples of photoactive compounds are disclosed in the International Patent Publication No. WO/2014/078606, "Substrates, Systems, and Methods for Array Synthesis and Biomolecular Analysis," filed Nov. 14, 2013, which is incorporated herein in its entirety for all purposes. A photoinitiator is a compound especially added to a formulation to convert electromagnetic radiation into chemical energy in the form of initiating species, e.g., free radicals or cations. The acid, base, or other product of a photoactive compound exposed to electromagnetic radiation may then react with another compound in a chain reaction to produce a desired chemical reaction which can then be detected.

As used herein the terms "polypeptide," "peptide," or "protein" are used interchangeably to describe a chain or polymer of amino acids that are linked together by bonds. Accordingly, the term "peptide" as used herein includes a dipeptide, tripeptide, oligopeptide, and polypeptide. The term "peptide" is not limited to any particular number of amino acids. In some aspects, a peptide contains about 2 to about 50 amino acids, about 5 to about 40 amino acids, or about 5 to about 20 amino acids. A molecule, such as a protein or polypeptide, including an enzyme, can be a "native" or "wild-type" molecule, meaning that it occurs naturally in nature; or it may be a "mutant," "variant," "derivative," or "modification," meaning that it has been made, altered, derived, or is in some way different or changed from a native molecule or from another molecule such as a mutant.

As used herein the term "biomolecule" refers to any molecule(s) that occur naturally in a living organism. As such, the term biomolecules includes macromolecules such as, but certainly not limited to: proteins, carbohydrates, lipids and nucleic acids; and further also small molecules such as precursors and metabolites including, but not limited to: L-lysine, selenocysteine, isoprene, ATP and tocopherol.

As used herein, the term "probe molecules" refers to, but is not limited to, peptide nucleic acids ("PNA"), DNA binding sequences, oligonucleotides, nucleic acids, deoxyribonucleic acids (DNA), ribonucleic acids (RNA), nucleotide mimetics, chelates, side-chain modified peptide sequences, biomarkers and the like. As used herein, the term "feature" refers to a particular probe molecule that has been attached to a microarray. As used herein, the term "ligand" refers to a molecule, agent, analyte or compound of interest that can bind to one or more features.

As used herein the term "linker molecule" or "spacer molecule" includes any molecule that does not add any functionality to the resulting biomolecule but spaces and extends out the biomolecule from the substrate, thus increasing the distance between the substrate surface and the growing peptide, nucleic, or in general the growing biomolecule. This generally reduces steric hindrance with the substrate for reactions involving the biomolecule (including uni-molecular folding reactions and multi-molecular binding reactions) and so improves performance of assays measuring one or more aspects of functionality.

As used herein, the terms "immunological binding" and "immunological binding properties" refer to the non-covalent interactions of the type which occur between an immunoglobulin molecule and an antigen for which the immunoglobulin is a specific antibody/immunoglobulin molecule.

As used herein the term "antibody" or "immunoglobulin molecule" refers to a molecule naturally secreted by a particular type of cells of the immune system: B cells. There are five different, naturally occurring isotypes of antibodies, namely: IgA, IgM, IgG, IgD, and IgE.

The term "antigen" as used herein refers to a molecule that triggers an immune response by the immune system of a subject, e.g., the production of an antibody by the immune system. Antigens can be exogenous, endogenous or auto antigens. Exogenous antigens are those that have entered the body from outside through inhalation, ingestion or injection. Endogenous antigens are those that have been generated within previously-normal cells as a result of normal cell metabolism, or because of viral or intracellular bacterial infection. Auto antigens are those that are normal protein or protein complex present in the host body but can stimulate an immune response.

As used herein the term "epitope" or "immunoactive regions" refers to distinct molecular surface features of an antigen capable of being bound by component of the adaptive immune system, e.g., an antibody or T cell receptor. Antigenic molecules can present several surface features that can act as points of interaction for specific antibodies. Any such distinct molecular feature can constitute an epitope. Therefore, antigens have the potential to be bound by several distinct antibodies, each of which is specific to a particular epitope. biological sample As used herein, the term "wafer" refers to a slice of semiconductor material, such as a silicon or a germanium crystal generally used in the fabrication of integrated circuits. Wafers can be in a variety of sizes from, e.g., 25.4 mm (1 inch) to 300 mm (11.8 inches) along one dimension with thickness from, e.g., 275 µm to 775 µm.

As used herein the term "microarray," "array," or "chip" refers to a substrate on which different probe molecules of protein or specific DNA binding sequences have been affixed at separate locations in an ordered manner thus forming a microscopic array. In some embodiments, specific PNA, RNA or DNA binding sequences have been affixed at separate locations in an ordered manner thus forming a microscopic array. Specific PNA, RNA or DNA binding sequences may be bound to the substrate of the chip through one or more different types of linker molecules. A "chip array" refers to a plate having a plurality of chips, for example, 24, 96, or 384 chips.

As used herein the term "microarray system" refers to a system usually comprised of bio molecular probes formatted on a solid planar surface like glass, plastic or silicon chip plus the instruments needed to handle samples (automated robotics), to read the reporter molecules (scanners) and analyze the data (bioinformatic tools).

As used herein the terms "substrate" and "solid support" are used interchangeably and refer to any insoluble, polymeric material. Such materials must have rigid or semi-rigid surface, where examples include, but are not limited to, natural polymeric materials such as glass or collagen, and synthetic polymers such as acrylamide, polyvinyl chordae, or silicon based arrays.

As used herein, the term "PNA-DNA chimera" refers to an oligomer, or oligomers, comprised of: (i) a contiguous moiety of PNA monomer units and (ii) a contiguous moiety of nucleotide monomer units with an enzymatically-extendable terminus As used herein, the term "primer extension" refers to an enzymatic addition, i.e., polymerization, of monomeric nucleotide units to a primer while the primer is hybridized (annealed) to a template nucleic acid.

As used herein, the term "assay" refers to a type of biochemical test that measures the presence or concentration of a substance of interest in solutions that can contain a complex mixture of substances.

As used herein, the term "activating radiation" refers to electromagnetic radiation of a defined wavelength and energy sufficient to activate a photoactive group or compound to induce a reaction. In preferred embodiments, this reaction is the release of an acid or a base from a photoacid generator or a photobase generator, respectively.

As used herein, the term "blocking group" refers to a moiety bound to a monomer that prevents incorporation of a subsequent monomer in the synthesis of a polymer. A removable blocking group is one that can be removed to provide a binding site for incorporation of the next monomer. Removable blocking groups are commonly used for sequencing-by-synthesis reactions to control the stepwise addition of nucleotides during a template-directed polymerization reaction.

It must be noted that, as used in the specification and the appended claims, the singular forms "a," "an," and "the" include plural referents unless the context clearly dictates otherwise.

Overview

Described herein, according to some embodiments, are methods and compositions for sensitive and specific detection of target biomolecules immobilized to the surface of a substrate using probes tagged with photoactive compounds. As described herein, in some embodiments, the photoactive compounds are photoacid or photobase generators that generate a measureable change in the pH of the surrounding solution upon exposure to a wavelength of light. This change in pH is specific to the type of photobase or photoacid generator, such that multiple photoactive compounds can be distinguished. These probes comprising photoactive groups facilitate detection methods that provide a highly sensitive and specific detection that is not limited by the constraints of detection from light. In some embodiments, these methods are performed on an array of ISFET detectors to measure the change in pH of the solution surrounding bound probes comprising a photoactive group. Synthesis of several embodiments of probes bound to photoactive groups and the use of the same for detection of target biomolecules, including for sequence discrimination and sequence determination, is provided herein.

Photoactive Compounds

Disclosed herein are photoactive groups, i.e. photoactive organic molecules or functional groups. In a most general sense, photoactive groups or compounds are those which possess at least one chemical moiety that becomes reactive when exposed to radiation such as ultraviolet or visible light. Exposure of the photoactive compounds to electromagnetic radiation is a primary photochemical event that produces a change in the pH of the surrounding microenvironment. This change is brought about by the acidic or basic chemical species that is produced due to photoactivation of the photoactive group or compound. One or more photoactive group or compound may react by an elimination, addition, or rearrangement reaction; and may require an optional additive, or initiator, to kick-off the reaction reaction. In some embodiments, photoactivation generates a homolysis reaction to generate an acid or a base. In some embodiments, the photoactive groups or photoactive compounds are photoacid generators or photobase generators that directly generate an acid or a base upon photoactivation, e.g., from a homolysis reaction. In some embodiments, the photoactive groups or photoactive compounds are photoinitiators that indirectly release an acid or a base, e.g., through release of a chemical species that reacts downstream with another species to release an acid or a base.

Generally, the skilled artisan can easily identify a given functional group as a photoacid generator or a photobase generator since only those groups will form an organic acid or base possessing a proton or heteroatom that is recognizable as an acidic or basic group upon homolysis of the bond attaching that group to the compound. In this regard, the skilled artisan quickly recognizes a photoacid generator or a photobase generator by working backwards (in a sense) in identifying an acidic or basic functional group. For example, tertiary amine functional groups are recognized by organic chemists to be significantly basic because there is more electron density on the nitrogen atom of a tertiary amine, as opposed to say a secondary amine. Accordingly, a skilled artisan would recognize that any compound that has a quaternary amine functional group that will, upon homolysis, form a tertiary amine functional group, is a photoactive compound or functional group of the present disclosure.

In some embodiments, photoactive compounds or functional groups of the present disclosure will only include those which produce a compound having a pKa that is significantly acidic or basic so that one skilled in the art would recognize that a veritable organic acid or base would be generated. To this end, in some embodiments, photoactive compounds or functional groups of the present disclosure produce an organic compound that has a pKa of 10 or higher, 11 or higher, or 12 or higher. Photoactive compounds or functional groups of the present disclosure include acids or bases that are recognized in the art as "hard" or "soft".

In some aspects, photoactive compounds or functional groups of the present disclosure also have acidity or basicity according to the energy of their lowest unoccupied molecular orbital (LUMO) and/or energy of their highest unoccupied molecular orbital (HOMO). In some embodiments, the photoactive compounds or functional group produces a photoacid that has LUMO energy of −2.5 eV or lower (this is in terms of energy, so +1 would be lower). In some embodiments, the photoactive compounds or functional group produces a photobase that has HOMO energy of 1.7 eV or higher (this is in terms of energy, so −3 would be higher).

Photoactive compounds comprise at least one photoactive group to convert absorbed light energy, UV or visible light, into chemical energy in the form of initiating species, e.g., free radicals or cations. As such, in a general aspect, the photoactive groups or compounds of the present disclosure can be any organic functional group or compound that possesses one or groups that will absorb energy anywhere from 200 nm to 700 nm.

In general, photoactive compounds or functional groups are known to one skilled in the art. Examples of photoactive compounds or functional groups that are photoacid generators (PAG) include, but in no way are limited to: sulfonium salts, iodonium salts, sulfonyldiazomethane, N-sulfonyloxyimide, benzoinsulfonate, nitrobenzylsulfonate, sulfone, glyoxime derivatives, halogenated triazines, onium salts such as aryldiazonium salts and diaryl halonium salts, triaryl sulfonic salts, sulfonated esters, substituted hydroxyimides, substituted hydroxylimines, azides, naphthoquinones such as diazonaphthoquinones, diazo compounds, and many combinations thereof, nitrobenzyl esters, sulfones, phosphates, and the like. Examples of photoactive compounds or functional groups that are photobase generators (PBG) include, but in no way are limited to: o-acyloximes, benzoyloxycarbonyl derivatives, photoactive carbamates such as benzyl carbamates and benzoin carbamates, oxime ester compounds like o-carbamoyloximes, ammonium compounds like quaternary ammonium tetraphenyl borate salts, benzoin compounds, dimethoxybenzyl urethane compounds, orthonitrobenzyl urethane compounds, aromatic sulfonamides, alpha-lactams, N-(2-arylethenyl) amides, mixtures thereof, and the like. These compounds generally generate amine bases after irradiation. Photobase generators can also generate ammonia or hydroxy ions due to the action of light may also be used. These can be selected from, for example, N-substituted 4-(o-nitrophenyl)dihydroxypyridines, N-(2-nitrobenzyloxycarbonyl)piperidine, 1,3-bis(N-(2-nitrobenzyloxycarbonyl)-4-piperidyl]propane, N,N'-bis(2-nitrobenzyloxycarbonyl)dihexylamine, and O-benzylcarbonyl-N-(1-phenylethylidene)hydroxylamine. A good review of photoacid and photobase generators is found, for example, in Prog. Polym. Sci. vol. 21, 1-45, 1996, the entire contents and disclosure of which is incorporated herein by reference. Very specific examples of a suitable photobase generators include, but are not limited to: 2-hydroxy-2-phenylacetophenone N-cyclohexyl carbamate (i.e., $C_6H_5C(=O)CH(C_6H_5)OC(=O)NHC_6H_{11}$); o-nitrobenzyl N-cyclohexyl carbamate (i.e., $o-NO_2C_6H_5CH_2C(=O)NHC_6H_{11}$); N-cyclohexyl-2-naphthalene sulfonamide (i.e., $C_{10}H_7SO_2NHC_6H_{11}$); 3,5-dimethoxybenzyl N-cyclohexyl carbamate (i.e., $(CH_3O)_2C_6H_5CH_2C(=O)NHC_6H_{11}$); N-cyclohexyl p-toluene sulfonamide (i.e., $p-CH_3C_6H_5SO_2NHC_6H_{11}$); and dibenzoin isophorone dicarbamate. Finally, photoactive compound or functional group also includes any compounds or functional groups that behave as both photobases and photoacids. These compounds are described in the art as single component photoacid/photobase generators.

In some embodiments, a photoactive compound or group can be a photoacid generator (PAG) or a photobase generator (PBG). Photoacid generators (or PAGs) are cationic photoinitiators. A photoinitiator is a compound especially added to a formulation to convert absorbed light energy, UV or visible light, into chemical energy in the form of initiating species, e.g., free radicals or cations. Cationic photoinitiators are used extensively in optical lithography. The ability of some types of cationic photo initiators to serve as latent photochemical sources of very strong protonic or Lewis acids is generally the basis for their use in photo imaging applications.

In some embodiments, a photoacid generator is an iodonium salt, a polonium salt, or a sulfonium salt. In some embodiments, a photoacid generator is (4-Methoxyphenyl) phenyliodonium or trifluoromethanesulfonate. In some embodiments, a photoacid generator is (2,4-dihydroxyphenyl)dimethylsulfonium triflate or (4 methoxyphenyl)dimethylsulfonium triflate, shown below:

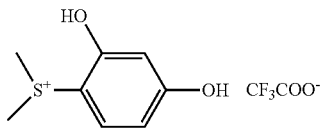

In some embodiments, a photoacid generator is iodonium and sulfonium salts of triflates, phosphates and/or antimonates.

In some embodiments, a photobase generator is 1,3-Bis [(2-nitrobenzyl)oxycarbonyl-4-piperidyl]propane or 1,3-Bis [(1-(9-fluorenylmethoxycarbonyl)-4-piperidyl]propane.

Conjugation of Photoactive Groups to Compounds

Generally the methods used to conjugate one or more photoactive molecule(s) or functional group(s) are known in the art. The skilled artisan will appreciate that various types of carbon-carbon and carbon-heteroatom bonds can be made that will attach a given photoactive molecule or functional group to any such biomolecule of interest. Of course the skilled artisan will appreciate that any such attachment must not interfere with the binding, enzymatic and/or biological function of one or more biomolecule(s) described herein, i.e. the activity of the biomolecule it is attached to must not be rendered inoperative nor shall the activity be rendered inoperative of other biomolecules such as DNA polymerase and the like that are otherwise present. To this end, one skilled in the art can refer to texts.

Further, once the photoactive compounds are synthesized, the task of conjugating these compounds onto either the nitrogenous base, saccharide residue, or phosphate is within the purview of one skilled in the art of organic synthesis. There is much literature and even whole texts that are now that review and are able to instruct an organic chemist how to perform the synthetic methods needed for "conjugating" a small organic molecule to an activated position on a biomolecule or even incorporating a "conjugated" or "tagged" (fluorescent or otherwise) molecule into a biological process, such as enzymatic bond cleavage or construction. Such synthetic methods nowadays are routine to the trained organic or medicinal chemist. Relevant review articles, texts, and books include, but are not limited to: Hermanson, G. T., Bioconjugate Techniques, 3$^{rd}$ Ed., Academic Press, Oxford (2013); Sinh, Y. et al., "Recent developments in oligonucleotide conjugation" Chem. Soc. Rev., 2010, 39, 2054-2070; and Roy, B. et al., "Recent Trends in Nucleotide Synthesis" Chem. Rev., 2016, 116 (14), pp 7854-7897.

As a general guide, herein disclosed are representative syntheses to attach a photoactive molecule or functional group to a given biomolecule. As such, these synthetic techniques may not cover each and every way to conjugate a photoactive molecule and thus, are not meant to be limiting in any form since the skilled artisan will be able to use alternative synthetic reactions to conjugate or otherwise insert a photoactive molecule or functional group to a given biomolecule onto a biomolecule.

Photoactive Nucleotides

In some embodiments, the photoactive group is covalently or non-covalently attached to one or more nucleotides, or any combination thereof. In some embodiments, the photoactive group is covalently in a selective manner. For example, the photoactive group may be covalently attached to a guanine nucleobase/nucleotide, but not any other nucleobases/nucleotides. In another example, the photoactive group may be covalently attached to a thymine nucleobase/nucleotide, but not any other nucleobases/nucleotides. In another example, the photoactive group may be covalently attached to any combination of two (2) of: cytosine, guanine, adenine, thymine and uracil (C, G, A, T, and U, respectively) nucleobases/nucleotides, but not any other nucleobases/nucleotides. In another example, the photoactive group may be covalently attached to any combination of three (3) of: cytosine, guanine, adenine, thymine and uracil (C, G, A, T, and U, respectively) nucleobases/nucleotides, but not any other nucleobases/nucleotides. In another example, the photoactive group may be covalently attached to any combination of four (4) of: cytosine, guanine, adenine, thymine and uracil (C, G, A, T, and U, respectively) nucleobases/nucleotides, but not any other nucleobases/nucleotides.

In one embodiment, nucleotides of the present disclosure are tagged with a photoactive group. In one embodiment nucleotides of the present disclosure have a general structure according to FIG. 1. The photoactive group can be bound to the sugar, i.e., at the 2' C position. The photoactive group can also be bound to the nucleobase in a way that does not interfere with hydrogen bonding to its cognate nucleobase.

Figure 2:
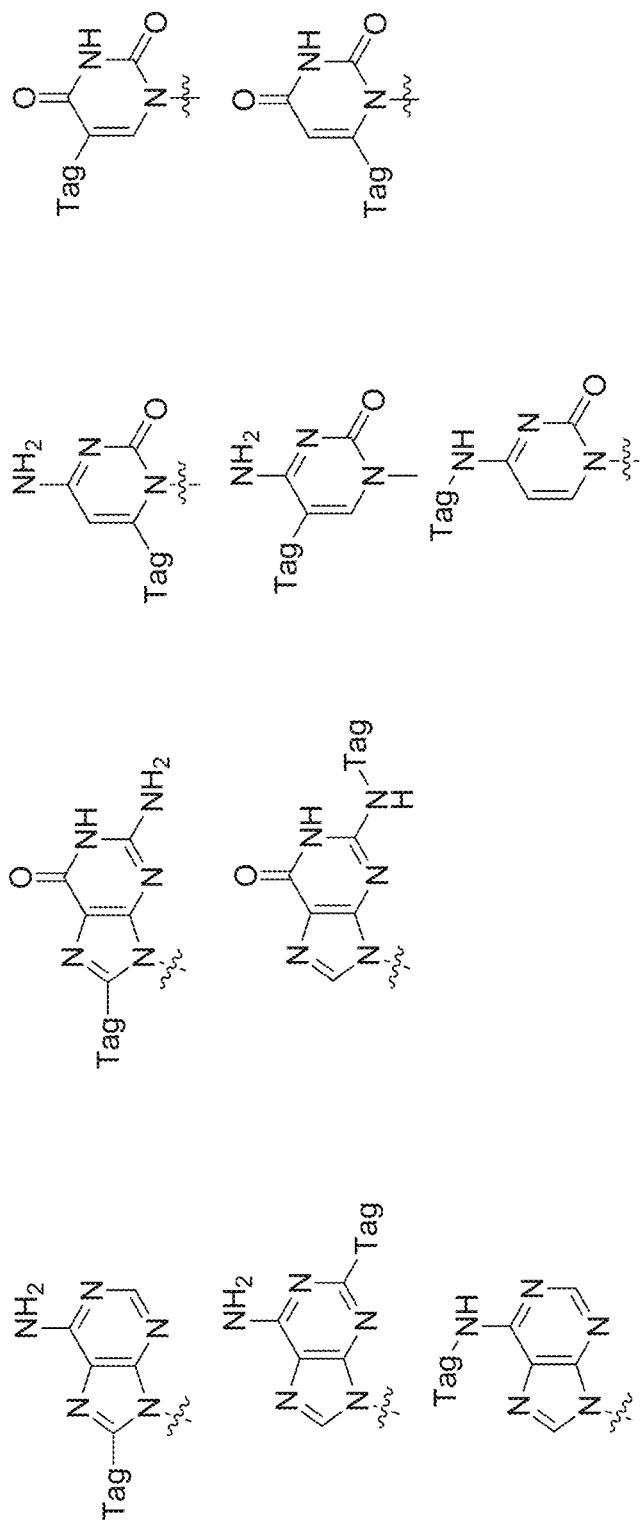
FIG. 2 shows embodiments of covalently bound attachment points of photoactive groups to different nucleobases to make a modified nucleotide.

In a general embodiment, the photoactive group is covalently attached to a nucleobase to make a modified nucleotide. In such an embodiment, the photoactive group may even be attached at a nitrogen atom of a nucleobase. Though it is preferable that the modification retain the biologically activity of the nucleotide, for example an enzyme such DNA polymerase I would still be capable of using the tagged nucleotide to create one or more complimentary strands of RNA or DNA or the like. In such embodiments, the tag, i.e. the photoactive group, may generally be covalently attached to the nucleobase according to the FIG. 2.

Figure 3:
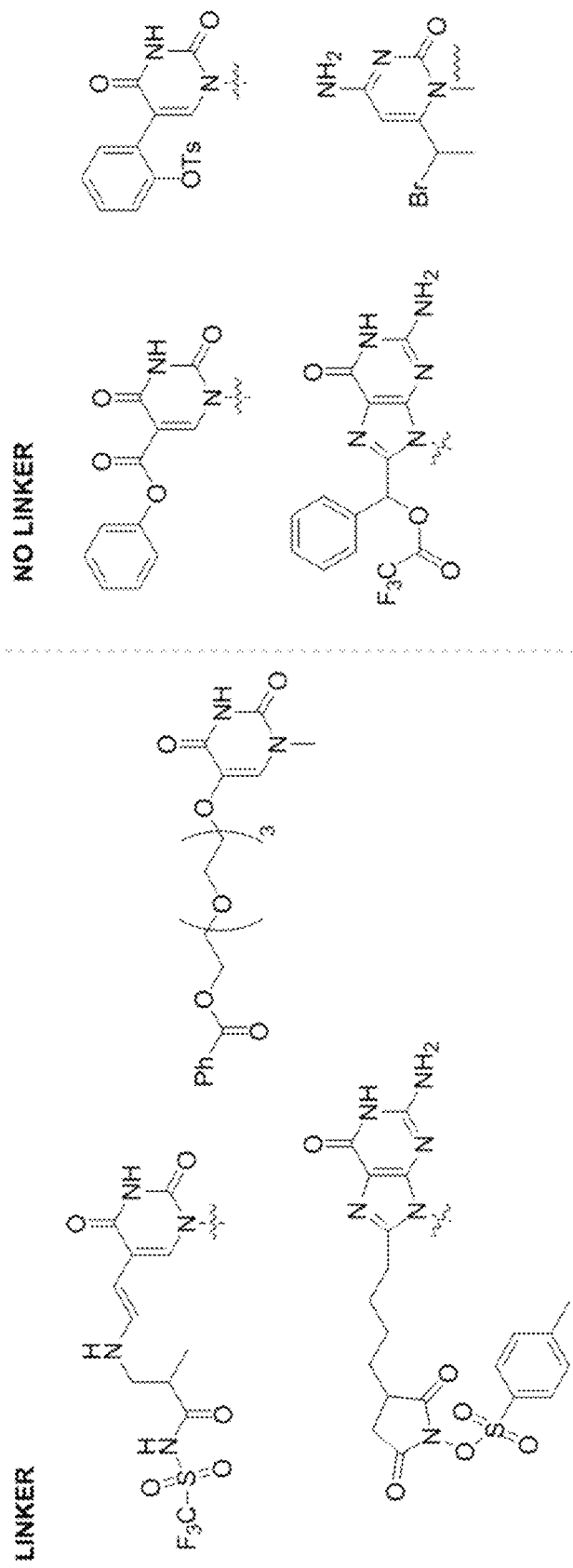
FIG. 3 shows examples of photoactive groups bound to a nucleobase with or without a linker.

In some embodiments, the photoactive group is covalently attached to a nucleobase via a linker. The linker can be from 2-40 atoms in length and need not be restricted in terms of the identity of heteroatoms and carbon atoms that it comprises. More to this point, the identity of the particular organic functional groups that comprise the linker is not crucial or limiting as long as one or more of the functional groups themselves are photoactive groups and do not react with other functional groups of the nucleotide(s) or other components in the system so as to render them inoperable, e.g. peptide side chain functional groups are not altered so as to impact a loss in biological activity or even an enzyme, present in the system/assay, perhaps DNA polymerase I is not affected so as its function is impaired. Additionally in some embodiments, the photoactive group is covalently attached to a nucleobase directly and without any functional group as a linker. Examples of these photoactive group tags covalently bonded to a nucleobase are shown in FIG. 3 and are not meant to be limiting in any way.

Figure 4:
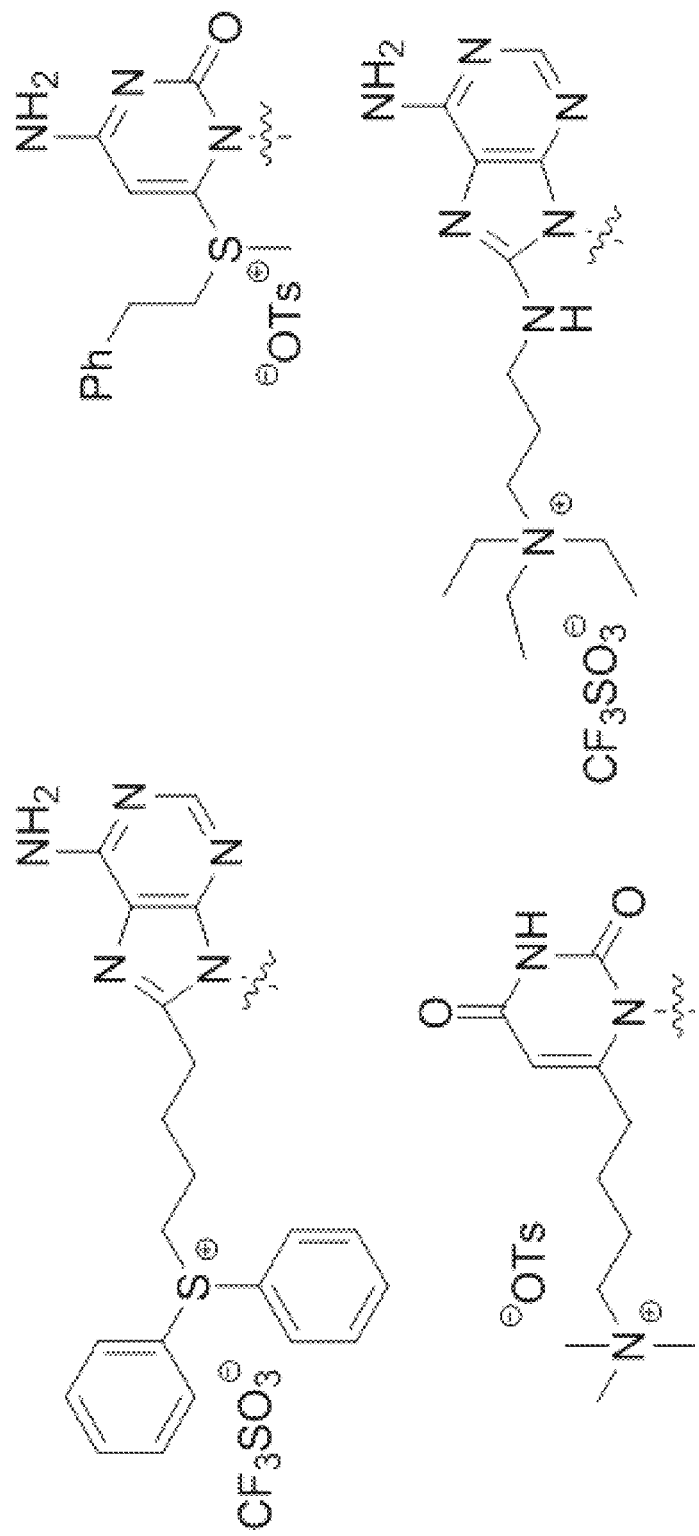
FIG. 4 shows examples of salts including photoactive groups bound to a nucleobase.

In other such embodiments, the tag may even be attached in such a way as to create an onium salt or any other otherwise ionic organic salts that can release acidic or basic species upon homolysis. Examples of such salts include photoactive groups covalently bonded in FIG. 4.

Figure 5:
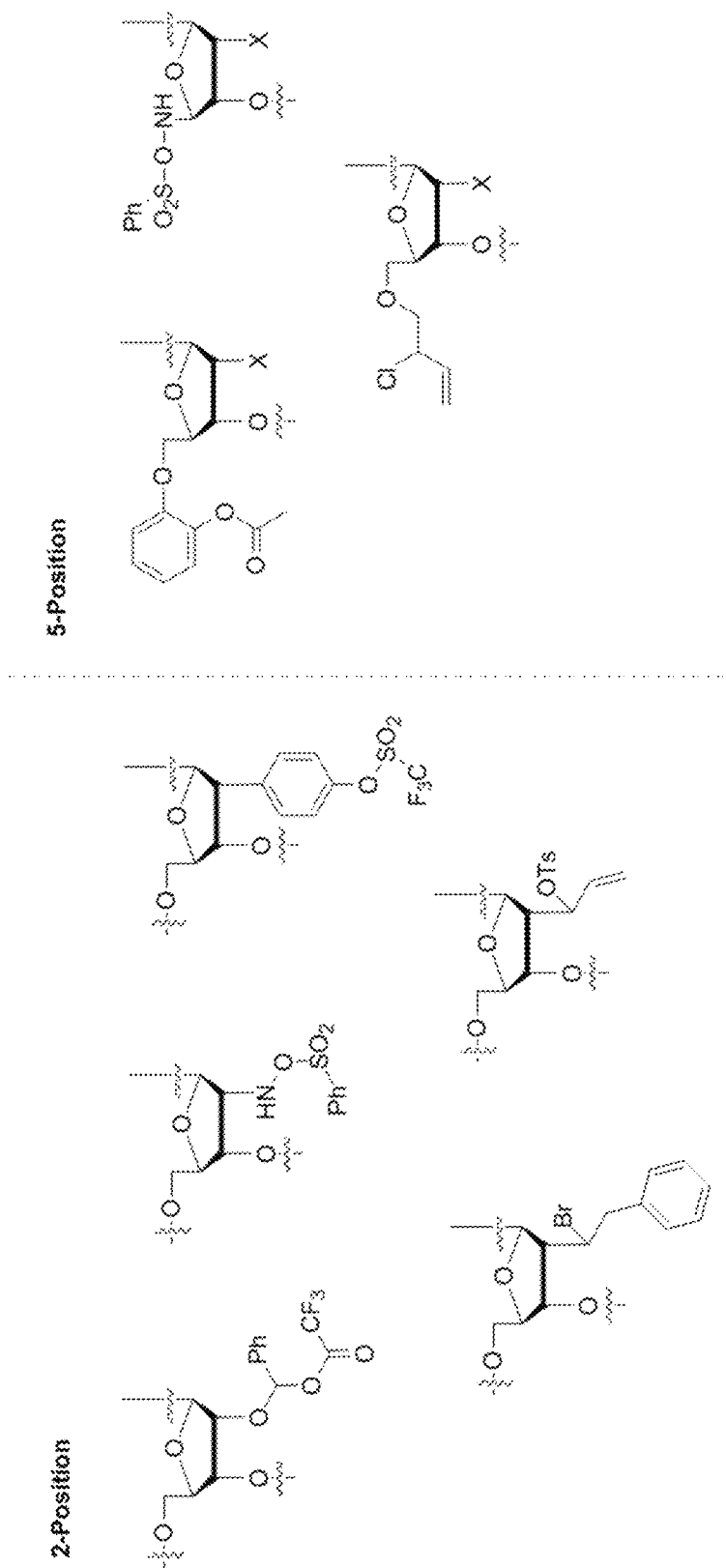
FIG. 5 shows examples of photoactive groups bound at the 2' or 5' position of the ribose component of a nucleotide.

In other embodiments, the photoactive group is covalently attached to the five carbon saccharide at the 2-position. The photoactive group need not be covalently bonded thru an oxygen atom at the 2-position, rather a carbon-carbon, carbon-nitrogen, or even a carbon-sulfur bond may be constructed and the photoactive group tag may be covalently bonded on the substituent at that is connected at the 2-position. Some non-limiting examples of tags at the 2-position include those in FIG. 5.

In other embodiments, the photoactive group need not be covalently attached thru the nucleobase of a nucleotide and instead, can be covalently attached thru the 3' position, covalently bonded to the hydroxyl or not, otherwise alternatively covalently bonded thru the carbon atom at the 3' position, on the saccharide residue or covalently attached to an oxygen atom on the phosphate group of a nucleotide. In other embodiments, the photoactive group is non-covalently bonded to an oxygen atom on the phosphate group of a nucleotide.

Alternatively, the photoactive group can be attached non-covalently thru a chelate to one or more non-terminal nucleotides. For instance if the nucleotide is modified to have a linker functional group, say ethylene diamine, that forms an cooper (Cu) metal atom chelate, a photoactive group may be non-covalently attached to the nucleotide via the metal chelate.

Nucleotides can be modified to attach a photoactive molecule or functional group on either a carbon atom or a nitrogen atom of the nitrogenous base (so long as the covalent bond to the nitrogen atom does not adversely affect the biological activity, structural integrity, or recognition of the nucleotide). A couple of examples reactions bonding a photoactive molecule to the nitrogenous base of a nucleotide follow.

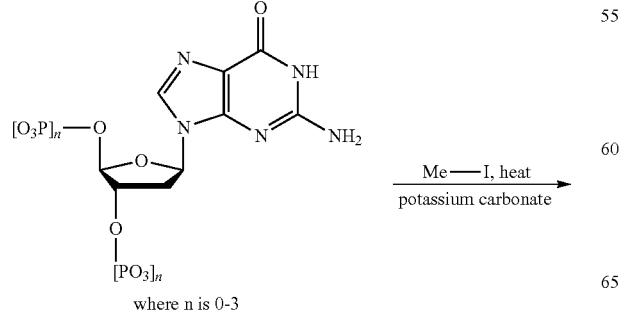

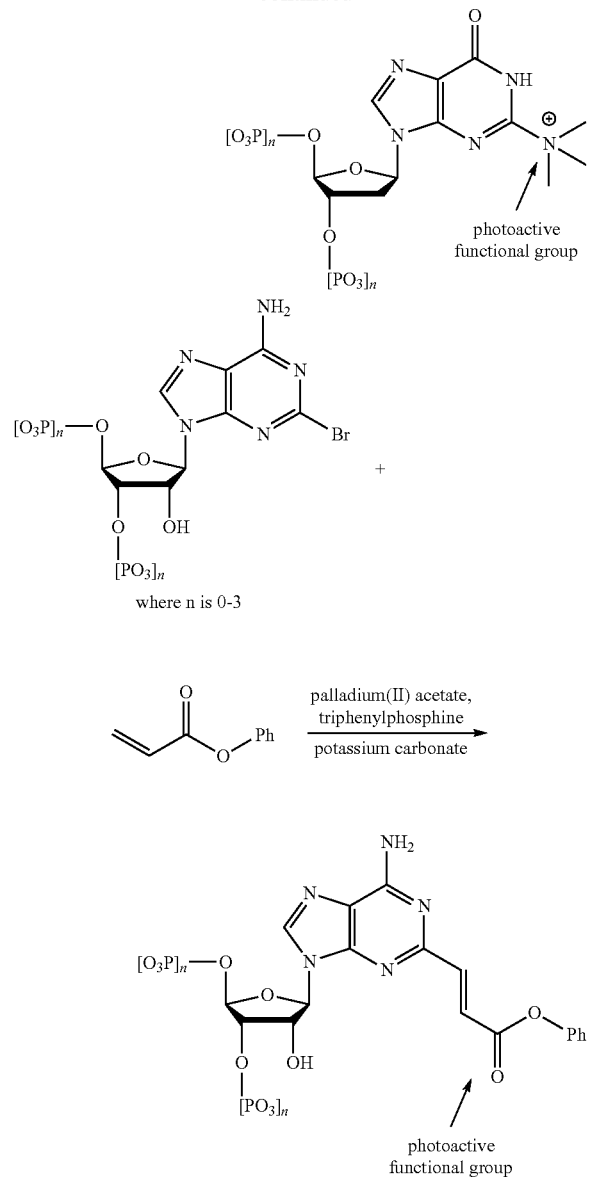

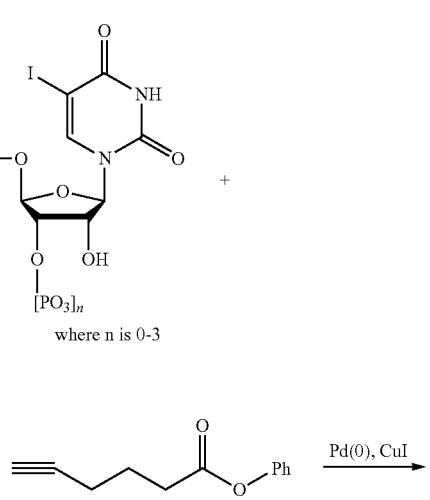

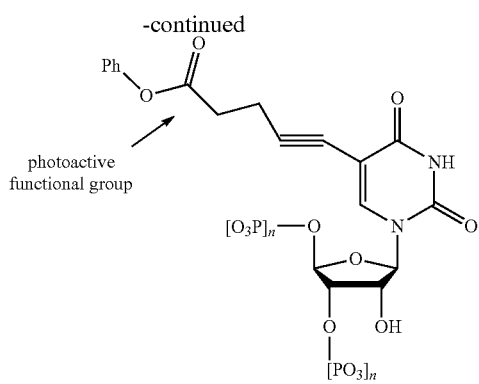

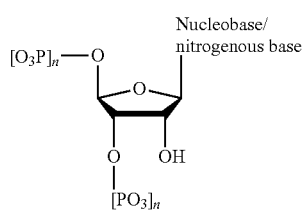

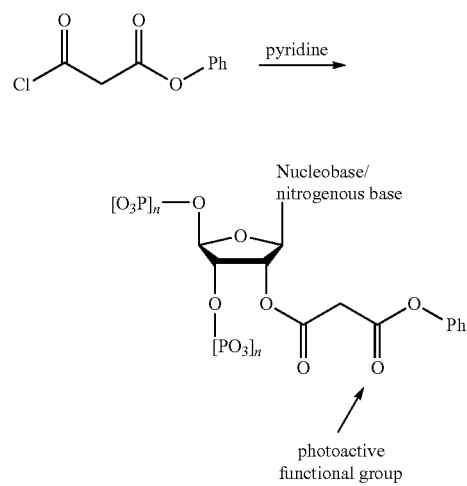

In one embodiment, a nucleotide is covalently bonded thru a linker to the photoactive group. In such an embodiment, the linker can be from one (1) to forty (40) atoms in length.

In some embodiments, the modified nucleotides described herein are incorporated into a polynucleotide probe that can bind specifically via hybridization to a target biomolecule comprising a polynucleotide sequence complementary to a portion of said polynucleotide probe. The photoactive group can be placed at a specific region of the polynucleotide probe. In some embodiments, the photoactive group is positioned at the end of the polynucleotide probe. In some embodiments, a polynucleotide probe comprises multiple photoactive groups placed at multiple positions along the nucleotide sequence.

Removable Blocking Groups

Figure 6A:
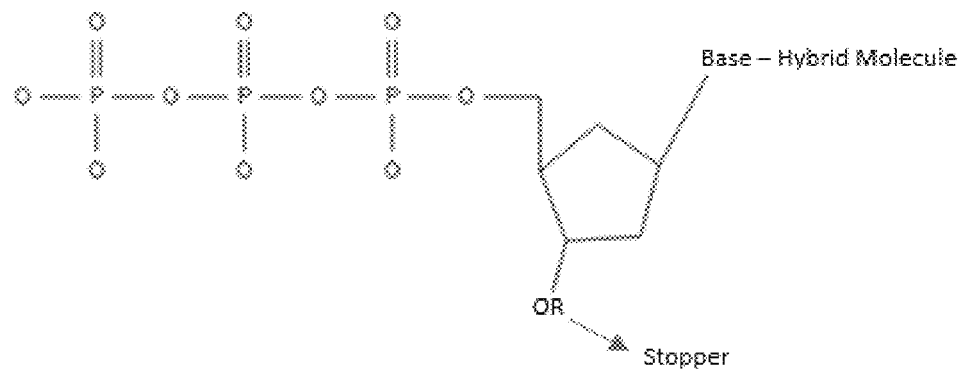
FIGS. 6A and 6B shows embodiments of a removable blocking group (e.g., a reversible terminator) bound to a 3' carbon of a sugar moiety on a nucleotide (FIG. 6A) or to the base of a nucleotide (FIG. 6B).
Figure 6B:
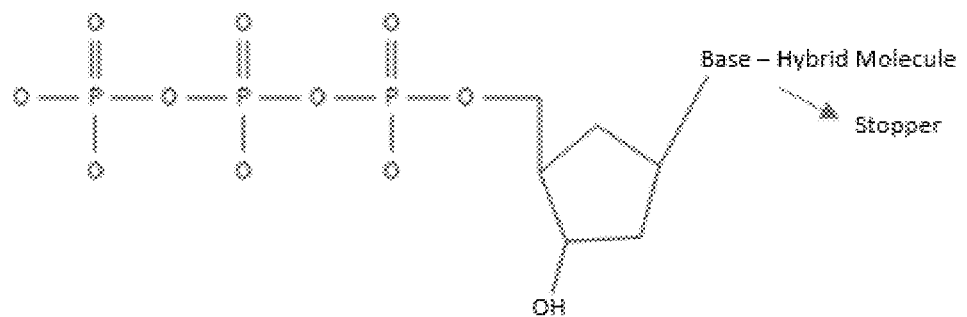

In some embodiments, the modified nucleotides comprise blocking groups that prevent addition of more than one modified nucleotide during a reaction to polymerize a growing strand of an oligonucleotide. In some embodiments, the blocking group is a fixed terminator group, such as a dideoxy terminator. In some embodiments, the blocking group is a removable blocking group, such as a reversible terminator. In some embodiment, the removable blocking group is photocleavable such that, upon exposure to light, it is removed to allow subsequent addition of nucleotides to the growing strand. In some embodiments, the modified nucleotide comprises a 3'-bound removable blocking group (FIG. 6A) where the blocking group —OR is linked to the oxygen atom of the 3'-OH of the pentose, while the photoactive group is linked to the base and is used for detection of the base attached. In some embodiments, the removable blocking group is the same group or bound to the same region of the nucleotide as the photoactive group.

In general, removable blocking groups can be used in sequencing-by-synthesis approaches that infer the sequence of a template by stepwise primer elongation. The sequencing process can involve (i) immobilizing the template and primers on the wafer; (ii) primer extension by one base and termination; (iii) obtaining the pH reading to identify the added nucleotide; (iv) removal of the blocking group that prevents the following polymerase addition; (v) washing and repeating the steps (ii-iv).

Peptides Comprising Photoactive Groups

Peptides can be modified to attach a photoactive molecule or functional group on the side chain. For example, the amine functional group on the side chain of a lysine amino acid residue in a given peptide sequence can be used in a nucleophilic displacement reaction with an electrophilic photoactive molecule. Such electrophilic species are easily prepared, for examples, aryl alkyl esters can be modified to the corresponding halo-aryl alkyl ester through an electrophilic aromatic substitution reaction. The halo-aryl alkyl ester is now an electrophile and can be used in an aromatic nucleophilic substitution reaction with the amine functional group of the lysine residue to create a covalent bond between the nitrogen atom on the side chain of lysine to the carbon atom (where the halogen resided) on the aromatic ring of the photoactive molecule.

Of course, covalent bonds are not the only means that are described herein to bond one or more photoactive molecule(s) or functional group(s). Ionic bonds, Van der Waals bonding and the like are also encompassed within the present disclosure. The skilled artisan will recognize the functional groups on a given biomolecule that can provide such bonding, e.g. a charged phosphonate group on, say, a nucleic acid may be used for an ionic bond or a terminal carboxylate on a peptide may be also be used (under basic conditions of course). The skilled artisan need only consult a text or literature reference to use a synthetic method to make these bonds.

As such, a given covalent bond on the biomolecule may be made to any carbon atom or heteroatom so long as that attachment does not alter the biological function of the biomolecule. For example, a covalent bond may attach a photoactive molecule or functional group to a nucleic acid. This bond may be attached thru say, a carbon atom on a guanine nitrogenous base to, for instance, an oxygen atom of the photoactive molecule or functional group. This type of conjugation is well within the parameters of the present disclosure as long as the nucleic acid does not lose biological activity, or perhaps the nucleic acid sequence readability with DNA polymerase.

An exemplary reaction scheme for binding a photoactive compound to a protein is shown below:

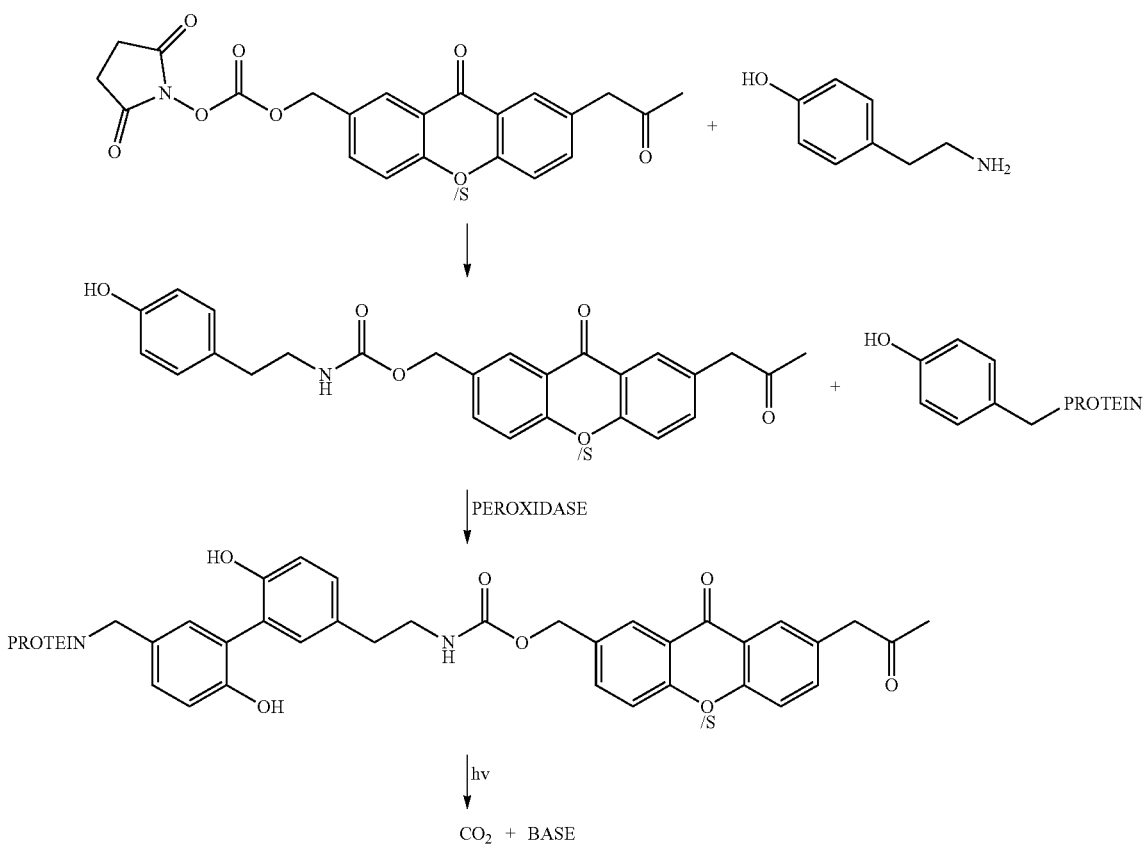

Synthesis of Photoactive Groups or Compounds

Photoactive compounds or functional groups (i.e. organic functional groups), are needed as small molecules in the present disclosure and can be purchased "off the shelf" from a petrochemical vendor such as Sigma Aldrich, VWR, Fisher Scientific, etcetera or can be easily synthesized by the skilled artisan trained in classical organic syntheses. The breadth of small organic molecules (or functional groups) that are encompassed within the present disclosure is relatively large. However, one skilled in organic synthesis will instantly identify numerous classical reactions that will produce the requisite molecule from readily available starting material. Apropos, many of the photoactive molecules (or functional groups), and the covalent bonds needed to synthesize them, are single step preparations or otherwise relatively facile chemistry for those in the art.

The compounds described herein can be prepared by any of the applicable techniques of organic synthesis. Many such techniques are well known in the art. However, many of the known techniques are elaborated in Compendium of Organic Synthetic Methods (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., Advanced Organic Chemistry, 3rd Edition, John Wiley & Sons, New York (1985); Comprehensive Organic Synthesis. Selectivity, Strategy & Efficiency in Modern Organic Chemistry, In 9 Volumes, Barry M. Trost, Editor-in-Chief, Pergamon Press, New York (1993); Advanced Organic Chemistry, Part B: Reactions and Synthesis, 4th Ed.; Carey and Sundberg; Kluwer Academic/Plenum Publishers: New York (2001); Advanced Organic Chemistry, Reactions, Mechanisms, and Structure, 2nd Edition, March, McGraw Hill (1977); Protecting Groups in Organic Synthesis, 2nd Edition, Greene, T. W., and Wutz, P. G. M., John Wiley & Sons, New York (1991); and Comprehensive Organic Transformations, 2nd Edition, Larock, R. C., John Wiley & Sons, New York (1999).

The skilled artisan can easily identify a given functional group as photoactive since only those groups will form an organic acid or base possessing a proton or heteroatom that is recognizable as an acidic or basic group upon homolysis of the bond attaching that group to the compound. In this regard, the skilled artisan quickly recognizes a photoactive group by working backward to identify functional groups in a sense. For example, tertiary amine compounds are recognized by organic chemists to be an organic base because there is more electron density on the nitrogen atom of a tertiary amine, as opposed to a secondary amine. Apropos, a skilled artisan would recognize that a compound that has a quaternary amine functional group that will, upon homolysis, form a tertiary amine functional group, is a photoactive compound or functional group of the present disclosure. Of course, most any functional group can be considered, to some extent, acidic or basic. Therefore, photoactive compounds or functional groups of the present disclosure will only include those which have a significant pKa so that one skilled in the art would instantly recognize that an organic acid or base would be generated. Thus, it is fair to generalize that the organic functional groups acidic or basic for photochemical use herein generally, though not always, include a bond to heteroatom. More specifically, the heteroatoms that include oxygen, nitrogen, sulfur, and the halogens are especially attractive because homolysis of a compound containing these heteroatoms will produce a compound that is acidic having an oxygen-hydrogen or halogen-hydrogen bond; or will be basic having a lone pair of electrons on a sulfur, oxygen, or nitrogen atom. Of course, these are not the extent of or entire list of heteroatoms that the skilled artisan will recognize as being potentially acidic or basic, but these are, generally, speaking the most common. Such organic functional groups produced from the homolysis of a moiety having a covalent bond to a heteroatom include, but are not limited to: carboxylate esters (O—C bond homolysis forming the requisite carboxylic acid), α-halogenated ethers (O—C bond homolysis forming the requisite α-haloalcohol), α-nitro ethers (O—C bond homolysis forming the requisite α-nitroalcohol), phenyl ethers (O—C bond homolysis forming the requisite phenol), sulfonate esters (O—C bond homolysis forming the requisite organic sulfonic acid), phosphonate esters (O—C bond homolysis forming the requisite organic phosphonic acid), and anhydride (O—C bond homolysis forming the requisite organic carboxylic acid).

Of course, the skilled artisan will consult the relevant literature to synthesize the requisite covalent bonds to produce photoactive compounds or functional groups. Particularly attractive review articles that are on point include: Shirai, M.; Tsunooka, M., "Photoacid and photobase generators: chemistry and applications to polymeric materials" *Progress in Polymer Science* 1996, 21(1), 1-45.; Shirai, M.; Suyama, K.; Okamura, H.; Tsunooka, M., "Development of novel photosensitive polymer systems using photoacid and photobase generators" *Journal of Photopolymer Science and Technology* 2002, 15(5), 715-730; Houlihan, F. M.; Neenan, T. X.; Reichmanis, E.; Kometani, J. M.; Chin, T., "Design, synthesis, characterization, and use of all-organic, nonionic photogenerators of acid" *Chemistry of Materials* 1991, 3(3), 462-71; Ahmad Hasan, Klaus-Peter Stengele, Heiner Giegrichl, Paul Cornwell, Kenneth R. Isham, Richard A. Sachleben, Wolfgang Pfleiderer, and Robert S. Foote, Photolabile Protecting Groups for Nucleosides: Synthesis and Photodeprotection Rates, *Tetrahedron*, Vol. 53, No. 12, pp. 4247-4264, 1997; Serafinowski and Garland, *J Am. Chem. Soc.* 2003, 125, 962-965; Iwashima, C.; Imai, G.; Okamura, H.; Tsunooka, M.; Shirai, M., "Synthesis of i- and g-line sensitive photoacid generators and their application to photopolymer systems" *Journal of Photopolymer Science and Technology* 2003, 16(1), 91-96; Okamura, Haruyuki; Sakai, Koichi; Tsunooka, Masahiro; Shirai, Masamitsu; Fujiki, Tsuyoshi; Kawasaki, Shinich; Yamada, Mitsuaki. I-line sensitive photoacid generators and their use for photocrosslinking of polysilane/diepoxyfluorene blend. Journal of Photopolymer Science and Technology (2003), 16(1), 87-90; Okamura, Haruyuki; Sakai, Koichi; Tsunooka, Masahiro; Shirai, Masamitsu. Evaluation of quantum yields for decomposition of I-line sensitive photoacid generators. Journal of Photopolymer Science and Technology (2003), 16(5), 701-706; and Okamura, Haruyuki; Matsumori, Ryosuke; Shirai, Masamitsu. I-line sensitive photoacid generators having thianthrene skeleton. Journal of Photopolymer Science and Technology (2004), 17(1), 131-134.

The skilled artisan can also consult literature and/or textbooks on organic syntheses involving carbon-heteroatom bond construction. Such texts include, but are not limited to: Yudin, A., Catalyzed Carbon-Heteroatom Bond Formation, Wiley-VCH Verlag, Weinheim, Germany (2011); Taber, D. and Lambert, T., Organic Synthesis: State of the Art 2011-2013, Oxford Press, Oxford, (2015); and Wolfe, J., Synthesis of Heterocycles via Metal-Catalyzed Reactions that Generate One or More Carbon-Heteroatom Bonds Springer, New York, (2013).

Forthwith disclosed are some very general synthetic methods, known in the art, for constructing photoactive groups that include organic functional groups such as: alcohol, carboxylate esters, sulfonate esters, phosphonate esters, and ethers. Examples of these reactions or perhaps representative reaction schemes follow.

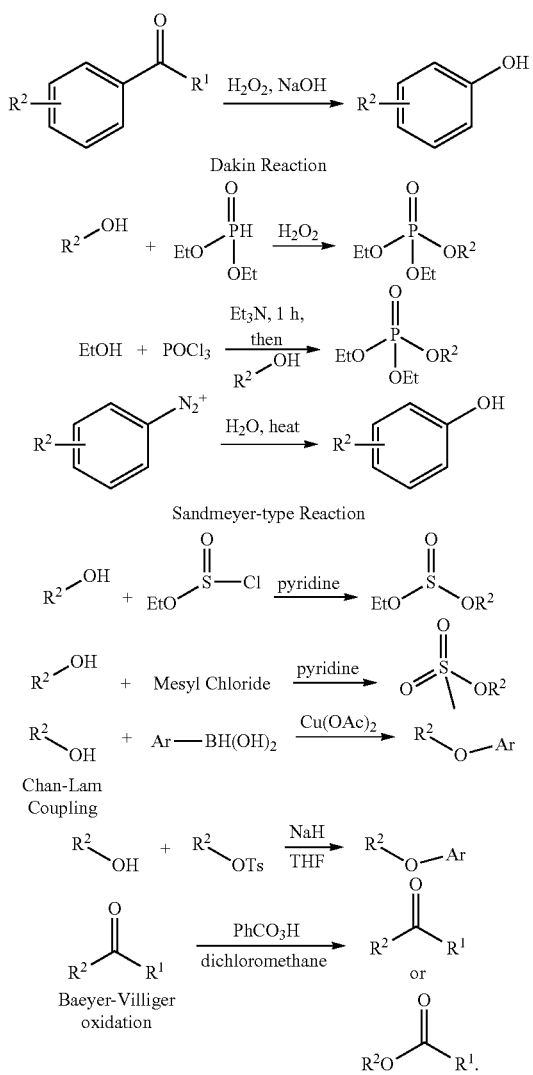

Such that $R^1$ and $R^2$ do not contain functional groups that are acidic, basic, nucleophilic or electphilic enough so as to affect the reaction described.

In one embodiment, one or more photoactive compounds or functional groups are covalently or non-covalently bonded to one or more biomolecules. In one embodiment, the biomolecule is an antibody. In one embodiment, the biomolecule is a peptide.

In one embodiment, the biomolecule is a nucleic acid. In one embodiment, the biomolecule is RNA. In one embodiment, the biomolecule is DNA.

In some aspects, one or more photoactive groups or compounds include biomolecules that have one or more photoactive groups conjugated to it, i.e. covalently attached, much like a tag. In some aspects, the one or more photoactive groups are not covalently attached to the biomolecule but rather they are bound to it in a complex or by other means of chemical bonding such as by an ionic bond, a Van der Waals bond, or a hydrogen bond.

In a general aspect, additional components such as a solvent, reagents such as homolysis initiating compounds, whole biological cells, and/or additional photoactive compound(s) or biomolecules (e.g. additional antibodies) may be present or otherwise added to the substrate and/or biological molecule.

In one embodiment, the biomolecule is any combination of, or all of, one or more peptides and/or one more nucleotides having up to two photoactive groups on any given single peptide and/or nucleotide. In one embodiment, the biomolecule is a cell receptor antigen.

Methods of Use

The technology described herein related to modified probes and related methods, compositions, kits, and systems for binding probes modified to comprise a photoactive group and specifically binding the probes to target biomolecules for detection via monitoring pH after exposure of the probes to an activating radiation.

In some embodiments, provided herein is a method for detecting a target biomolecule, comprising: a) providing probe capable of binding specifically to a target biomolecule, wherein said probe is bound to a photoacid generator or a photobase generator; b) contacting a sample suspected of comprising said target biomolecule with said probe; c) removing unbound probes from said sample; d) exposing said sample to an wavelength of light capable of activating said photoacid generator or said photobase generator, such that said probe, if bound to said target biomolecule, releases an acid or a base upon exposure to said wavelength of light; and e) detecting a concentration of ions in the sample, thereby identifying the presence or absence of said target analyte based on a change of said concentration of ions.

In some embodiments, the probe comprises a polynucleotide or a polypeptide. In some embodiments, the probe is an antibody. In some embodiments, the concentration of ions is determined by measuring an ionic strength of the sample. In some embodiments, the ionic strength is measured using an ion-sensitive field effect transistor. In some embodiments, the sample is immobilized on the surface of a substrate.

In some embodiments, the substrate is an array. In some embodiments, the array comprises a plurality of wells, wherein said wells each comprise a sensor for detecting an ionic strength of a solution in said wells. In some embodiments, the sensor is an ion-sensitive field effect transistor.

In some embodiments, provided herein is a method of detecting a sequence identity of a target polynucleotide, comprising: a) providing a substrate an immobilized target polynucleotide hybridized to a primer or probe; b) contacting said immobilized target polynucleotide with a solution comprising reagents for performing a polymerase extension reaction, said solution comprising a set of modified nucleotides comprising a photoactive group and a blocking group; c) exposing said substrate to conditions to promote incorporation of one of said modified nucleotides at the 3' end of said primer or probe; d) washing said substrate to remove unbound modified nucleotides; e) exposing said immobilized target polynucleotide to a wavelength of light to induce said photoactive group to generate an acid or a base, thereby generating a detectable change in ion concentration in a solution surrounding said immobilized target polynucleotide if said modified nucleotide is incorporated into said target polynucleotide; f) detecting said change in ion concentration; and g) determining a sequence identity of said target polynucleotide from said detected change in ion concentration.

The technology described herein relates to modified nucleotides and related methods, compositions, kits, and systems for sequencing nucleic acids. Sequencing by synthesis relies on the incorporation of a nucleotide into a growing strand to form a correct cognate pair with a template strand. Either one nucleotide can be added at a time, and the incorporation of the correct nucleotide detected by various methods, or multiple nucleotides can be added, and the identity of the incorporated nucleotide for each growing strand identified by a detectable marker on the incorporated nucleotide after removal of all non-bound nucleotides. This type of reaction normally proceeds one nucleotide at a time, and thus the modified nucleotides additional comprise a removable blocking group, i.e., an element bound to the nucleotide that prevents incorporation of another nucleotide into the growing strand. This can be as simple as a dideoxy terminator, or can be a reversible terminator, allowing for subsequent polymerization of the growing strand for additional sequencing detection.

In many instances of sequencing by synthesis, a fluorophore is used as the detectable marker. However, imaging an array comprising millions of fluorophores and processing that image into useable data can take significant time and is computationally intensive. Furthermore, the use of fluorophores as a detectable marker introduces limitations on the minimum size of features on an array due to diffraction-limited sensing. Electronic detection, such as ISFET, can remove the diffraction-limited minimum size, and allow for simultaneous detection of a signal from millions of samples on multiple arrays. However, limitations on the availability of detectable markers to effectively distinguish between multiple nucleotides using electronic sensing is limited, and sensitivity needs to be improved. Therefore, provided herein are improved modified nucleotides to facilitate electronic detection to distinguish between at least four different nucleotides in a sequencing by synthesis reaction with high sensitivity and specificity.

The modified nucleotide provided herein can include photoactive groups capable of generating an ionic signal when cleaved by light. In some embodiments, the photoactive groups are photoacid generators that decrease the pH of a solution when exposed to light. In some embodiments, the photoactive groups are photobase generators that increase the pH of a solution when exposed to light. Thus, according to methods provided herein, a modified nucleotide comprising a photoactive group can be incorporated into a growing strand in a reaction chamber if it forms a complementary base pairing with the template strand, followed by removal of un-incorporated nucleotides from the reaction chamber. Then, the reaction chamber can be exposed to light sufficient to induce photocleavage of the photoactive group, and the pH of the solution can be monitored to determine the effect of the exposure to light on the reaction solution. A change in pH and its magnitude as detected by ISFET can be used to determine whether a nucleotide was incorporated, and if so, the identity of this nucleotide. Thus, in some embodiments, provided herein are novel methods and compositions for sequencing using modified nucleotides comprising photoactive groups capable of generating an ionic signal, e.g., through the release of an acid or a base, such as a photoacid or photobase generator.

In some embodiments, sequencing is performed by sequencing by synthesis of a clonal population of oligonucleotides, or by sequencing by synthesis of a single molecule. In some embodiments, a signal is generated to determine the identity of a nucleotide incorporated into the growing strand by electronic detection.

In previous generations of sequencing using electronic detection, one type of nucleic base at time added for sequencing relays on weak $H^+$ produced by each base. This not only limits the throughput of sequencing, but also requires a very sensitive Ion sensitive Field effective transistor which limits the feature size of the ion sensing GATE of the transistor, and therefore the diversity of sequencing signals that can be generated by different nucleotides.

Herein we provide improved methods and compositions for electronic detection of nucleotide or base identity using sequencing by synthesis. Herein we provide modified nucleotides that do not rely on a weak $H^+$ produced by nucleic base addition, but instead can be detected by a strong $H^+$ or $OH^-$ produced by a non-interfering photo-energy to produce a desired ion strength for detection in a reaction area on an array. These compositions allow us to decouple ion production for sensing from the nucleic acid base coupling to the growing strand. Since a strong H+ or OH− signal with varying ion strength can be generated by our modified nucleotides, then four nucleic acid bases can be simultaneously added at each coupling to sequence genome to generate a very high throughput. Furthermore, the strong electronic signal produced allows sensitive detection and specific discrimination among the four nucleotides to enhance the accuracy of sequencing information generated.

In some embodiments, the modified nucleotides comprise photoactive groups (i.e., photosensitive molecules) such as a photoacid or a photobase generator (i.e., a molecule capable of generating a Photogenerated acid or base), and can be referred to herein as a photosensitive molecule (PM). In some embodiments, the photosensitive molecule (PM) can be a molecule capable of producing a designed pH change when exposed UV light. In some embodiments, the photogenerated acid or base can be based on salt formulation, for example one photoactive positive or negative charged molecule and one base or acid molecule together form a salt. In some embodiments, the Photogenerated acid or base can be based on photo-cleavage, for example the PM comprises one photocleavage group (e.g., a linker) and one photoactive group covalently bonded to an acid or base which is released upon exposure to a light source.

Shown below is an example of a reaction of a nucleotide comprising a photoactive group and a removable blocking group (indicated as a "STOPPER") to control polymerization during sequencing by synthesis. The photoactive group is cleaved upon exposure to radiation to generate a detectable species.

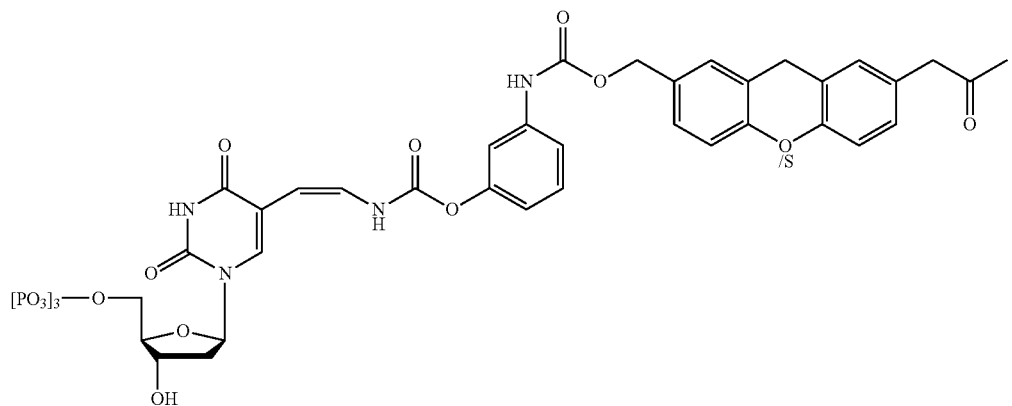

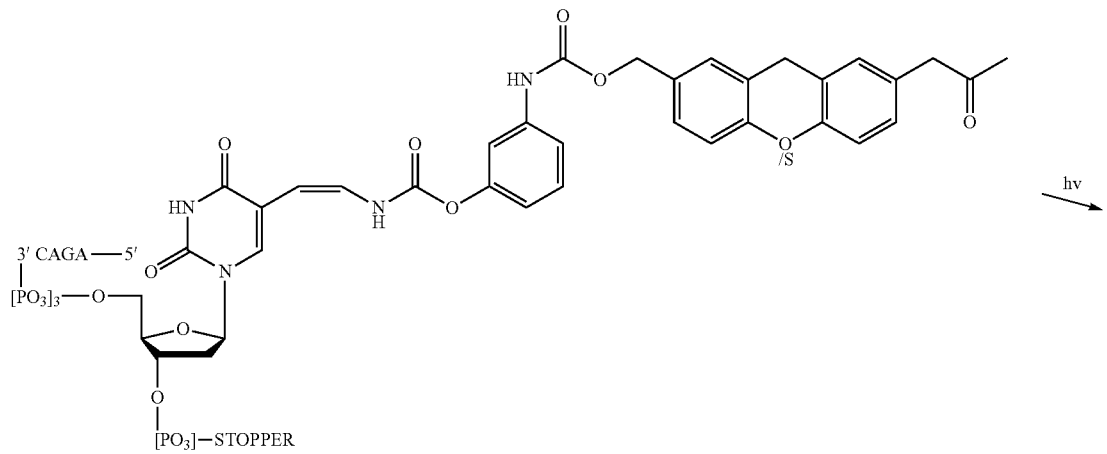

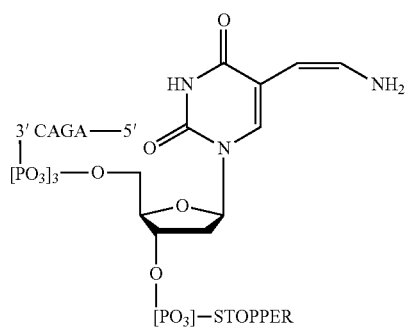
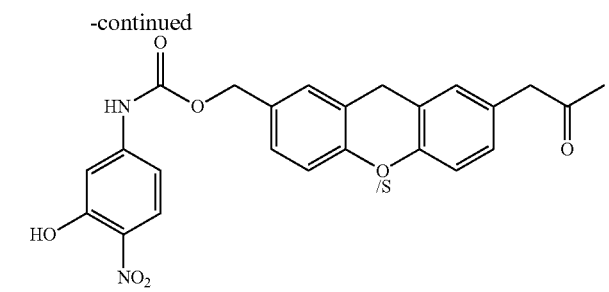

In some embodiments, the modified nucleotides or photosensitive molecules comprising photoactive groups comprise a nucleotide molecule bound to a photocleavable linker bound to a photoinduced base or acid producing molecule. In some embodiments, the modified nucleotides further comprise a removable blocking group to inhibit addition of more than one nucleotide to the end of the growing strand. Examples of removable blocking groups include dideoxy terminators and reversible terminators. The modified nucleotide may also include a photoactive group that also acts as a removable blocking group, such that, when non-interfering photo-energy is applied to cleave photobase or photoacid generator, a signal for detection is generated and the growing strand is activated to allow coupling of the next incoming nucleotide during the next cycle of nucleotide addition.

Sequencing can occur on an array to template strands bound to an array in a chamber for electronic or ionic detection. Examples of methods of electronic or ionic detection include ISFET, ChemFET, and MOSFET. An array can comprise a plurality of reaction chambers or areas each capable of detecting ionic changes to the solution in each of the reaction chambers or areas. Each reaction chamber or area can comprise a plurality of clonal oligonucleotides for sequencing, or a single bound oligonucleotide for single molecule synthesis.

As provided herein, sequencing of oligonucleotides bound in an array can continue as follows: A mixture comprising reagents for amplification of primer extension, e.g., a polymerase, a set of modified nucleotides and other reagents to facilitate the incorporation of the correct nucleotide into the growing strand hybridized to a template to be sequenced, is added to a reaction chamber (FIG. 7). The reaction is allowed to proceed to incorporate one complementary modified nucleotide into the growing strand. Then the reagents including unbound modified nucleotides are removed from the solution, e.g., by washing, leaving only the modified nucleotide (or nucleotides for clonal sequencing) incorporated into the growing strand in the reaction chamber. The reaction chamber is exposed to light (e.g., UV light) (FIG. 7), which activates the photobase or photoacid generators to adjust the pH of the reaction chamber. This change in ionic conditions can then be detected by the sensors in the reaction chamber, e.g., ISFET. The pH of the chamber is detected and can be used to determine the identity of the nucleotide incorporated into the growing strand in the preceding nucleotide addition cycle, which can then be used to determine the identity of the nucleotide base in the template strand.

In some embodiments, as shown in FIG. 7, the reagents for amplification include four modified nucleotides. These four modified nucleotides are each capable of adjusting the pH of the solution in the reaction chamber by a defined amount to provide information on the identity of the incorporated nucleotide. In some embodiments, as shown in FIG. 7, the four modified nucleotides can comprise photobase or photoacid generators. Two or more photobase generators can be used which have distinguishable ionic strengths to allow discrimination by unique pH levels in the reaction chamber after exposure to light. Two or more photoacid generators can be used which have distinguishable ionic strengths to allow discrimination by unique pH levels in the reaction chamber after exposure to light.

Figure 8:
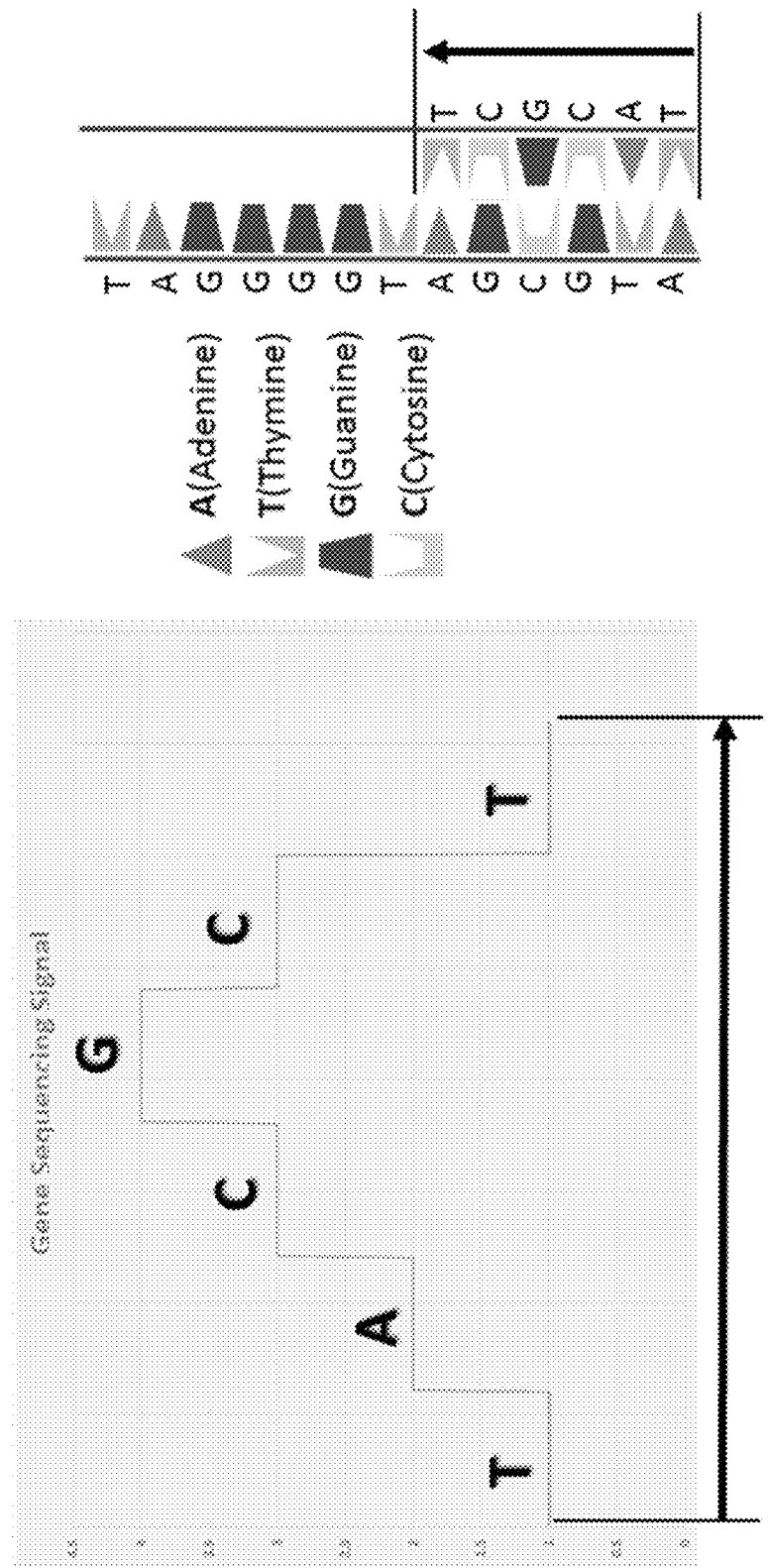
FIG. 8 shows results of a DNA sequencing reaction using modified nucleotides described herein and detected by monitoring pH. The sequential cycled addition of nucleotides to a growing strand generates a sequence of signals which corresponds to the sequence of the synthesized oligonucleotide or the template strand (SEQ ID NO: 27).

During the photoacid or photobase production, the ion level changes in the reaction chamber solution generated by the photoacid/photobase generation and detected by ion-sensitive gate of field effective transistor can then be classified and analyzed according to the four types of nucleic acid bases (FIG. 8). In some embodiments, additional cycles of sequencing are perform to generate sequencing information for a stretch of oligonucleotides on the template strand. In this embodiment, the reaction chamber can be neutralized to revert the pH to 7 before proceeding with the next reaction. In addition, if a removable blocking group is still present on the modified nucleotide, it should be removed to allow addition of the next incoming modified nucleotide on the growing strand in the next cycle. Multiple cycles can be performed and analyzed as shown in FIG. 8 to detect a sequence of oligonucleotides.

Arrays

Figure 9:
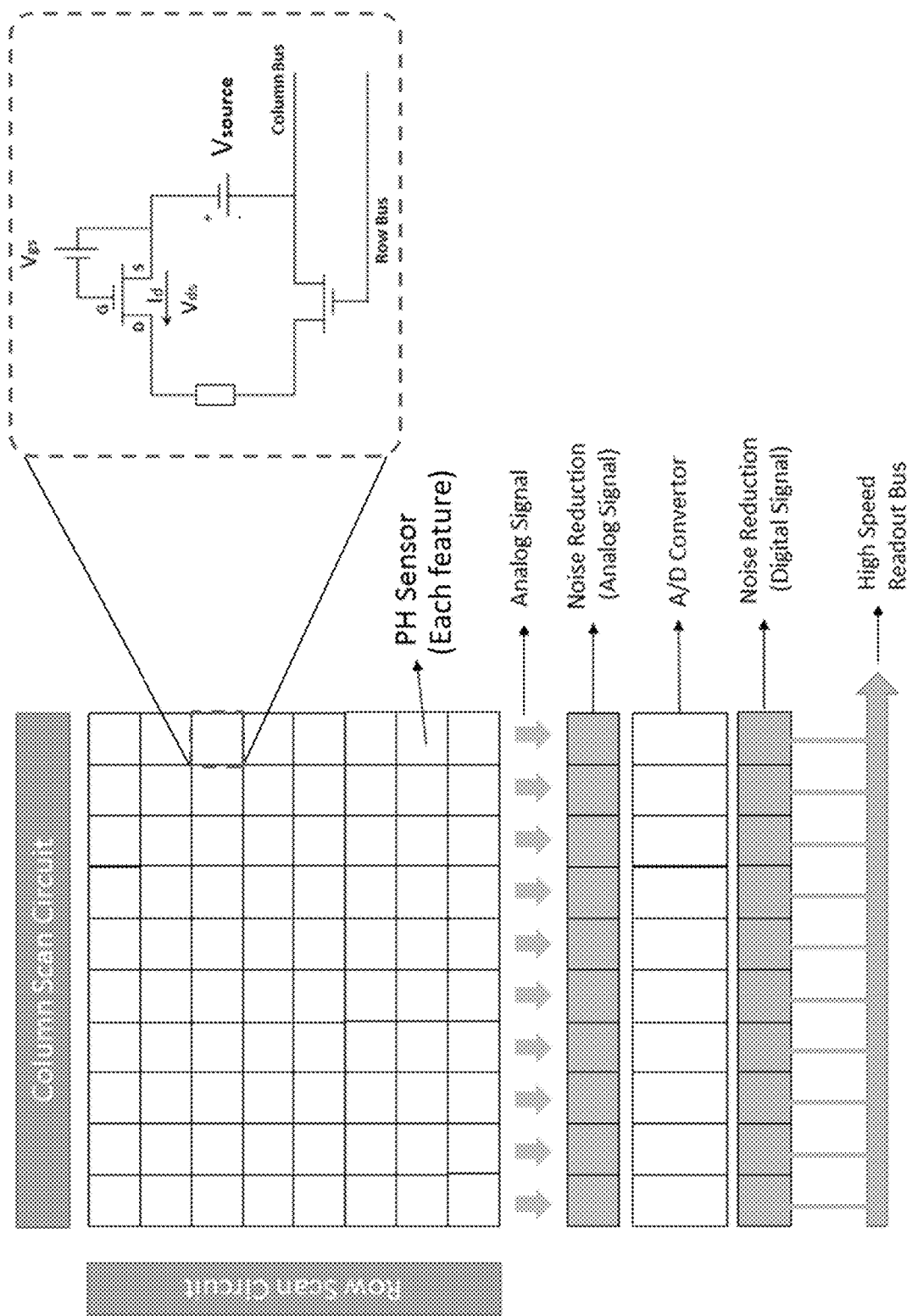
FIG. 9 provides an example of such an array comprising a plurality of ISFET sensors arranged along a grid.

Methods of detection using photoactivated compounds is described herein using arrays. The arrays comprise multiple pH sensors, such as ion-sensitive field effect transistors (ISFET), which are sensitive to small perturbations in ionic strength and can be provided in miniaturized features on an array. Shown in FIG. 9 is an example of an array of wells each comprising a pH sensor, such as an ISFET sensor. Each well can have one or more target biomolecules bound therein, which can be detected or otherwise characterized, such as by sequencing, using the methods and photoactive compounds as described herein. Uses of the arrays disclosed herein can include research applications, therapeutic purposes, medical diagnostics, and/or stratifying one or more patients.

Any of the arrays described herein can be used as a research tool or in a research application. In one aspect, arrays can be used for high throughput screening assays. For example, substrates comprising immobilized probes comprising DNA (deoxyribonucleic acid), RNA (ribonucleic acid), PNA (peptide nucleic acid), LNA (locked nucleic acid), or hybrid combinations thereof can be tested by subjecting the array to a DNA or RNA molecule and identifying the presence or absence of the complimentary DNA, RNA, or PNA molecule, e.g., by detecting at least one change among the features of the array. PNA-DNA chimeric substrates can be tested by subjecting the array to a complementary DNA molecule and performing a single nucleotide extension reaction to determine whether the substrate is biologically active, and to identify a SNP in a sample.

Figure 10:
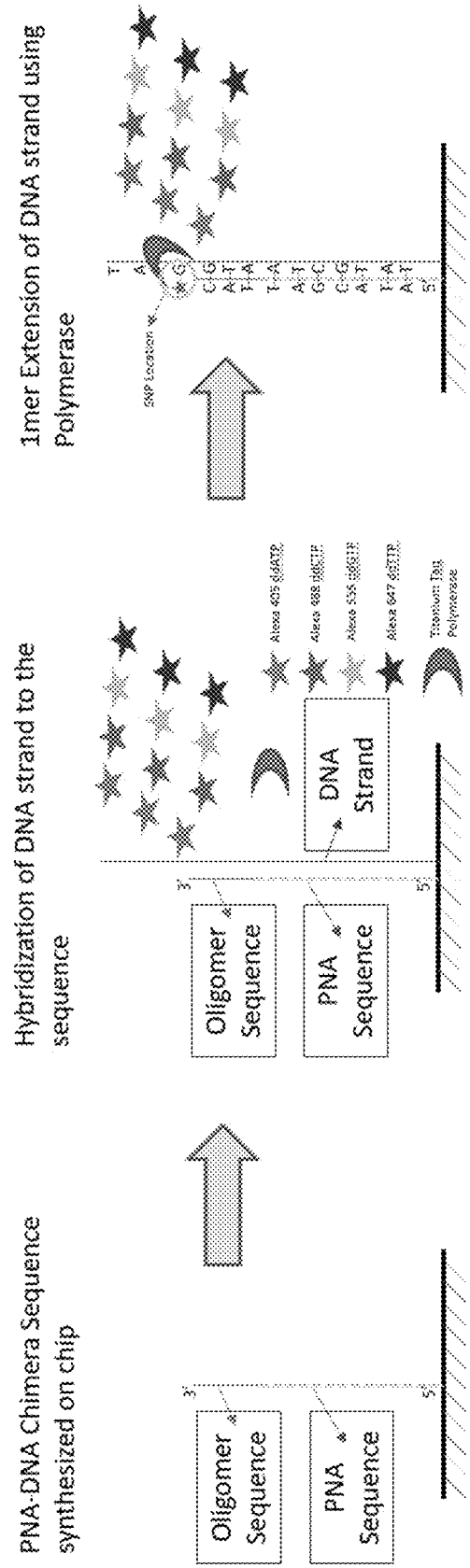
FIG. 10 depicts an exemplary single nucleotide primer extension reaction to detect a sequence variant (SEQ ID NOS 28-29, respectively, in order of appearance).

In some embodiments, an array can be used for detection of sequence variants in a sample, e.g., single nucleotide polymorphisms (SNPs). Detection of sequence variants can occur through observing sequence-specific hybridization of labeled molecules to a probe on an array. Detection of sequence variants can also occur through binding of a sequence suspected of having a sequence variant to a probe on an array, followed by performing a polymerase extension reaction with a labelled nucleotides. In preferred embodiments, PNA-DNA chimeric oligonucleotide probes are bound to the array and hybridize to nucleotide sequences from a sample suspected of comprising a sequence variant. The PNA-DNA chimeric oligonucleotides are enzymatically active, i.e., they are capable of acting as a substrate for complementary nucleotide incorporation into a growing strand using a polymerase under preferred conditions for polymerization. FIG. 10 provides an exemplary scheme for detecting the identity of a sample oligonucleotide hybridized to a PNA-DNA chimeric oligonucleotide covalently attached to the array using a polymerase-based single nucleotide extension reaction with a labeled nucleotide. Examples of PNA-DNA chimeric oligonucleotide-based methods for SNP detection are provided in U.S. Pat. No. 6,316,230, incorporated herein by reference in its entirety.

Arrays can also be used in screening assays for ligand binding, to determine substrate specificity, or for the identification of complimentary DNA, RNA, PNA molecule that are expressed in certain cells in vivo or in vitro. Labeling techniques, protease assays, as well as binding assays useful for carrying out these methodologies are generally well-known to one of skill in the art.

In some embodiments, an array can be used to represent a predefined PNA chain as a sequence of overlapping PNA sequences. For example, the PNA sequence of a known gene is divided into overlapping sequence segments of any length and of any suitable overlapping frame, and PNA chains corresponding to the respective sequence segments are in-situ synthesized as disclosed herein. The individual PNA segments so synthesized can be arranged starting from the amino terminus of the predefined PNA chain.

In some embodiments, a sample is applied to an array having a plurality of random PNA chains. The random PNA chains can be screened and BLASTed to determine homologous domains with, e.g., a 90% or more identity to a given nucleotide sequence. In some aspect, the whole PNA sequence can then be synthesized and used to identify potential markers and/or causes of a disease of interest.

In some embodiments, an array is used for high throughput screening of one or more genetic factors. DNA or RNA expression associated with a gene can be investigated through PNA hybridization, which can then be used to estimate the relation between gene and a disease.

In another example, an array can be used to identify one or more biomarkers. Biomarkers can be used for the diagnosis, prognosis, treatment, and management of diseases. Biomarkers may be expressed, or absent, or at a different level in an individual, depending on the disease condition, stage of the disease, and response to disease treatment. Biomarkers can be, e.g., DNA, RNA, PNA, proteins (e.g., enzymes such as kinases), sugars, salts, fats, lipids, or ions.

Arrays can also be used for therapeutic purposes, e.g., identifying one or more bioactive agents. A method for identifying a bioactive agent can comprise applying a plurality of test compounds to an array and identifying at least one test compound as a bioactive agent. The test compounds can be small molecules, aptamers, oligonucleotides, chemicals, natural extracts, peptides, proteins, fragments of antibodies, antibody like molecules, or antibodies. In some embodiments, test compounds are hybridizing DNA, RNA or PNA sequences. The bioactive agent can be a therapeutic agent or modifier of therapeutic targets. Therapeutic targets can include phosphatases, proteases, ligases, signal transduction molecules, transcription factors, protein transporters, protein sorters, cell surface receptors, secreted factors, and cytoskeleton proteins.

In one aspect, also provided are arrays for use in medical diagnostics. An array can be used to determine a response to administration of drugs or vaccines. For example, an individual's response to a vaccine can be determined by detecting the gene expression levels of the individual by using an array with PNA chains or PNA-DNA chimeric oligonucleotide chains representing particular genes associated with the induced immune response. Another diagnostic use is to test an individual for the presence of biomarkers, wherein samples are taken from a subject and the sample is tested for the presence of one or more biomarkers.

Arrays can also be used to stratify patient populations based upon the presence or absence of a biomarker that indicates the likelihood a subject will respond to a therapeutic treatment. The arrays can be used to identify known biomarkers to determine the appropriate treatment group. For example, a sample from a subject with a condition can be applied to an array. Binding to the array may indicate the presence of a biomarker for a condition. Previous studies may indicate that the biomarker is associated with a positive outcome following a treatment, whereas absence of the biomarker is associated with a negative or neutral outcome following a treatment. Because the patient has the biomarker, a health care professional may stratify the patient into a group that receives the treatment.

In some embodiments, a method of detecting the presence or absence of a expressed gene of interest in a sample can include obtaining an array disclosed herein and contacted with a sample suspected of comprising the DNA or RNA sequence of a gene of interest; and determining whether the gene of interest is expressed in the sample by detecting the presence or absence of binding to one or more features of the array. In some embodiments, the DNA or RNA sequence of the gene of interest can be obtained from a bodily fluid, such as amniotic fluid, aqueous humour, vitreous humour, bile, blood serum, breast milk, cerebrospinal fluid, cerumen, chyle, endolymph, perilymph, feces, female ejaculate, gastric acid, gastric juice, lymph, mucus, peritoneal fluid, pleural fluid, pus, saliva, sebum, semen, sweat, synovial fluid, tears, vaginal secretion, vomit, or urine.

In some embodiments, a method of identifying a vaccine candidate can include obtaining an array disclosed herein contacted with a sample derived from a subject previously administered the vaccine candidate, wherein the sample comprises a plurality of DNA or RNA sequences; and determining the binding specificity of the plurality of DNA or RNA sequences to one or more features of the array. In some embodiments, the features comprise a plurality of distinct, nested, overlapping PNA chains comprising subsequences derived from a known nucleotide sequence.

In one embodiment, the two or more different photoactive groups are bound by the target biomolecules on the array or substrate such that upon exposure to light, one group reacts and affects the pH selectively. In such embodiments, both of, or the plurality of, photoactive groups will affect the pH, however, one photoactive group will affect the pH significantly more. In some such embodiments, one photoactive group will affect the pH at least half an order of magnitude more, viz. a measurable change in the pH of the surrounding environment is at least 0.5 units in magnitude different than what is predicted for the plurality of one or more photoactive groups to affect the pH. In some such embodiments, one photoactive group will affect the pH at least one order of magnitude more. In some such embodiments, one photoactive group will affect the pH at least two orders of magnitude more. In some such embodiments, two or more photoactive groups will each affect the pH at least half an order of magnitude more than what is predicted for each one of the other one or more photoactive groups to affect the pH.

Herein also disclosed the inventors have contemplated that each and every embodiment and/or aspect may be used in any combination with any other embodiment and/or aspect. For examples, photoactive compounds or functional groups of the present disclosure can include any combination of the HOMO. LUMO, pKa, or absorbed light energy within the ranges set forth.

Substrates and arrays suitable for binding probes and target biomolecules for use in detection of the photoactive groups and target biomolecules as described herein are disclosed at least in PCT Publication No. WO 2013/119845, PCT Publication No. WO 2014/052989, PCT Publication No. WO 2014/078606, PCT Publication No. WO 2014/127328, PCT Publication No. WO 2015/127409, PCT Publication No. WO 2016/145434, and PCT Publication No. WO 2017/117292, the entirety of which are each incorporated by reference.

Results Analysis and Information Storage

In some embodiments, the method of sequencing using modified nucleotides or the array comprising hybrid PNA/DNA probe oligonucleotides is part of a system, such as a diagnostic or sequencing system or platform that provides highly-multiplexed sequencing results to users.

Figure 11:
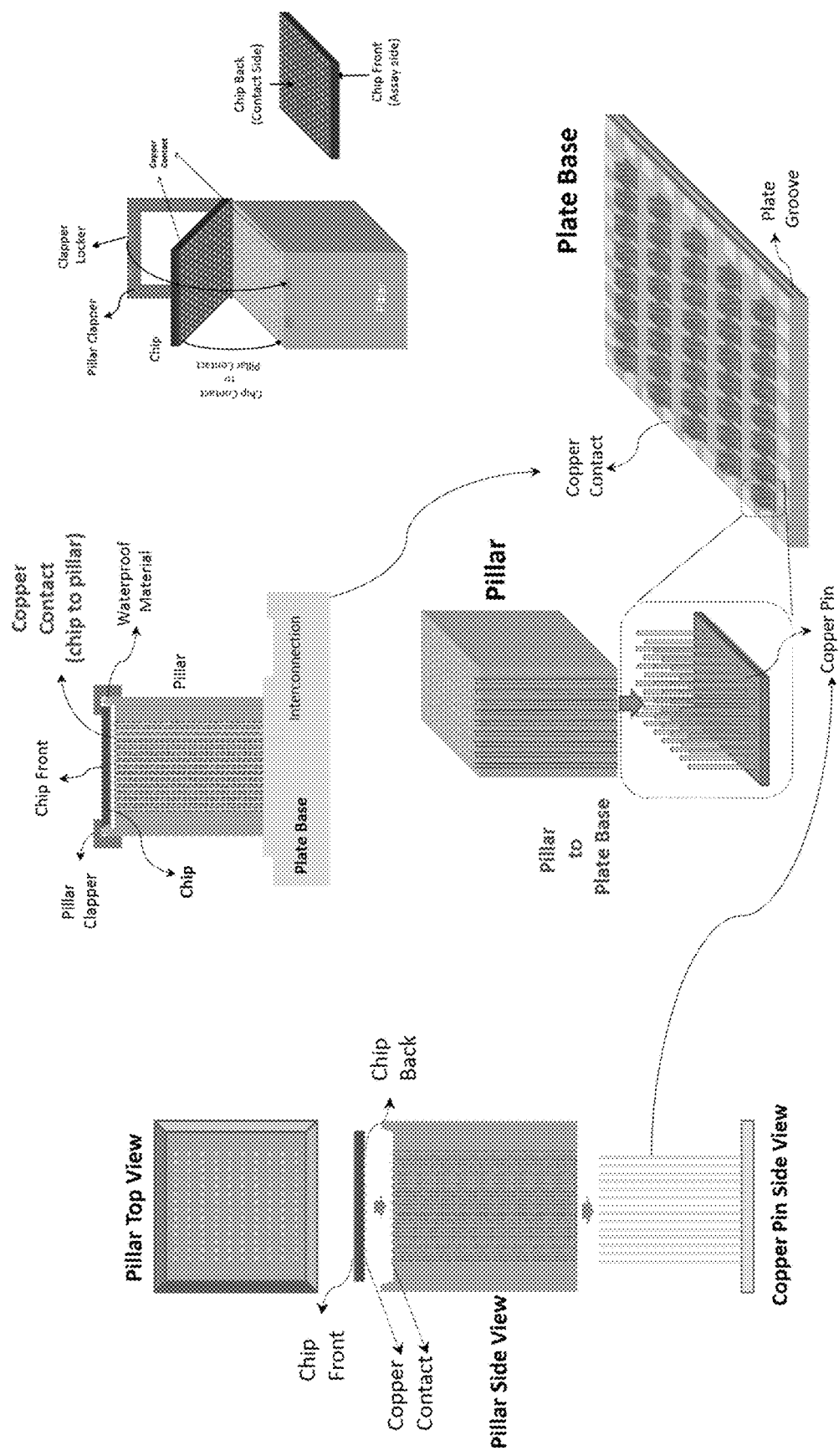
FIG. 11 shows a diagram of a system including a device that interfaces with a chip or array as described herein to collect data from the chip and process it. Examples of mechanisms to obtain information from each of the multiple reaction areas on the array are shown.
Figure 12:
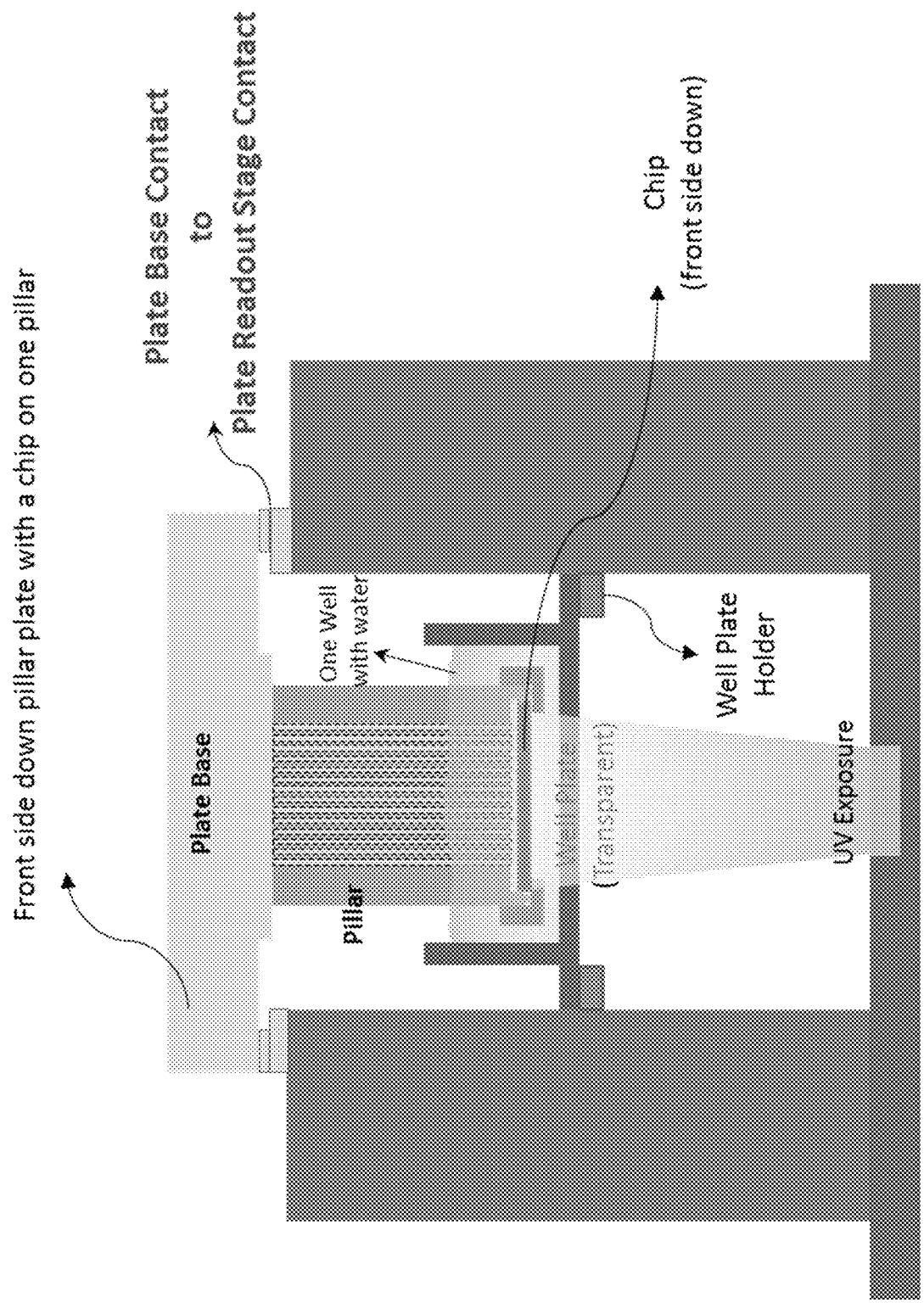
FIG. 12 shows a plate base contact to plate base readout stage and elements for UV exposure to induce photoactivation or photocleavage, according to an embodiment of the invention.

In some embodiments, provided herein is a sequencing system in which a sample is added to a sequencing array, and oligonucleotides from the sample are sequenced using the methods and compositions described herein. FIGS. 11 and 12 provide examples of systems that can be used to mount an array provided herein and receive electrical signals from each well to perform a sequencing reaction. FIG. 11 shows a diagram of a system including a device that interfaces with a chip or array as described herein to collect data from the chip and process it. Examples of mechanisms to obtain information from each of the multiple reaction areas on the array are shown. FIG. 12 shows a plate base contact to plate base readout stage and elements for UV exposure to induce photoactivation or photocleavage, according to an embodiment of the invention.

A reader can be used to read the sequencing array. For example, the sequencing array may be inserted into the reader, or placed on or inside the reader. In some embodiments, the reader provides an interface with the sequencing array to allow multiplexed electronic detection of sequencing, e.g., by detection of changes to pH such as through ISFET detection. The reader identifies electrical signals in each reaction area or well on an array from incorporated modified nucleotides after exposure to light to induce photoacid or photobase generation. The reader then reads the pH of each reaction chamber, and determines the identity of the incorporated nucleotide. In some embodiments, the reader includes a display, such as a screen, that allows it to display to the user the results of sequencing. In some embodiments, the confidence level of a nucleotide identification can also be determined and provided for display on the reader.

In some embodiments, a software program installed on the reader may compare one or more electronic signals from a reaction chamber with a reference electronic signal associated with a nucleotide. The program can perform this process through a number of cycles to generate a sequence of an oligonucleotide contained within a reaction area of the array. In some embodiments, the software program is a computer readable medium storing instructions on the reader that when executed by a processor within the reader cause the processor to perform certain actions, such as identifying the pH of a reaction area or storing certain data, such as sequencing data. In some embodiments, the software program comprises one or more software modules that perform each of the various functions described above for the reader.

Figure 13:
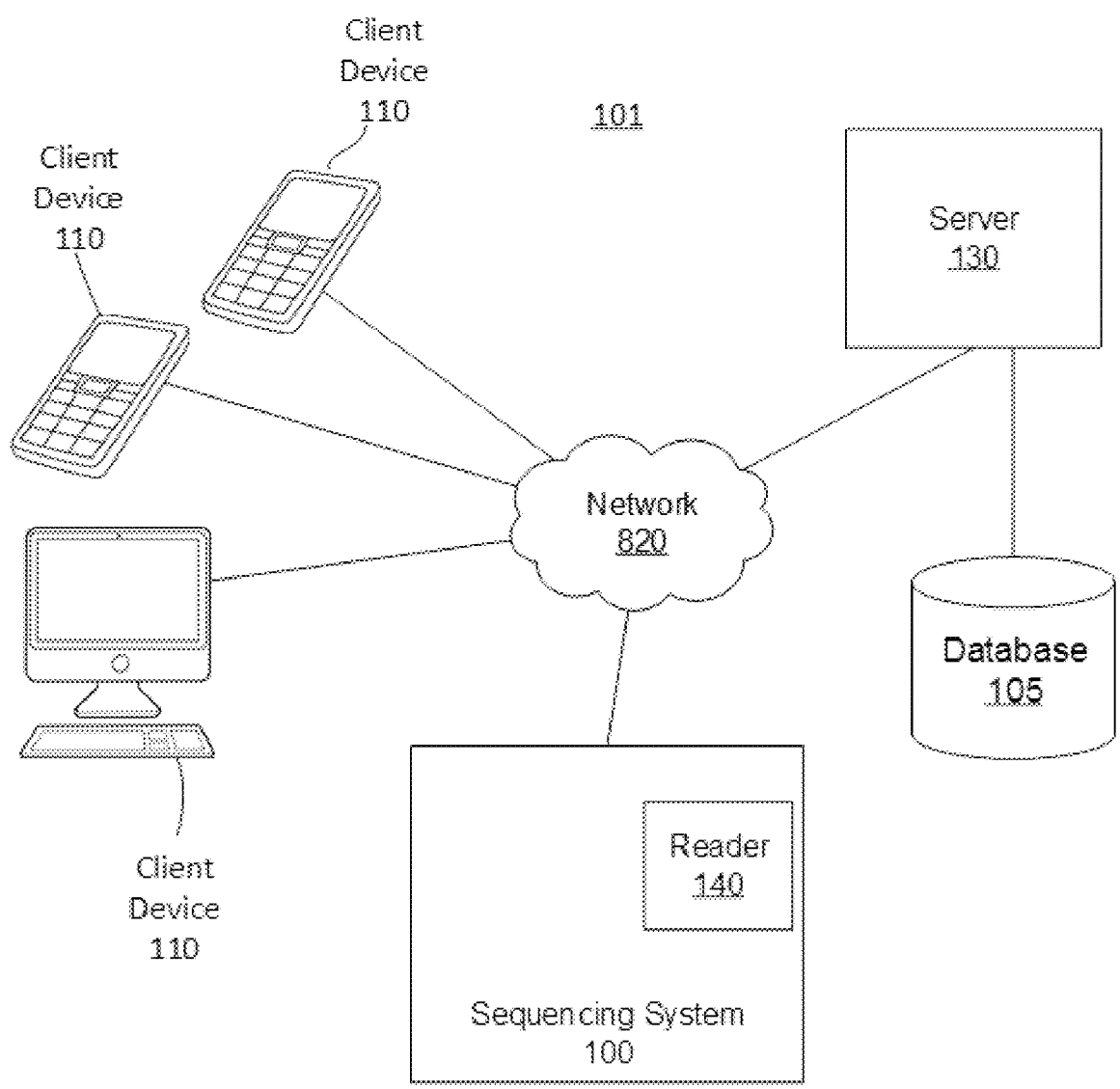
FIG. 13 is a network diagram of an example system environment including the sequencing system in communication with one or more client devices and one or more servers via a network.

FIG. 13 illustrates a system environment 101 including the sequencing system 100 described above, according to an embodiment. The system environment 101 can further include one or more client devices 110, one or more servers 130, a database 105 accessible to the server 130, where all of these parties are connected through a network 120. In other embodiments, different and/or additional entities can be included in the system environment 101.

The system environment 101 allows the results from the reader 140 to be shared via network 120 with one or more other users at their client devices 110, including being shared with family, friends, physicians or other medical personnel, schools, civil response teams, among others. Results can also be uploaded to the web.

The network 120 facilitates communications between the components of the system environment 101. The network 120 may be any wired or wireless local area network (LAN) and/or wide area network (WAN), such as an intranet, an extranet, or the Internet. In various embodiments, the network 120 uses standard communication technologies and/or protocols. Examples of technologies used by the network 120 include Ethernet, 802.11, 3G, 4G, 802.16, or any other suitable communication technology. The network 120 may use wireless, wired, or a combination of wireless and wired communication technologies. Examples of networking protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over the network 120 may be represented using any suitable format, such as hypertext markup language (HTML) or extensible markup language (XML). In some embodiments, all or some of the communication links of the network 120 may be encrypted using any suitable technique or techniques.

The client device(s) 110 are computing devices capable of receiving user input as well as transmitting and/or receiving data via the network 120. In one embodiment, a client device 110 is a conventional computer system, such as a desktop or laptop computer. Alternatively, a client device 110 may be a device having computer functionality, such as a personal digital assistant (PDA), a mobile telephone, a smartphone or another suitable device. A client device 110 is configured to communicate via the network 120.

In some embodiments, the system environment 101 may include one or more servers, for example where the sequencing system includes a service that is managed by an entity that communicates via the network 120 with the reader 140 and/or any of the client devices 110. The server 130 can store data in database 105 and can access stored data in database 105. Database 105 may be an external database storing sequencing data, medical information, user or patient history data, etc. The server 130 may also store data in the cloud. In some embodiments, the server 130 may occasionally push updates to the reader 140, or may receive result data from the reader 140 and perform certain analyses on that result data and provide the analyzed data back to the reader 140 or to a client device 110.

In some embodiments, the reader 140 functionality can be included in a client device 110, such as a mobile phone, and can be operated via a mobile application installed on the phone. In these embodiments, a device may be attached to the phone that allows the phone to read the test strip, or the phone's own internal hardware (e.g., imaging hardware) can be used to read the test strip. The mobile application stored on the phone can process the results read from the test strip and share the results with other devices 110 on the network 120.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ *Ed.* (Plenum Press) Vols A and B (1992).

Example 1A: Synthesis of a PNA-DNA Probes on an Array

Synthesis of PNA Sequence

To generate a PNA-DNA chimera on the surface of an array, a PNA oligo of a desired sequence at a specific site was first synthesized on a chip according to the protocol provided below:

A location-specific PNA sequence synthesis is performed on an array as follows: A wafer is spin-coated at 2000-4000 rpm (preferably 2500-3000 rpm) for 10-180 seconds (preferably for 60-120 seconds) with a photoresist composition comprising a photobase generator as described above. The wafer and photoresist is exposed to 248 nm ultraviolet light in a deep ultra violet scanner tool according to a pattern defined by a photomask, wherein the locations exposed to ultraviolet light undergo base generation due to the presence of a photobase generator in the photoactive coupling solution in the photoresist. The expose energy can be from 1 $mJ/cm^2$ to 100 $mJ/cm^2$ (preferably 30-60 $mJ/cm^2$).

After UV exposure, the surface of the wafer is post baked in a bake module. The post bake temperature can vary between 75° C. to 115° C., for a duration of at least 60 seconds (but not usually exceeding 180 seconds). The base generated at the UV-exposed regions removes a protection group on the amino groups. The photoresist is then stripped.

The free amino group is then coupled to activated R2-acetic acid by spin coating R2-acetic acid with activation agents and reacted in a bake module with the temperature varying from 55° C. to 115° C. for 60-240 seconds. Excess R2-acetic acid is removed.

Following addition of activated R2-acetic acid, a displacement reaction with a mono-amino protected ethylenediamine is performed by addition of a displacement mixture onto the surface of the wafer. This displacement mixture is spin coated on the wafer and reacted in a bake module with the temperature varying from 55° C. to 115° C. for 30 seconds-300 seconds (preferably 120 seconds). In some embodiments, a mono-amino protection group can be any amino protection group as mentioned earlier.

Next, a coupling reaction is performed with the peptide nucleic acid monomer acetic acid. The displaced amine is coupled to the activated PNA monomer acetic acid by spin coating the activated PNA monomer acetic acid with activation agents and allowing to react for 90-300 seconds.

Optionally, a capping solution coat is applied on the surface to prevent any non-reacted amino groups on the substrate from reacting to the next coupling molecule. The capping solution includes a solvent, a polymer, and a coupling molecule. The capping solution is spin-coated on the wafer at 1500-3500 rpm for at least 30 seconds and reacted in a bake module with the temperature varying from 55° C. to 95° C. for 30 seconds-90 seconds (preferably 60 seconds) to complete one cycle.

This entire cycle can be repeated as desired with different nucleic acid monomers each time to obtain desired PNA sequences at specific sites on an array.

Part 2—Synthesis of PNA-DNA Chimera Step.

Addition of a sequence-specific DNA nucleotide to the end of a PNA sequence at specific locations on an array is performed as follows: The wafer comprising PNA sequences is spin-coated at 2000-4000 rpm (preferable 2500-3000 rpm) for 10-180 seconds preferably for 60-120 seconds with the photoresist and is exposed to 248 nm ultraviolet light in a deep ultra violet scanner tool according to a pattern defined by a photomask, wherein the locations exposed to ultraviolet light undergo base generation due to the presence of a photobase generator in the photoactive coupling solution in the photoresist. The expose energy can be from 1 mJ/cm$^2$ to 100 mJ/cm$^2$ (preferably 30-60 mJ/cm$^2$).

After UV exposure, the surface of the wafer is post baked in a bake module. The post bake temperature can vary between 75° C. to 115° C., for a duration of at least 60 seconds (but not usually exceeding 180 seconds). The generated base deprotects the protection of amino groups of the PNA sequences in the exposed regions. The photoresist is then stripped.

Reverse DNA amidites are activated with phosphoramidite activation solution (including e.g., a tetrazole catalyst) and then coupled to the free amine.

Optionally, a capping solution coat is applied on the surface to prevent any non-reacted amino groups on the substrate from reacting to the next coupling molecule. The capping solution includes a solvent, a polymer, and a coupling molecule. The capping solution is spin-coated on the wafer at 1500-3500 rpm for at least 30 seconds and reacted in a bake module with the temperature varying from 55° C. to 95° C. for 30 seconds-90 seconds (preferably 60 seconds) to complete one cycle. The phosphite-triester formed in the coupling step is then converted to a stable form which is achieved by iodine oxidation in the presence of water and pyridine.

Part 3—Reverse DNA Oligonucleotide Synthesis.

A location-specific DNA sequence reverse synthesis (5' to 3') is performed at the end of each PNA-DNA chimera on the array as follows: A wafer is spin-coated at 2000-4000 rpm (preferably 2500-3000 rpm) for 10-180 seconds (preferably for 60-120 seconds) with a photoresist composition comprising a photobase generator as described above. The wafer and photoresist is exposed to 248 nm ultraviolet light in a deep ultra violet scanner tool according to a pattern defined by a photomask, wherein the locations exposed to ultraviolet light undergo acid generation due to the presence of a photoacid generator in the photoactive coupling solution. The expose energy can be from 1 mJ/cm$^2$ to 100 mJ/cm$^2$ (preferably 30-60 mJ/cm$^2$).

After UV exposure, the surface of the wafer is post baked in a bake module. The post bake temperature can vary between 75° C. to 115° C., for a duration of at least 60 seconds (but not usually exceeding 180 seconds). The acid generated deprotects the protection of hydroxyl groups of the 3'-end of DNA sequence in the exposed regions. The photoresist is then stripped.

Reverse DNA amidites are activated with phosphoramidite activation solution (including e.g., a tetrazole catalyst) and then coupled to the free hydroxyl group.

Optionally, a capping solution coat is applied on the surface to prevent any non-reacted amino groups on the substrate from reacting to the next coupling molecule. The capping solution includes a solvent, a polymer, and a coupling molecule. The capping solution is spin-coated on the wafer at 1500-3500 rpm for at least 30 seconds and reacted in a bake module with the temperature varying from 55° C. to 95° C. for 30 seconds-90 seconds (preferably 60 seconds) to complete one cycle. The phosphite-triester formed in the coupling step is then converted to a stable form which is achieved by iodine oxidation in the presence of water and pyridine.

Example 2: Hybridization of PNA-DNA Chimera to Oligonucleotide DNA Sequence and Extension with Polymerase To determine the biological activity of a PNA-DNA chimera sequence synthesized per the above protocol, a 34-mer length PNA-DNA chimera sequence 5'-GTG-GAAATTTGACATAGTCTCAGATGCCTAT(TAT)-3' (SEQ ID NO: 7) was synthesized according to Example 3 with (TAT) being the DNA oligomer portion of the PNA-DNA chimera. Four oligonucleotide DNA sequences complimentary to the sequence of the PNA-DNA chimera with one additional nucleotide were synthesized (IDT).

```
                                           (SEQ ID NO: 8)
S1: CACCTTTAAACTGTATCAGAGTCTACGGATAATAa (SEQ ID NO: 9)
S2: CACCTTTAAACTGTATCAGAGTCTACGGATAATAc (SEQ ID NO: 10)
S3: CACCTTTAAACTGTATCAGAGTCTACGGATAATAg (SEQ ID NO: 11)
S4: CACCTTTAAACTGTATCAGAGTCTACGGATAATAt
```

A primer extension reaction to detect incorporation of the correct complementary nucleotide in a primer extension reaction was performed. Alexa 405 ddATP, Alexa 488 ddCTP, Alexa 555 ddGTP, Alexa 647 ddTTP were synthesized by techniques well known to one skilled in the art. Hybridization and polymerase extension on each of the 4 chips were performed as follows. Oligomers S1, S2, S3 and S4 were diluted 1:1000 (100 nM) in 1×DNA Polymerase Buffer (Clontech), 20 nmol of MgCl2, 1 unit Titanium Taq DNA Polymerase (Clontech), and all 4 labelled ddNTPs labelled monomers (each 25 pmoles). Hybridization was done in a hybridization chamber at 55° C. for 30 minutes followed by washing the chips in 0.1× Ssarc buffer at 40° C. for 5 minutes twice followed by rinsing in DI Water. The chip was then scanned on a Nikon AIR confocal microscope which included the 4 wavelengths of the dyes used in the ddNTPs and results are depicted in Table 1.

TABLE 1

| | Hybridization and Extension of PNA-DNA Chimera Sequence | | | |
|---|---|---|---|---|
| Sequence | 405 nm | 488 nm | 561 m | 640 nm |
| S1 (a) | 950.02 | 875.54 | 1047.8 | 65124.23 |
| S2 (c) | 1051.3 | 954.2 | 65531.25 | 875.6 |
| S3 (g) | 800.3 | 65014.78 | 802.5 | 1068.9 |
| S4 (t) | 65121.13 | 1012.98 | 946.6 | 780.9 |

Example 3: Genotyping Using PNA Sequence Hybridization

Testing of the PNA synthesis for a genotyping SNP-based application was performed. Genotyping of MTHFR region, with the well-known mutations, C677T and A1298C, were tested using 20 DNA samples. The DNA samples had a known genotyping result which were determined using Real-Time PCR.

PNA Sequences were as follows:

(SEQ ID NO: 12)
GGAGAAGGTGTCTGCGGGAG(C)CGATTTCATCATCACGCAGC, (SEQ ID NO: 13)
GGAGAAGGTGTCTGCGGGAG(T)CGATTTCATCATCACGCAGC, (SEQ ID NO: 14)
GGAGGAGCTGACCAGTGAAG(A)AAGTGTCTTTGAAGTCTTCG, (SEQ ID NO: 15)
GGAGGAGCTGACCAGTGAAG(C)AAGTGTCTTTGAAGTCTTCG.

PNA sequences were synthesized on a chip using the methods given above. The location of the SNP is indicated in ( ) region (surrounded by parentheses) and is synthesized in the middle of the sequence.

DNA were extracted from the samples (buccal swabs) using methods known to one skilled in the art. A standard PCR reaction using forward primer and biotin-labelled reverse primers was performed on the extracted DNA samples. Hybridization of the PCR product on the chip was performed with the PCR product (20 ul) diluted in hybridization buffer 0.1× Ssarc Buffer 60 mM sodium chloride (Sigma) (80 ul), 6 mM sodium citrate (Sigma), 0.72 weight % N-lauroylsarcosine sodium salt solution (Sigma). Hybridization was done in a hybridization chamber at 55° C. for 2 hours followed by washing the chips in 0.1× Ssarc buffer 40° C. for 5 minutes twice. This was followed by an incubation with 1 ng/ml Atto 488 Streptavidin (Rockland) diluted in PBS buffer, washing the chips in PBS Buffer twice and rinsing in DI Water. The chip was then scanned on a Nikon AIR confocal microscope and results are depicted in Table 2 and Table 3.

TABLE 2

| | 677C > T Mutation Results (PNA) | | | | |
|---|---|---|---|---|---|
| Sample ID | Original Result | SEQ ID NO: 12 (C) | SEQ ID NO: 13 (T) | Ratio (C/T) | Calculated Result |
| MT1 | Homozygous Wild C/C | 65521.21 | 18343.16 | 3.571969606 | Homozygous Wild C/C |
| MT2 | Homozygous Wild C/C | 65227.42 | 17390.41 | 3.750769533 | Homozygous Wild C/C |
| MT3 | Homozygous Wild C/C | 65093.45 | 18262.83 | 3.564258661 | Homozygous Wild C/C |
| MT4 | Homozygous Wild C/C | 65386.72 | 16498.11 | 3.963285491 | Homozygous Wild C/C |
| MT5 | Homozygous Wild C/C | 65245.82 | 17957.35 | 3.633376862 | Homozygous Wild C/C |
| MT6 | Homozygous Wild C/C | 65399.12 | 15087.35 | 4.334698937 | Homozygous Wild C/C |
| MT7 | Homozygous Wild C/C | 65408.94 | 16166.17 | 4.046038115 | Homozygous Wild C/C |
| MT8 | Heterozygous C/T | 32656.73 | 29003.56 | 1.125955917 | Heterozygous C/T |
| MT9 | Heterozygous C/T | 31140.4 | 28860.93 | 1.078981169 | Heterozygous C/T |
| MT10 | Heterozygous C/T | 30317.09 | 27075.3 | 1.119732376 | Heterozygous C/T |
| MT11 | Heterozygous C/T | 29953.05 | 30101.53 | 0.99506736 | Heterozygous C/T |
| MT12 | Heterozygous C/T | 34884.62 | 32957.31 | 1.058478984 | Heterozygous C/T |
| MT13 | Heterozygous C/T | 28468.43 | 30134.87 | 0.944700608 | Heterozygous C/T |
| MT14 | Heterozygous C/T | 29909.26 | 26689.12 | 1.12065366 | Heterozygous C/T |
| MT15 | Homozygous Mutant T/T | 16202.94 | 65103.75 | 0.248878751 | Homozygous Mutant T/T |
| MT16 | Homozygous Mutant T/T | 16759.95 | 65465.38 | 0.256012415 | Homozygous Mutant T/T |
| MT17 | Homozygous Mutant T/T | 18019.34 | 65327.52 | 0.275830768 | Homozygous Mutant T/T |
| MT18 | Homozygous Mutant T/T | 15153.13 | 65116.35 | 0.232708529 | Homozygous Mutant T/T |
| MT19 | Homozygous Mutant T/T | 16837.25 | 65198.8 | 0.258244784 | Homozygous Mutant T/T |

TABLE 2-continued

677C > T Mutation Results (PNA)

| Sample ID | Original Result | SEQ ID NO: 12 (C) | SEQ ID NO: 13 (T) | Ratio (C/T) | Calculated Result |
|---|---|---|---|---|---|
| MT20 | Homozygous Mutant T/T | 16315.66 | 65431.64 | 0.249354288 | Homozygous Mutant T/T |
| No Template | No Template Control | 931.04 | 1010.87 | | No Template Control |

TABLE 3

1298A > C Mutation Results (PNA)

| Sample ID | Original Result | SEQ ID NO: 14 (A) | SEQ ID NO: 15 (C) | Ratio (A/C) | Calculated Result |
|---|---|---|---|---|---|
| MT1 | Homozygous Wild A/A | 65379.46 | 18466.16 | 3.540501111 | Homozygous Wild C/C |
| MT2 | Homozygous Wild A/A | 65471.94 | 15279.46 | 4.284964259 | Homozygous Wild C/C |
| MT3 | Homozygous Wild A/A | 65031.65 | 16581.28 | 3.92199215 | Homozygous Wild C/C |
| MT4 | Homozygous Wild A/A | 65219.55 | 17032.97 | 3.829018075 | Homozygous Wild C/C |
| MT5 | Homozygous Wild A/A | 65122.87 | 15781.57 | 4.126514029 | Homozygous Wild C/C |
| MT6 | Homozygous Wild A/A | 65211.42 | 16471.62 | 3.959016782 | Homozygous Wild C/C |
| MT7 | Homozygous Wild A/A | 65284.01 | 16098.4 | 4.055310466 | Homozygous Wild C/C |
| MT8 | Heterozygous A/C | 25864.99 | 26219.09 | 0.986494573 | Heterozygous C/T |
| MT9 | Heterozygous A/C | 27535.6 | 33971.8 | 0.810542862 | Heterozygous C/T |
| MT10 | Heterozygous A/C | 29798.31 | 25928.75 | 1.149238201 | Heterozygous C/T |
| MT11 | Heterozygous A/C | 31306.14 | 30412.04 | 1.02939954 | Heterozygous C/T |
| MT12 | Heterozygous A/C | 34735.37 | 26137.17 | 1.328964459 | Heterozygous C/T |
| MT13 | Heterozygous A/C | 34293.84 | 32393 | 1.058680579 | Heterozygous C/T |
| MT14 | Heterozygous A/C | 34029.48 | 29563.14 | 1.151077998 | Heterozygous C/T |
| MT15 | Homozygous Mutant C/C | 17863.25 | 65072.67 | 0.274512326 | Homozygous Mutant T/T |
| MT16 | Homozygous Mutant C/C | 15361.46 | 65400.42 | 0.234883201 | Homozygous Mutant T/T |
| MT17 | Homozygous Mutant C/C | 16092.89 | 65285.28 | 0.246501049 | Homozygous Mutant T/T |
| MT18 | Homozygous Mutant C/C | 16038.93 | 65184.73 | 0.246053485 | Homozygous Mutant T/T |
| MT19 | Homozygous Mutant C/C | 16752.2 | 65398.01 | 0.256157641 | Homozygous Mutant T/T |
| MT20 | Homozygous Mutant C/C | 16298.91 | 65253.44 | 0.249778556 | Homozygous Mutant T/T |
| No Template | No Template Control | 931.04 | 1010.87 | | No Template Control |

In this method, the SNP location is ideally close to the center of the sequence synthesized.

Example 4: Genotyping Using PNA-DNA Chimera and Primer Extension

Testing of the PNA-DNA chimera for a genotyping SNP-based application was performed. Genotyping of MTHFR region, with the well-known mutations, C677T and A1298C, were tested using 20 DNA samples. The DNA samples had a known genotyping result which were determined using Real-Time PCR. 34-mer length PNA-DNA chimera primer sequences 5'-CTGAAGCACTT-GAAGGAGAAGGTGTCTGCGG(GAG)-3' (SEQ ID NO: 16) for the 677C>T mutation and 5'-CTGAA-GATGTGGGGGGAGGAGCTGACCAGTG(AAG)-3' (SEQ ID NO: 17) for the 1298A>C mutation were synthesized according to the methods given above (with DNA nucleotide portion of the PNA-DNA chimera enclosed in parentheses).

DNA were extracted from the samples (buccal swabs) using methods known to one skilled in the art. A standard PCR reaction using forward and reverse primers was performed on the extracted DNA samples. Hybridization and polymerase extension on each of chips were performed as follows. The PCR product was mixed in 1×DNA Polymerase Buffer (Clontech), 20 nmol of MgCl$_2$, 1 unit Titanium Taq DNA Polymerase (Clontech), and all 4 labelled ddNTPs labelled monomers (each at 25 pmol). Hybridization was done in a hybridization chamber at 55° C. for 30 minutes followed by washing the chips in 0.1× Ssarc buffer 40° C. for 5 minutes twice followed by rinsing in DI Water. The chip was then scanned on a Nikon AIR confocal microscope which included the 4 wavelengths of the dyes used in the ddNTPs and results are depicted in Table 4 and Table 5.

TABLE 4

677C>T Mutation Results (PNA-DNA Chimera)

| Sample ID | Original Result | 405 nm (A) | 488 nm (C) | 561 nm (G) | 640 nm (T) | Ratio (C/T) | Calculated Result |
|---|---|---|---|---|---|---|---|
| MT1 | Homozygous Wild C/C | 987.88 | 65381.38 | 1068.03 | 1022.91 | 63.9170406 | Homozygous Wild C/C |
| MT2 | Homozygous Wild C/C | 1079.22 | 65379.69 | 1003.71 | 1088.7 | 60.0529898 | Homozygous Wild C/C |
| MT3 | Homozygous Wild C/C | 890.15 | 65426.33 | 1054.07 | 984.99 | 66.4233444 | Homozygous Wild C/C |
| MT4 | Homozygous Wild C/C | 1019.28 | 65082.83 | 1072.37 | 1005.67 | 64.7158909 | Homozygous Wild C/C |
| MT5 | Homozygous Wild C/C | 1054.92 | 65520.82 | 885.87 | 919.46 | 71.26010919 | Homozygous Wild C/C |
| MT6 | Homozygous Wild C/C | 856.58 | 65086.76 | 1063 | 1081.46 | 60.18415845 | Homozygous Wild C/C |
| MT7 | Homozygous Wild C/C | 1014.84 | 65048.37 | 1012.61 | 1020.77 | 63.72480578 | Homozygous Wild C/C |
| MT8 | Heterozygous C/T | 1086.58 | 28940.21 | 916.77 | 25640.7 | 1.128682524 | Heterozygous C/T |
| MT9 | Heterozygous C/T | 1045.85 | 34602.61 | 903.71 | 33874.1 | 1.021506402 | Heterozygous C/T |
| MT10 | Heterozygous C/T | 920.14 | 30597.21 | 1085.44 | 32891.41 | 0.930249266 | Heterozygous C/T |
| MT11 | Heterozygous C/T | 1065.78 | 26105.81 | 883.95 | 25875.75 | 1.00889095 | Heterozygous C/T |
| MT12 | Heterozygous C/T | 1087.05 | 28716.64 | 1028.78 | 30765.41 | 0.933406706 | Heterozygous C/T |
| MT13 | Heterozygous C/T | 1096.23 | 30296.19 | 1097.06 | 29260.09 | 1.035410007 | Heterozygous C/T |
| MT14 | Heterozygous C/T | 999.32 | 31152.26 | 1083.28 | 28772.12 | 1.082723831 | Heterozygous C/T |
| MT15 | Homozygous Mutant T/T | 959.46 | 920.49 | 983.83 | 65264.85 | 0.014103917 | Homozygous Mutant T/T |
| MT16 | Homozygous Mutant T/T | 999.03 | 1017.52 | 1098.91 | 65228.95 | 0.015599209 | Homozygous Mutant T/T |
| MT17 | Homozygous Mutant T/T | 908.97 | 1031.03 | 1083.42 | 65170.19 | 0.015820577 | Homozygous Mutant T/T |
| MT18 | Homozygous Mutant T/T | 1053.12 | 1000.45 | 961.54 | 65066.09 | 0.015375905 | Homozygous Mutant T/T |
| MT19 | Homozygous Mutant T/T | 1070.32 | 1075.46 | 1009.19 | 65326.99 | 0.016462721 | Homozygous Mutant T/T |
| MT20 | Homozygous Mutant T/T | 1059.73 | 915.48 | 854.63 | 65287.66 | 0.014022252 | Homozygous Mutant T/T |
| No Template | No Template Control | 1005.16 | 931.04 | 1018.61 | 1010.87 | | No Template Control |

TABLE 5

1298 A>C Mutation Results (PNA-DNA Chimera)

| Sample ID | Original Result | 405 nm (A) | 488 nm (C) | 561 nm (G) | 640 nm (T) | Ratio (A/C) | Calculated Result |
|---|---|---|---|---|---|---|---|
| MT1 | Homozygous Wild A/A | 65488.6 | 860.42 | 898.56 | 1053.57 | 76.11236373 | Homozygous Wild A/A |
| MT2 | Homozygous Wild A/A | 65344.12 | 942.87 | 1005.5 | 859.47 | 69.30342465 | Homozygous Wild A/A |
| MT3 | Homozygous Wild A/A | 65439.64 | 943 | 1040.81 | 1048.08 | 69.39516437 | Homozygous Wild A/A |
| MT4 | Homozygous Wild A/A | 65352.13 | 1015.9 | 850.32 | 978.43 | 64.32929422 | Homozygous Wild A/A |
| MT5 | Homozygous Wild A/A | 65258.17 | 1047.97 | 999.32 | 858.43 | 62.27102875 | Homozygous Wild A/A |
| MT6 | Homozygous Wild A/A | 65327.7 | 871.43 | 984.33 | 971.42 | 74.96609022 | Homozygous Wild A/A |
| MT7 | Homozygous Wild A/A | 65222.79 | 1032.19 | 1093.43 | 894.49 | 63.18874432 | Homozygous Wild A/A |
| MT8 | Heterozygous A/C | 32437.6 | 29322.89 | 851.72 | 897.02 | 1.106221113 | Heterozygous A/C |

TABLE 5-continued

1298 A>C Mutation Results (PNA-DNA Chimera)

| Sample ID | Original Result | 405 nm (A) | 488 nm (C) | 561 nm (G) | 640 nm (T) | Ratio (A/C) | Calculated Result |
|---|---|---|---|---|---|---|---|
| MT9 | Heterozygous A/C | 28901.78 | 32234.2 | 972.78 | 930.13 | 0.896618498 | Heterozygous A/C |
| MT10 | Heterozygous A/C | 31930.24 | 34009.27 | 902.33 | 1072.67 | 0.938868726 | Heterozygous A/C |
| MT11 | Heterozygous A/C | 31187.77 | 33959.45 | 1066.13 | 858.62 | 0.918382659 | Heterozygous A/C |
| MT12 | Heterozygous A/C | 35160.88 | 34129.73 | 1085.9 | 978.16 | 1.030212662 | Heterozygous A/C |
| MT13 | Heterozygous A/C | 26032.4 | 34987.94 | 980.73 | 1047.35 | 0.744039232 | Heterozygous A/C |
| MT14 | Heterozygous A/C | 32902.79 | 33518.34 | 1024.53 | 998.06 | 0.981635427 | Heterozygous A/C |
| MT15 | Homozygous Mutant C/C | 853.23 | 65405.7 | 866.06 | 1096.1 | 0.013045193 | Homozygous Mutant C/C |
| MT16 | Homozygous Mutant C/C | 861.56 | 65469.41 | 1045.55 | 1093.83 | 0.013159734 | Homozygous Mutant C/C |
| MT17 | Homozygous Mutant C/C | 948.8 | 65335.08 | 1094.53 | 1025.03 | 0.014522061 | Homozygous Mutant C/C |
| MT18 | Homozygous Mutant C/C | 853.16 | 65190.22 | 964.72 | 901.27 | 0.013087239 | Homozygous Mutant C/C |
| MT19 | Homozygous Mutant C/C | 1014.49 | 65003.94 | 1015.66 | 922.79 | 0.015606592 | Homozygous Mutant C/C |
| MT20 | Homozygous Mutant C/C | 926.32 | 65437.85 | 945.85 | 1063.8 | 0.014155722 | Homozygous Mutant C/C |
| No Template | No Template Control | 1043.98 | 1043.85 | 986.73 | 1073.34 | | No Template Control |

In this method, the sequence synthesized on the chip contains the region just before the SNP location, thereby enabling the polymerase to selectively add the matched oligomer corresponding to the SNP identity.

The PNA-DNA chimera was able to hybridize to the DNA sequence and extend accurately according to the corresponding match DNA monomer. The PNA-DNA chimera is able to obtain a high Match/Mismatch Ratio which would accurately identify SNP-based genotyping results. Ratio for Match/Mismatch sequence is 3.5-4 for PNA sequence while it is 65-70 or PNA-DNA chimera sequence. Thus, PNA-DNA chimera with high yield of the sequence and the ability to perform a polymerase extension step on chip due to the DNA oligomer present provides a high-throughput, high accuracy system for various genomics applications including, but not limited to, SNP-based genotyping and DNA sequencing.

Example 5: Synthesis of Photoactive Molecule 1 (PM1) (dCTP-PAG1)

Figure 14:
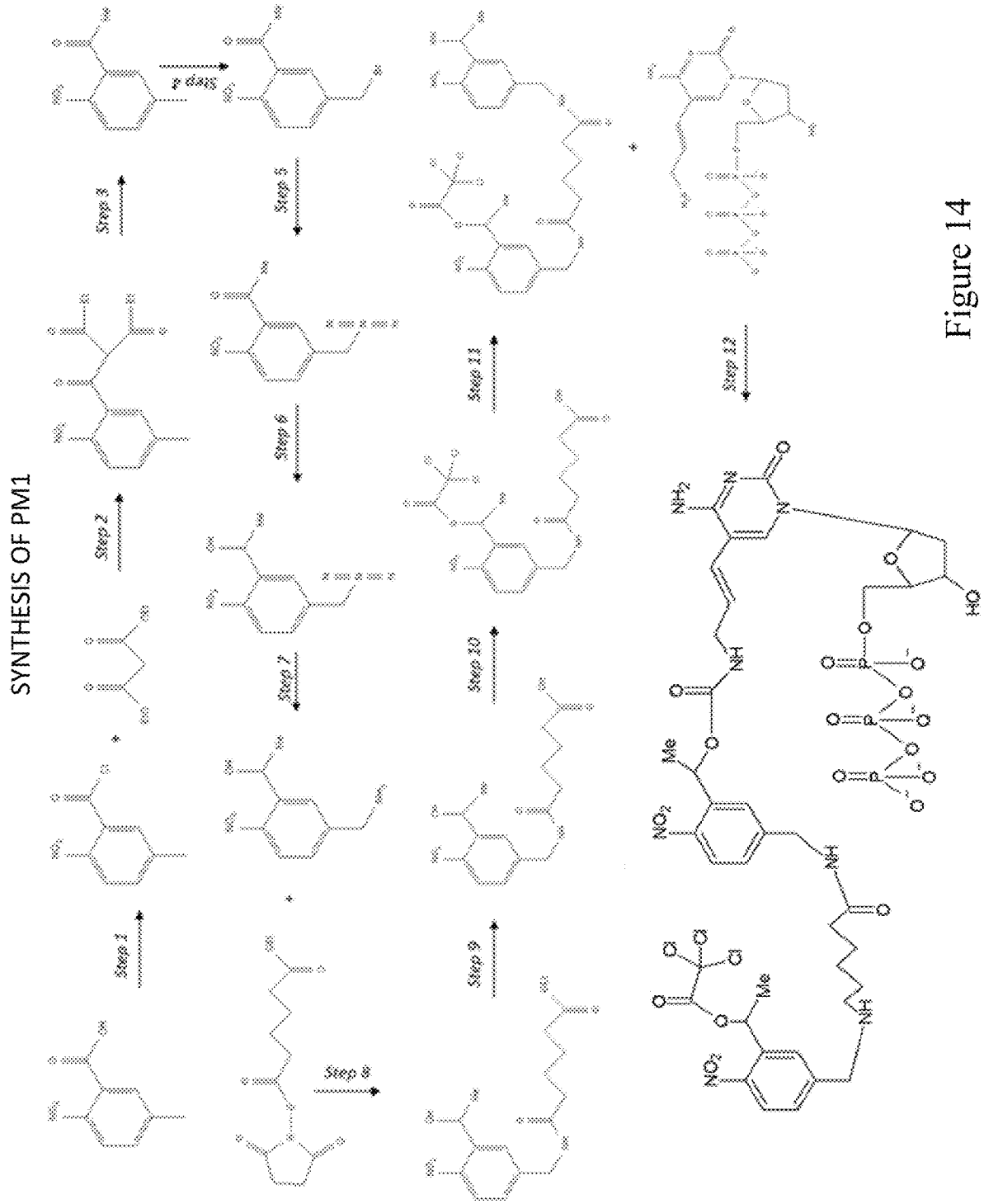
FIG. 14 shows a pathway for synthesis of dCTP-PAG1 (PM1).

We modified dCTP by adding a photoacid generator (PAG1) to generate dCTP-PAG1 (i.e., "Photoactive Molecule 1", or "PM1"). A reaction scheme for the synthesis of PM1 is shown in FIG. 14.

5-Methyl-2-nitrobenzoic acid, Thionyl Chloride, Magnesium turnings, Chlorobenzene, Carbon tetrachloride ($CCl_4$), Diethyl malonate, Sulfuric acid ($H_2SO_4$), Chloroform, Acetic acid (AcOH), Sodium carbonate ($Na_2CO_3$), N-bromosuccinimide, Benzoyl peroxide, Ethyl Acetate (EtOAc), Sodium sulfate ($Na_2SO_4$), Hexane, Methanol, Hydrogen Chloride (HCl), 1,4-dioxane, Sodium borohydride ($NaBH_4$), Tetrahydrofuran (THF), Triphenylphosphine ($PPh_3$), triphosgene, trimethylamine, N-hydroxysuccinimide, potassium hydroxide (KOH), trichloroacetic acid, and sodium bisulfite ($NaHSO_3$) were obtained from Sigma Aldrich. Ethyl Alcohol, methanol, acetonitrile and Acetone were obtained from VWR. 5-Aminoallyl-2'-deoxycytidine-5'-Triphosphate was obtained from Trilink Biotechnologies.

Step 1: 5-Methyl-2-nitrobenzoic acid (27.6 mmol) was added in small portions to thionyl chloride (148 mmol) and the mixture was stirred at room temperature for 12 hours. Excess thionyl chloride was removed by vacuum.

Step 2: Next, a mixture of magnesium turnings (442 mmol), 6 mL absolute ethyl alcohol, 8 mL chlorobenzene, and 0.1 mL $CCl_4$ were refluxed until most of the magnesium reacted. A solution of diethyl malonate (4.82 g) in 10 mL chlorobenzene was added followed by the addition of 5-Methyl-2-nitrobenzoic acid chloride. The reaction was stirred for 1 hour and 1.7 mL $H_2SO_4$ in 17 mL water was added. The mixture was stirred for 20 minutes and 20 mL chloroform was added. The aqueous layer was extracted 3 times with 10 mL chloroform and were combined, dried and evaporated.

Step 3: The residue was dissolved in 8.25 mL AcOH in 5.4 mL water containing 1 mL $H_2SO_4$ and the mixture was refluxed for 6 hours. The mixture was neutralized with aqueous $Na_2CO_3$, extracted 3 times with 20 mL chloroform, dried and concentrated. The residue was re-crystallized from 70% ethyl alcohol and isolated. This mixture is 5-Methyl-2-nitroacetophenone.

Step 4: 5-Bromomethyl-2-nitroacetophenone was obtained by the mixture of 5-Methyl-2-nitroacetophenone (19.6 mmol), N-bromosuccinimide (20.6 mmol) and benzoyl peroxide (0.01 meq) which were refluxed in 20 mL $CCl_4$ for 5 hours. The reaction mixture was filtered, concentrated, recrystallized in $CCl_4$ and isolated.

Step 5: The 5-Bromomethyl-2-nitroacetophenone (7.75 mmol) was dissolved in acetone: $H_2O$ (5:1 by volume, 50 mL). Sodium azide (11.6 mmol) was added, and the mixture was heated to 75° C. overnight in a flask equipped with a reflux condenser. After acetone evaporation under reduced pressure, the aqueous phase was extracted with EtOAc, washed with brine, and dried with $Na_2SO_4$, and the solvent was evaporated under reduced pressure. The mixture was purified by silica gel chromatography using a 10-20% gradient of EtOAc in hexane.

Step 6: The purified mixture from step 5 (6.81 mmol) was dissolved in MeOH: dioxane (3:2 by volume, 30 mL), and NaBH$_4$ (10 mmol) was added slowly. After 30 min, water (50 mL) and 2 M HCl (1 mL) were added and the suspension was extracted twice with EtOAc, washed with brine, dried over Na$_2$SO$_4$, and evaporated under reduced pressure and light protection. The resulting brown oil was purified by silica gel chromatography using a 10-20% gradient of EtOAc in hexane.

Step 7: To a solution of compound (brown oil) from step 6, (4.54 mmol) in THF (30 mL), PPh$_3$ (5 mmol) and H$_2$O (0.5 mL) were added and the mixture was heated at 60° C. for 4 h. Evaporation of the solvent under reduced pressure gave a residue that was dissolved in chloroform and purified by silica gel chromatography with 5-15% MeOH in Chloroform to give the compound 1-(5-(Aminomethyl)-2-nitrophenyl)ethanol.

Step 8: Triphosgene (1 mmol) and triethylamine (10 mmol) were added at 0° C. to the solution of the adipic acid monoethyl ester (2 mmol) in dichloromethane (10 mL). Then N-hydroxysuccinimide (2 mmol) was added to the reaction mixture. The reaction mixture was stirred for 40 min at room temperature. After completion of the reaction, the reaction mixture was filtered by suction filtration. The product was formed by the removal of the filtrate by rotary evaporation followed by short-path silica-gel column chromatography using 20% ethyl acetate in hexane. The solution was mixed with 1-(5-(Aminomethyl)-2-nitrophenyl)ethanol (3 mmol) in DMF (3 mL). The solution was stirred at room temperature overnight and evaporated in vacuum. The residue was dissolved in EtOAc, dried over Na$_2$SO$_4$, and evaporated under reduced pressure.

Step 9: To a stirring solution of the ester (1 equivalent) and methanol (5 mL), KOH (2 molar equivalents) was added at 35° C. The reaction was allowed to continue for 1 hour and then quenched by addition of water (20 mL). The aqueous layer was acidified and the resulting acid was extracted from the aqueous layer by EtOAc.

Step 10: A mixture of Trichloroacetic acid (1.35 mmol), 4% concentrated H$_2$SO$_4$ (2.88 µl) and 1 mL of alcohol (EtOAc containing the resulting acid) from Step 9 were combined in microwave reaction vessel and irradiated for 20 minutes, during which the acid catalyst was loaded every 5 minutes. Once the reaction was complete, the solvent was evaporated under pressure, and the crude residue was dissolved in ethyl acetate. The organic layer was washed with NaHSO$_3$ and dried with anhydrous Na$_2$SO$_4$. The mixture was then purified and concentrated in vacuum to give the ester product.

Step 11: Triphosgene (1 mmol) and triethylamine (10 mmol) were added at 0° C. to a stirred solution of the adipic acid monoethyl ester (2 mmol) in dichloromethane (10 mL). Then N-hydroxysuccinimide (2 mmol) was added to the reaction mixture. The reaction mixture was stirred for 40 min at room temperature. After completion of the reaction, the reaction mixture was filtered by suction filtration. The product was formed by the removal of the filtrate by rotary evaporation followed by short-path silica-gel column chromatography using 20% ethyl acetate in hexane. The solution was mixed with 1-(5-(Aminomethyl)-2-nitrophenyl)ethanol (3 mmol) in DMF (3 mL). The solution was stirred at room temperature overnight and evaporated in vacuum. The residue was dissolved in EtOAc, dried over Na$_2$SO$_4$, and evaporated under reduced pressure.

Step 12: The compound (residue) from step 11 was then dissolved in 2 mL of acetonitrile. DSC (0.75 mmol) dissolved in 3 mL of acetonitrile: ethyl acetate (5:1) solution, was then added, followed by triethylamine (0.75 mmol). 5-Aminoallyl-2'-deoxycytidine-5'-Triphosphate (1 mmol) was then added to this mixture. After overnight reaction, cold diluted HCl was added and the product was extracted with ethyl acetate. The solution was washed three times with diluted HCl, dried over anhydrous sodium sulfate, and the solvent was removed by evaporation.

Example 6: Synthesis of Photoactive Molecule 2 (PM2) (dATP-PAG2)

Figure 15:
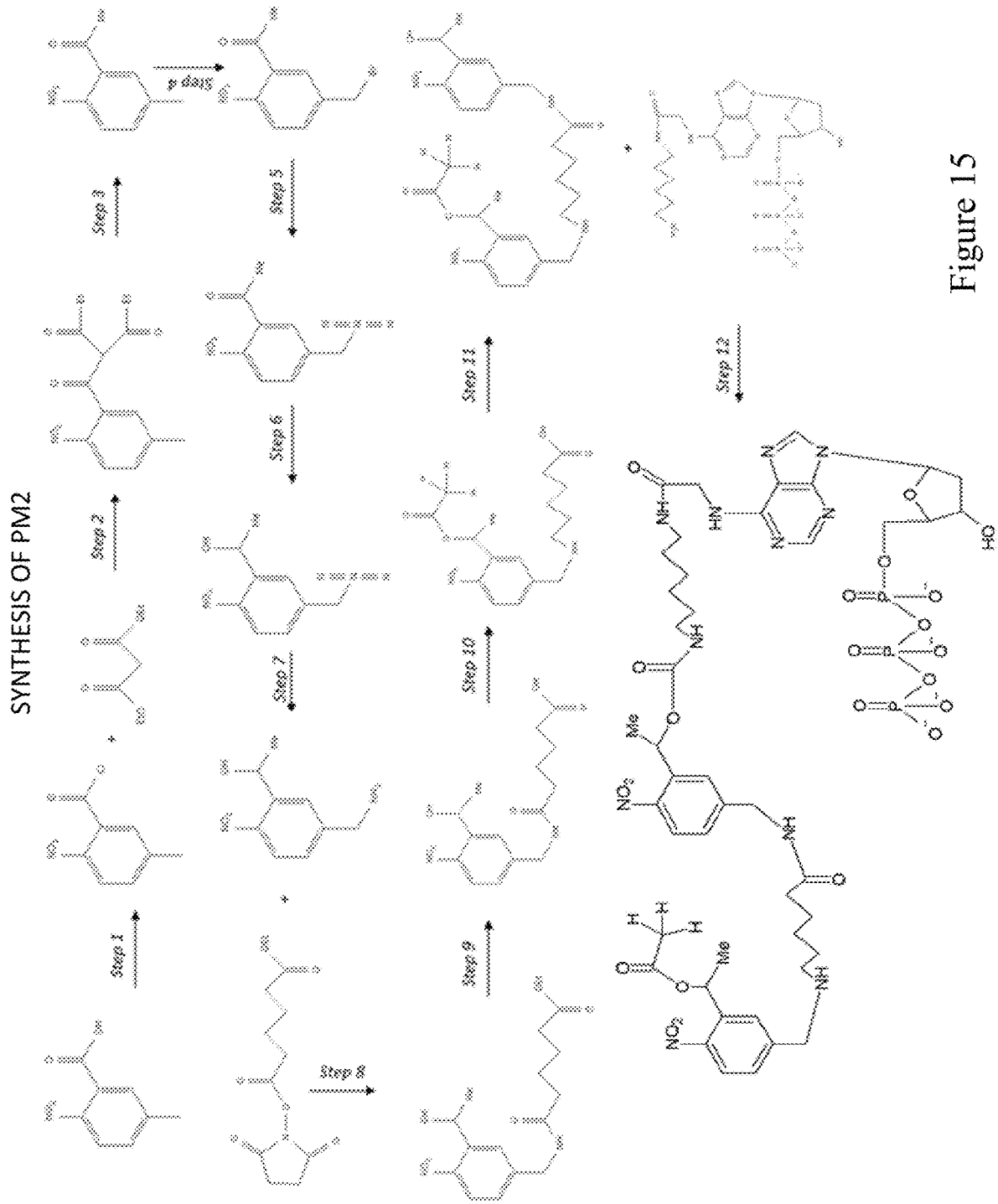
FIG. 15 shows a pathway for synthesis of dATP-PAG2 (PM2).

We modified dATP by adding a photoacid generator (PAG2) to generate dCTP-PAG2 (i.e., "Photoactive Molecule 2" or "PM2"). A reaction scheme for the synthesis of PM2 is shown in FIG. 15. The synthesis was performed as follows:

N6-(6-Amino) hexyl-2'-deoxyadenosine-5'-triphosphate was obtained from Jenabiosciences. Acetic acid was obtained from Sigma Aldrich.

Steps 1 through 9 are repeated as given in Example 5.

Step 10: A mixture of Acetic acid (1.35 mmol), 4% concentrated H$_2$SO$_4$ (2.88 µL) and 1 mL of alcohol (EtOAc containing the resulting acid) from Step 9 were combined in microwave reaction vessel and irradiated for 20 minutes, during which the acid catalyst was loaded every 5 minutes. Once the reaction was complete, the solvent was evaporated under pressure, and the crude residue was dissolved in ethyl acetate. The organic layer was washed with NaHSO$_3$ and dried with anhydrous Na$_2$SO$_4$. The mixture was then purified and concentrated in vacuum to give the ester product.

Step 11 Triphosgene (1 mmol) and triethylamine (10 mmol) were added at 0° C. to the stirred solution from Step 9 (2 mmol) in dichloromethane (10 mL). Then N-hydroxysuccinimide (2 mmol) was added to the reaction mixture. The reaction mixture was stirred for 40 min at room temperature. After completion of the reaction, the reaction mixture was filtered by suction filtration. The product was formed by the removal of the filtrate by rotary evaporation followed by short-path silica-gel column chromatography using 20% ethyl acetate in hexane. The solution was mixed with 1-(5-(Aminomethyl)-2-nitrophenyl)ethanol (3 mmol) in DMF (3 mL). The solution was stirred at room temperature overnight and evaporated in vacuum. The residue was dissolved in EtOAc, dried over Na$_2$SO$_4$, and evaporated under reduced pressure.

Step 12: The resulting compound from Step 11 was dissolved in 2 mL of acetonitrile. DSC (0.75 mmol) dissolved in 3 mL of acetonitrile: ethyl acetate (5:1) solution, was then added, followed by triethylamine (0.75 mmol). N6-(6-Amino) hexyl-2'-deoxyadenosine-5'-triphosphate (1 mmol) was then added to this mixture. After overnight reaction, cold diluted HCl was added and the product was extracted with ethyl acetate. The solution was washed three times with diluted HCl, dried over anhydrous sodium sulfate, and the solvent was removed by evaporation.

Example 7: Synthesis of Photoactive Molecule 3 (PM3) (dUTP-PBG1)

Figure 16:
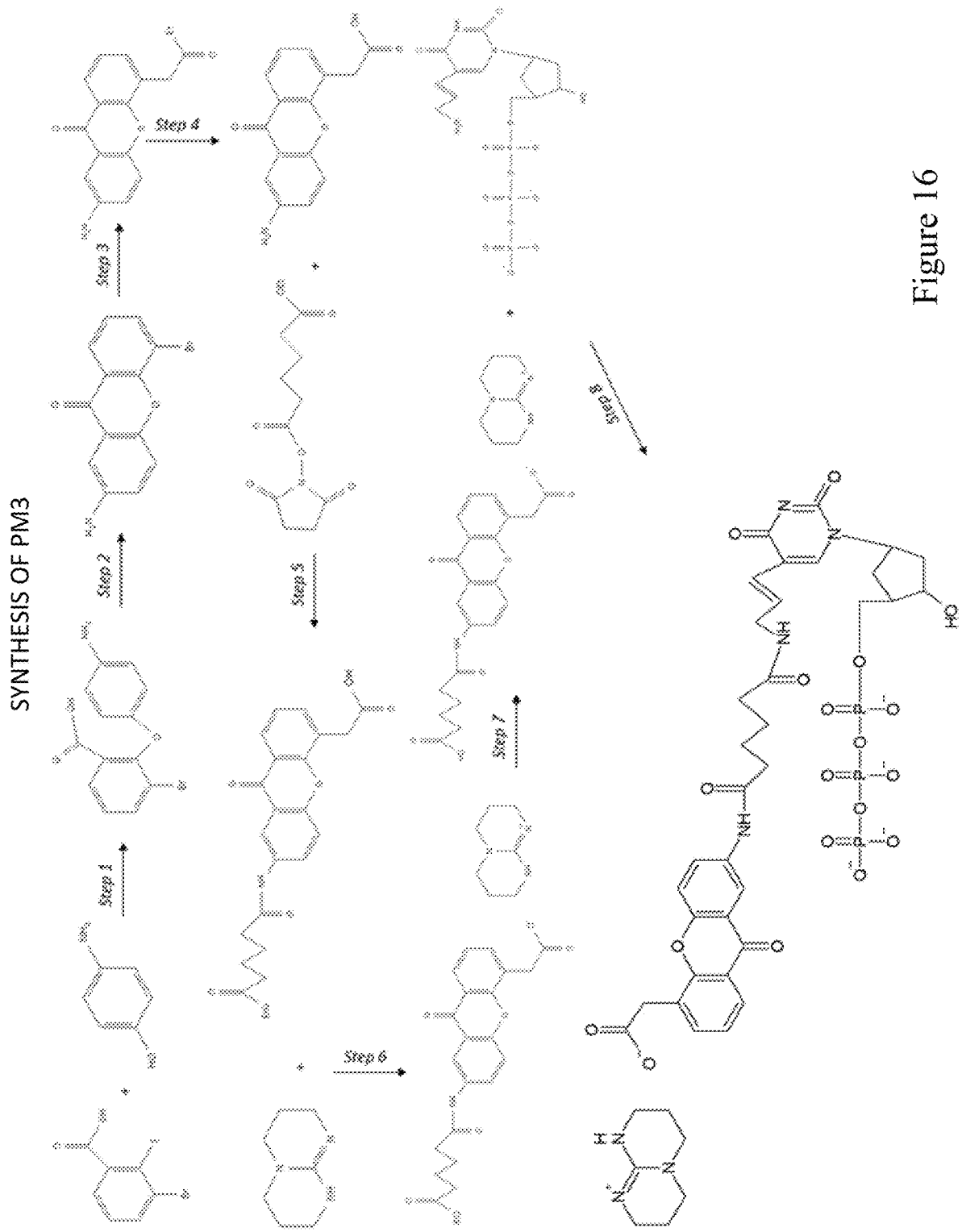
FIG. 16 shows a pathway for synthesis of dUTP-PBG1 (PM3).

We modified dUTP by adding a photobase generator (PBG1) to generate dUTP-PBG1 (i.e., "Photoactive Molecule 3" or "PM3"). A reaction scheme for the synthesis of PM3 is shown in FIG. 16. The synthesis was performed as follows:

3-bromo-2-iodo benzoic acid, sodium, 4-aminophenol, dimethyl sulfoxide, then tris (2-(2-methoxyethoxy) ethyl) amine, copper chloride (CuCl), 1,3-Bis(2,6-diisopropylphenyl)imidazolium chloride, Palladium(II) acetate (Pd(OAc)$_2$), Cesium carbonate (Cs$_2$CO$_3$), diethyl malonate, dioxane, Triazabicyclodecene, diisopropyl ether, and N-(3-Dimethylaminopropyl)-N'-ethylcarbodiimide hydrochloride were obtained from Sigma Aldrich. 5-Aminoallyl-dUTP was obtained from Biotium.

Step 1: 3-bromo-2-iodo benzoic acid (8 mmol) was dissolved in a KOH solution (9.5 mmol). The mixture was condensed under vacuum at 100° C. and the resultant solid was heated under vacuum at 100° C. for 12 h to yield a dried potassium salt. Metallic sodium (8.35 mmol) was dissolved in 100 mL of methanol, and 4-aminophenol (8.35 mmol) was added. The mixture was condensed and heated under vacuum at 100° C. for 12 h to yield a dried sodium salt. The sodium salt was dissolved in 15 mL of anhydrous dimethyl sulfoxide, and then tris (2-(2-methoxyethoxy) ethyl)amine (TDA-1, 1.0 mL) was added. The mixture was stirred to reach homogeneity at room temperature under anhydrous conditions, and then CuCl (350 mg) and potassium salt powders of the compound were added. The resultant mixture was stirred at 85° C. for 4 h, cooled down to room temperature, washed with a NaOH, filtered with diatomite, and acidified with 1 N HCl to pH value at 2-3. A semisolid precipitate was collected, washed with water, and dried to yield a crude product.

Step 2: The crude product from Step 1 (7.35 mmol) was added to a stirring sulfuric acid solution. The mixture was allowed to react for 30 min at 90° C., and then cooled down to room temperature, diluted with 200 mL of ice water, and filtered. The resultant solid was washed with water, dried, and recrystallized from EtOAc/Methanol to yield a light yellow solid.

Step 3: The light yellow solid from from Step 2 (7.25 mmol), 1, 3-bi-(2,6-diisopropylphenyl)imidazole chloride (Ipr. HCl 2% by mole), Pd(OAc)2 (2% by mole), Cs$_2$CO$_3$ (4.7 g, 14.5 mmol), diethyl malonate (1.16 g, 7.25 mmol), and 20 mL of dioxane were mixed. The mixture was allowed to react at 80° C. for 24 h, and then cooled down to room temperature, diluted with 100 mL of EtOAc, and filtered to yield a black precipitate. The filtrate was condensed and recrystallized from EtOAc/MeOH to yield a light yellow solid.

Step 4: The light yellow solid from Step 3 (0.3 mol), 350 mL of methanol, and a NaOH solution (0.6 mol) were mixed. The mixture was heated, stirred at 40° C., hydrolyzed completely, acidified with acetic acid to yield a white precipitate, filtered, and dried to yield a crude product.

Step 5: Triphosgene (1 mmol) and triethylamine (10 mmol) were added at 0° C. to a stirred solution of the adipic acid monoethyl ester (2 mmol) in dichloromethane (10 mL). Then N-hydroxysuccinimide (2 mmol) was added to the reaction mixture. The reaction mixture was stirred for 40 min at room temperature. After completion of the reaction, the reaction mixture was filtered by suction filtration. The product was formed by the removal of the filtrate by rotary evaporation followed by short-path silica-gel column chromatography using 20% ethyl acetate in hexane. The solution was mixed with Step 5 compound (3 mmol) in DMF (3 mL). The solution was stirred at room temperature overnight and evaporated in vacuum. The residue was dissolved in EtOAc, dried over Na$_2$SO$_4$, and evaporated under reduced pressure.

Step 6: 10 mmol of Triazabicyclodecene and 10 mmol of the compound obtained in Step 5 were dissolved into 20 mL of acetone, and stirred at room temperature for 30 minutes. After completion of the reaction, reaction solution was concentrated under reduced pressure, and the resulting residue was washed with diisopropyl ether, and then dried under reduced pressure.

Step 7: To a stirring solution of the ester from Step 6 (1 equivalent) and methanol (5 mL), KOH (2 molar equivalents) was added at 35° C. The reaction was allowed to continue for 1 hour and then quenched by addition of water (20 mL). The aqueous layer was acidified and the resulting acid was extracted from the aqueous layer by EtOAc.

Step 8: 2 mmol of the compound from Step 7 is mixed along with EDC (8 mmol) and N-hydroxysuccinimide (2 mmol) and the reaction mixture was stirred for 40 min at room temperature. The product was formed by the removal of the filtrate by rotary evaporation followed by short-path silica-gel column chromatography using 20% ethyl acetate in hexane. The solution was mixed with 5-Aminoallyl-dUTP (3 mmol) in DMF (3 mL). The solution was stirred at room temperature overnight and evaporated in vacuum. The residue was dissolved in EtOAc, dried over Na$_2$SO$_4$, and evaporated under reduced pressure.

Example 8: Synthesis of Photoactive Molecule 4 (PM4) (dGTP-PBG2)

Figure 17:
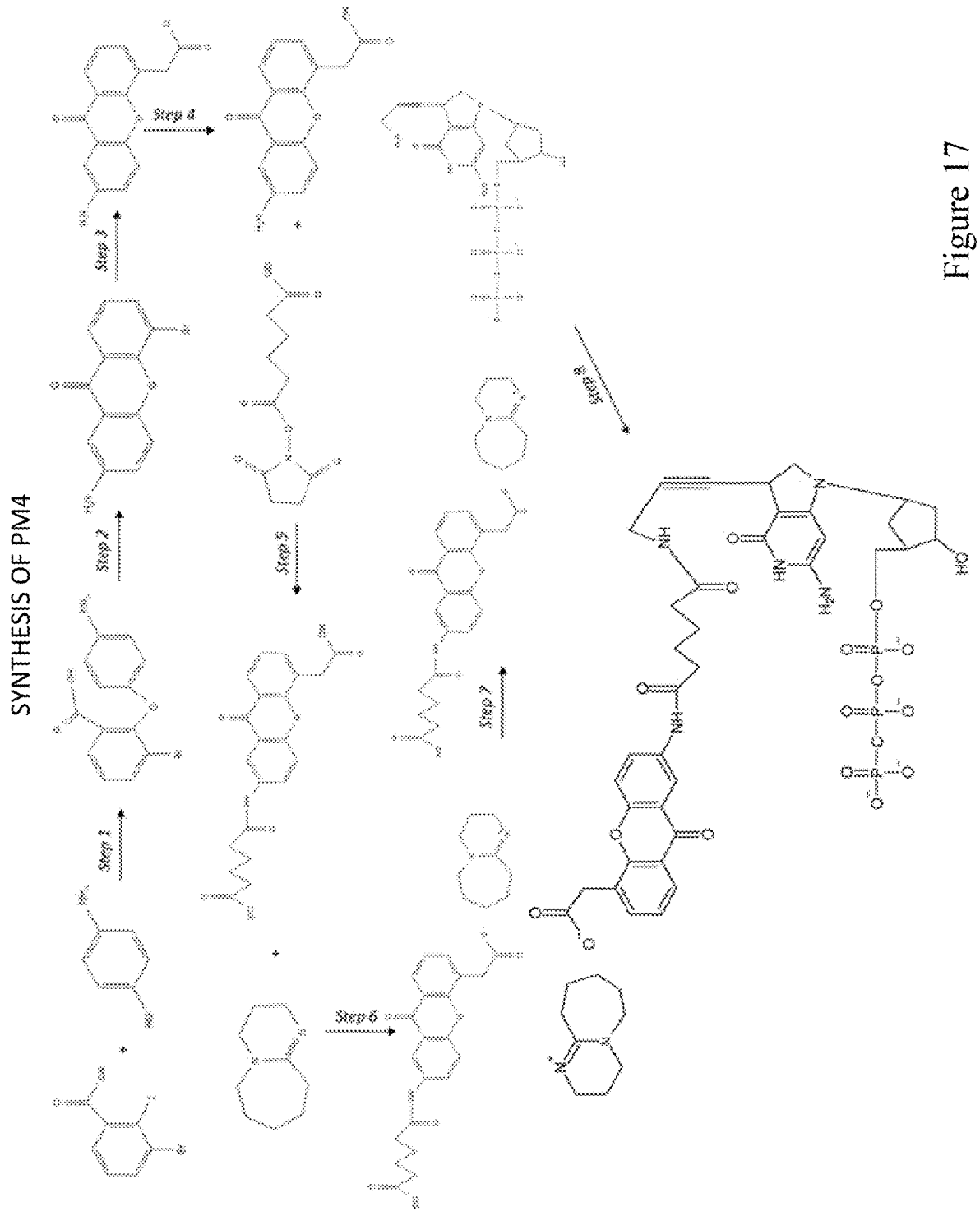
FIG. 17 shows a pathway for synthesis of dGTP-PBG2 (PM4).
Figure 19A:
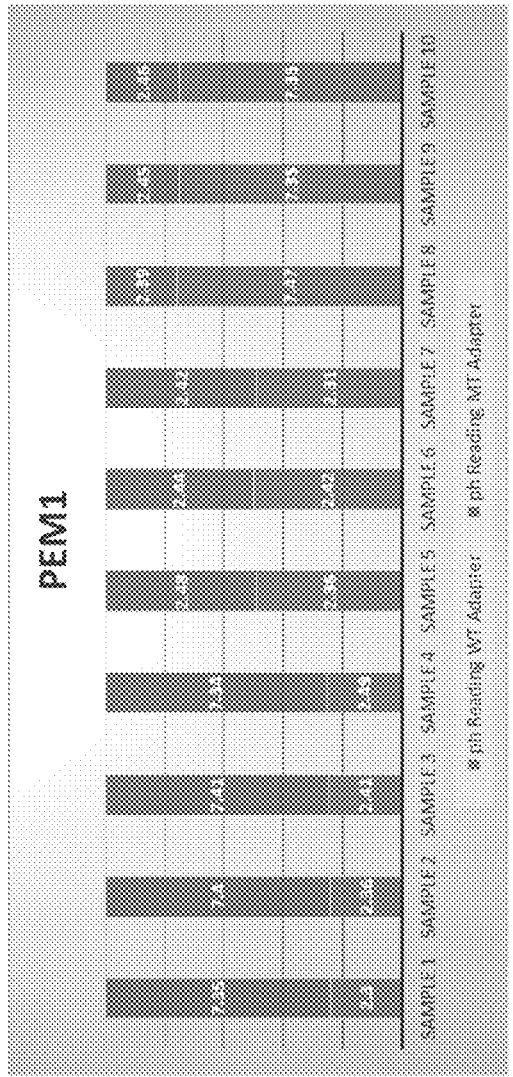
FIGS. 19A, 19B, 19C and 19D show a graph of results of an assay to detect incorporation of each of the four modified nucleotides into a sequence.
Figure 19B:
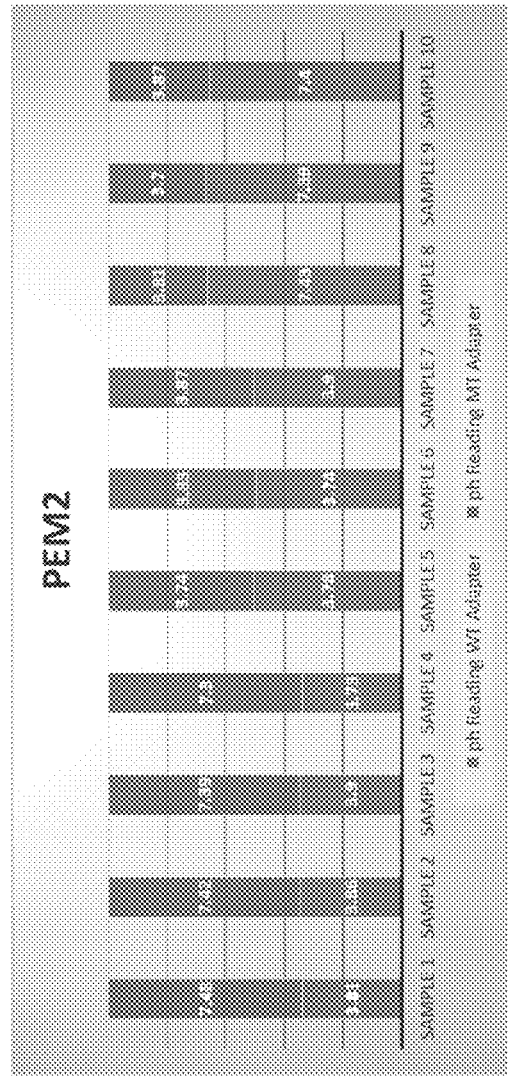
Figure 19C:
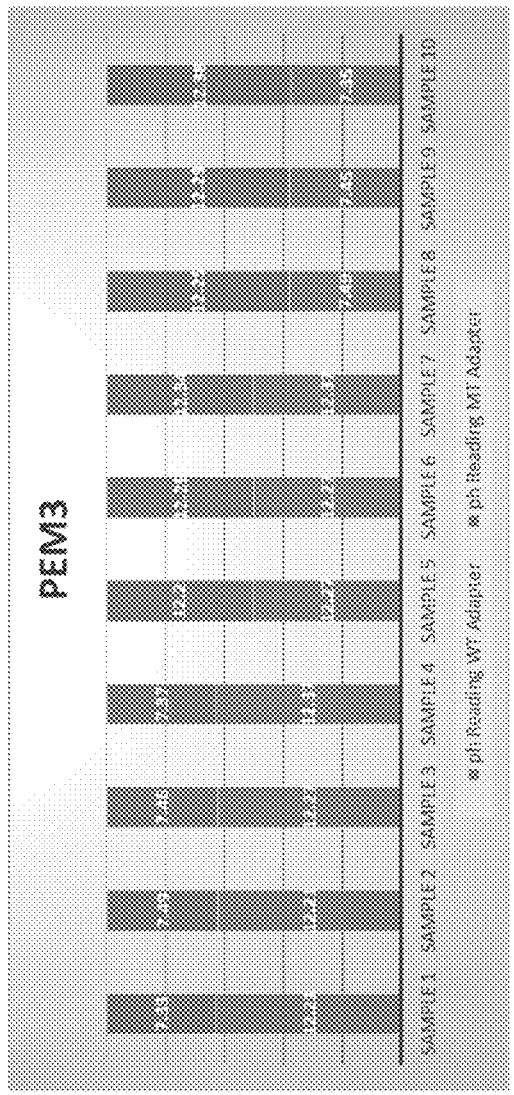
Figure 19D:
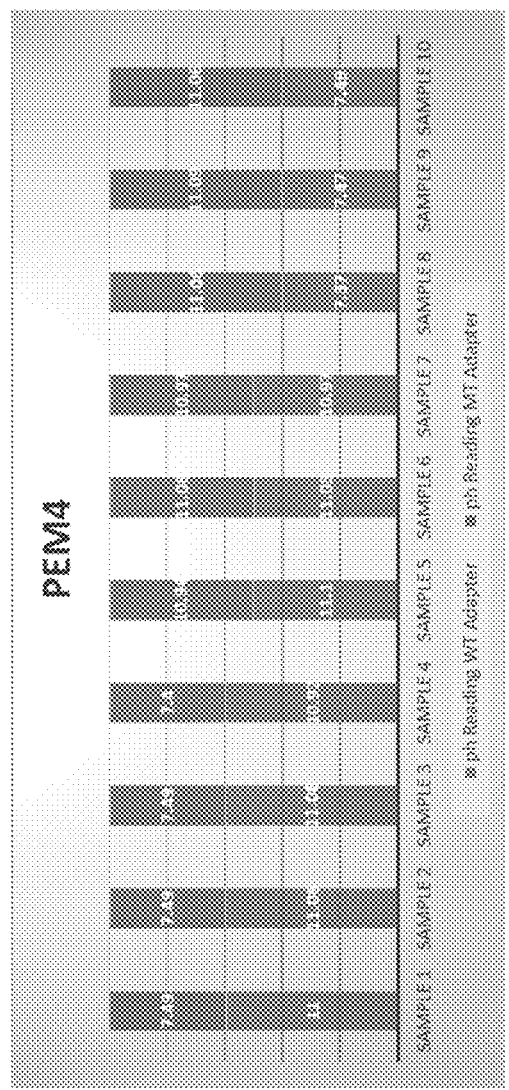

We modified dGTP by adding a photobase generator (PBG2) to generate dUTP-PBG2 (i.e., "Photoactive Molecule 4" or "PM4"). A reaction scheme for the synthesis of PM4 is shown in FIG. 17. The synthesis was performed as follows:

1,8-Diazabicyclo[5.4.0]undec-7-ene was obtained from Sigma Aldrich. 7-Deaza-7-Propargylamino-2'-deoxyguanosine-5'-Triphosphate was obtained from Trilink Biotechnologies.

Steps 1 through 5 are repeated as given in Example 7.

Step 6: 10 mmol of 1,8-Diazabicyclo[5.4.0]undec-7-ene and 10 mmol of the compound obtained in Step 5 were dissolved into 20 mL of acetone, and stirred at room temperature for 30 minutes. After completion of the reaction, reaction solution was concentrated under reduced pressure, and the resulting residue was washed with diisopropyl ether, and then dried under reduced pressure.

Step 7: To a stirring solution of the ester from Step 6 (1 equivalent) and methanol (5 mL), KOH (2 molar equivalents) was added at 35 C. The reaction was allowed to continue for 1 hour and then quenched by addition of water (20 mL). The aqueous layer was acidified and the resulting acid was extracted from the aqueous layer by EtOAc.

Step 8: 2 mmol of the compound from Step 7 is mixed along with EDC (8 mmol) and N-hydroxysuccinimide (2 mmol) and the reaction mixture was stirred for 40 min at room temperature. The product was formed by the removal of the filtrate by rotary evaporation followed by short-path silica-gel column chromatography using 20% ethyl acetate in hexane. The solution was mixed with 7-Deaza-7-Propargylamino-2'-deoxyguanosine-5'-Triphosphate (3 mmol) in DMF (3 mL). The solution was stirred at room temperature overnight and evaporated in vacuum. The residue was dissolved in EtOAc, dried over Na$_2$SO$_4$, and evaporated under reduced pressure.

Example 9: Testing of Performance of Photoactive Molecules

Photoactive molecules PM1-PM4 were tested for their performance in Polymerase Chain Reactions (PCR) and specifically genotyping application on the methylenetetrahydrofolate reductase (MTHFR) gene. The nucleotide polymorphism 677 C>T (rs1801133) is located within the region coding for the catalytic domain of MTHFR and results in an amino acid substitution from an alanine to a valine at codon position 222 (exon 4).

PNA sequences were synthesized on a Silicon wafer containing a microarray of sequences to be used as 'adapters' for allele specific primer extension reactions. Genomic DNA samples were obtained in-house from the Vibrant Genomics Labs and the mutations of 677 C>T were known through ACGT, Inc. sequencing.

To amplify the region in the genomic DNA, PCR was performed in a 20 µL reaction volume as follows: 50 ng of the human genomic DNA was added to a PCR amplification reagent mixture comprising: 2.5 units of Titanium Taq DNA polymerase (Clontech), 200 µM each dNTP (dATP, dTTP, dGTP, dCTP) (Thermofisher Scientific), 10× PCR Buffer with 1.5 mM MgCl2 (Thermofisher Scientific), 20 pmol sense primer (5'-CCTATTGGCAGGTTACCCCA-3') (SEQ ID NO: 22) (IDT), and 20 pmol antisense primer (5'-GGCAAGTGATGCCCATGTCG-3') (SEQ ID NO: 23) (IDT). The PCR reaction mixture was then pre-denatured at 94° C. for 5 minutes, followed by 35 cycles of amplification, each cycle comprising 1) denaturation at 94° C. for 30 seconds, 2) annealing at 54° C. for 30 seconds, and 3) extension at 72° C. for 45 seconds. A final extension step at 72° C. for 10 minutes was performed.

Primer extension mixes were prepared using extension primers specific to alleles. In this particular assay, ATGGCTAG-GAAGGTGTCTGCGGGAGC (SEQ ID NO: 1) and CGCGATTG-GAAGGTGTCTGCGGGAGT (SEQ ID NO: 2) (IDT) were used and represented as Adapter-Primer with the former being the primer specific to Wild-Type allele ('C') and the latter being the primer specific to the Mutant-Type allele ('T') of the MTHFR gene. The microarray contains sequences complimentary to the above adapters to detect the performance of individual primers.

To test the performance of individual photoactive molecules, 4 different primer extension mixes were used. Primer Extension Mix 1 (PEM1) comprised of 20 µL reaction volume with 2.5 units of Titanium Taq DNA polymerase, 50 µM each dNTP (dATP, dTTP, dGTP, dCTP) and 10 µM of PM1, 10×PCR Buffer with 1.5 mM MgCl2 (Thermofisher Scientific), and 20 pmol primer extension mix containing primers for both wild-type (SEQ ID NO: 1) and mutant-type (SEQ ID NO: 2) allele specific primers.

Primer Extension Mix 2 (PEM2) comprised of 20 µL reaction volume with 2.5 units of Titanium Taq DNA polymerase, 50 µM each dNTP (dATP, dTTP, dGTP, dCTP) and 10 µM of PM2, 10×PCR Buffer with 1.5 mM MgCl2 (Thermofisher Scientific), 20 pmol primer extension mix containing primers for both wild-type (SEQ ID NO: 1) and mutant-type (SEQ ID NO: 2) allele specific primers.

Primer Extension Mix 3 (PEM3) comprised of 20 µL reaction volume with 2.5 units of Titanium Taq DNA polymerase, 50 µM each dNTP (dATP, dTTP, dGTP, dCTP) and 10 µM of PM3, 10×PCR Buffer with 1.5 mM MgCl2 (Thermofisher Scientific), 20 pmol primer extension mix containing primers for both wild-type (SEQ ID NO: 1) and mutant-type (SEQ ID NO: 2) allele specific primers.

Primer Extension Mix 4 (PEM4) comprised of 20 µL reaction volume with 2.5 units of Titanium Taq DNA polymerase, 50 µM each dNTP (dATP, dTTP, dGTP, dCTP) and 10 µM of PM4, 10×PCR Buffer with 1.5 mM MgCl2 (Thermofisher Scientific), 20 pmol primer extension mix containing primers for both wild-type (SEQ ID NO: 1) and mutant-type (SEQ ID NO: 2) allele specific primers.

Primer Extension reaction was done by adding 20 nt of primer extension mix to the amplified reaction mix and performed 40 cycles of PCR, with a pre-denaturation at 94° C. for 5 minutes and each cycle comprising of denaturation at 94° C. for 30 seconds, annealing/extension at 54° C. for 30 seconds, were carried out, followed by a final post-denaturation at 94° C. for 5 minutes.

After the completion of primer extension reaction, 60 µl of hybridization buffer (1×PBS buffer with 1% fish gelatin and 0.1 mg/mL salmon sperm DNA) was added and the pillar plate was kept in a hybridization chamber at 45° C. for 2 hours. This was followed by 2 wash steps of PBS with the first wash being at 39° C. for 5 minutes followed by a wash at room temperature for 10 minutes. The chips were then rinsed with DI water and dried under a stream of nitrogen.

The chips were then exposed using 365 nm bulb stratalinker for 15 minutes and mixed with 30 µl of DI water. Lastly, the pH of the solution was read using an ISFET pH sensor (Sentron). The results obtained are shown in FIGS. 18, 19A, 19B, 19C and 19D.

Example 10: Synthesis of Photoactive Molecule 5 (PM5) (ddCTP-PAG1)

Figure 20:
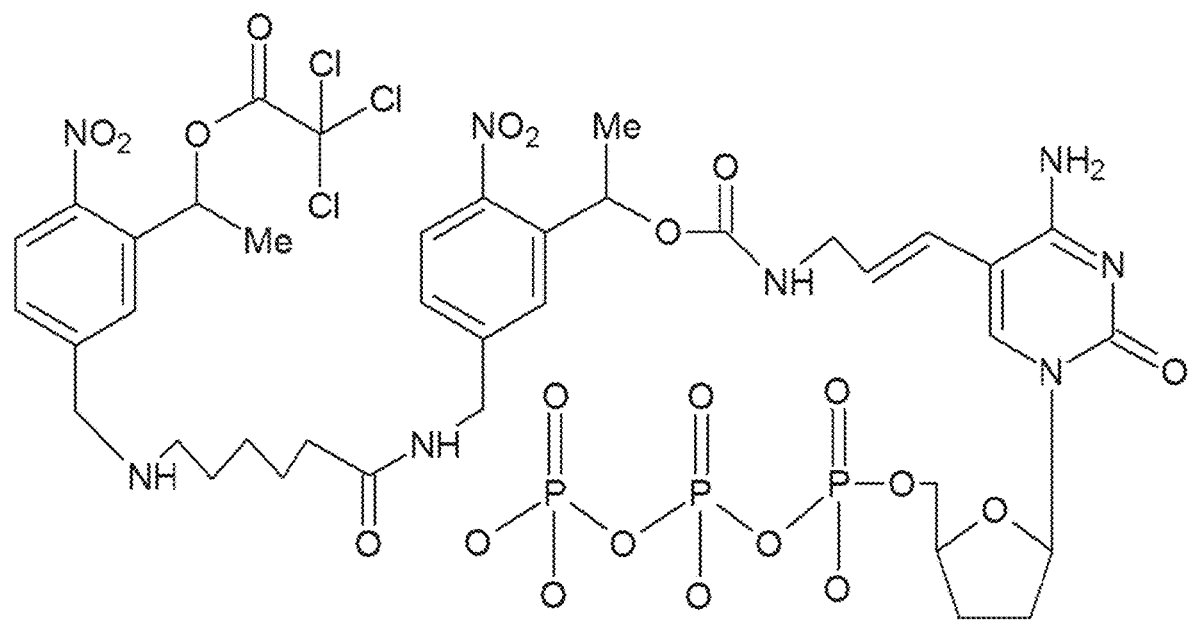
FIG. 20 shows the structure of modified nucleotide ddCTP-PAG1 (PM5).

Photoactive molecule PM5 is synthesized as given in Example 5. dCTP is replaced by ddCTP in this molecule. The structure of PM5 is shown in FIG. 20.

Example 11: Synthesis of Photoactive Molecule 6 (PM6) (ddATP-PAG2)

Figure 21:
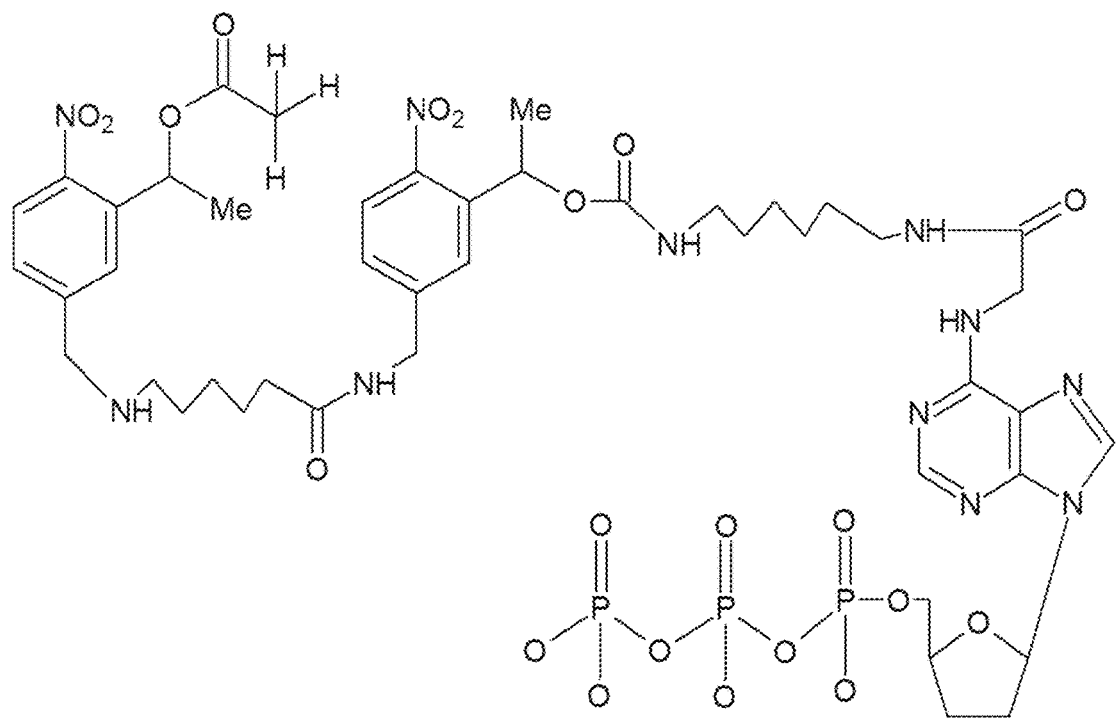
FIG. 21 shows the structure of modified nucleotide ddATP-PAG2 (PM6).

Photoactive molecule PM6 is synthesized as given in Example 6. dATP is replaced by ddATP in this molecule. The structure of PM6 is shown in FIG. 21.

Example 12: Synthesis of Photoactive Molecule 7 (PM7) (ddUTP-PBG1)

Figure 22:
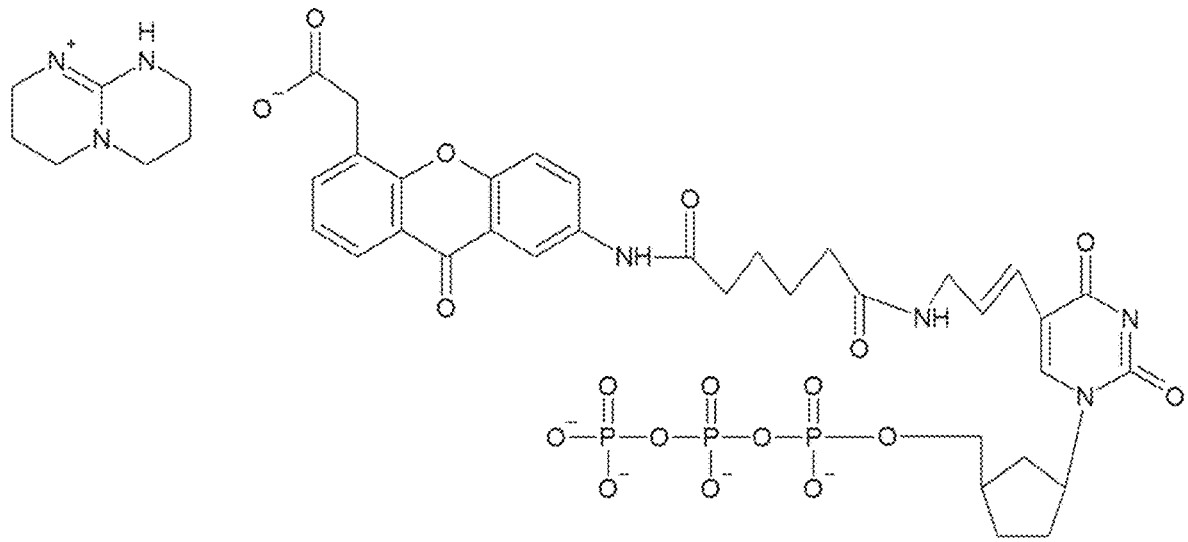
FIG. 22 shows the structure of modified nucleotide ddUTP-PBG1 (PM7).

Photoactive molecule PM7 is synthesized as given in Example 7. dUTP is replaced by ddUTP in this molecule. The structure of PM7 is shown in FIG. 22.

Example 13: Synthesis of Photoactive Molecule 8 (PM8) (ddGTP-PBG2)

Figure 23:
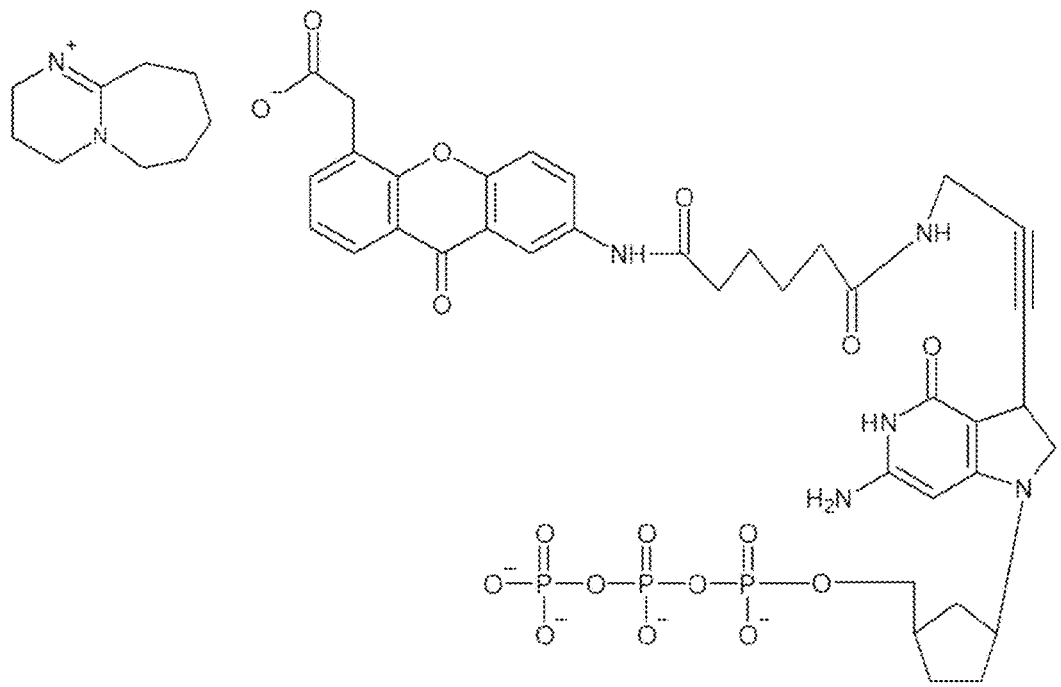
FIG. 23 shows the structure of modified nucleotide ddGTP-PBG2 (PM8).

Photoactive molecule PM8 is synthesized as given in Example 8. dGTP is replaced by ddGTP in this molecule. The structure of PM8 is shown in FIG. 23.

Example 14: Testing the Performance of Photoactive Molecules (HM 5-8)

Photoactive molecules were tested for their performance in Polymerase Chain Reactions (PCR) and specifically genotyping application on the methylenetetrahydrofolate reductase (MTHFR) and 9p21 gene. The nucleotide polymorphism 677 C>T (rs1801133) is located within the region coding for the catalytic domain of MTHFR and results in an amino acid substitution from an alanine to a valine at codon position 222 (exon 4). The polymorphism rs10757274 (A;G) is a SNP located in chromosomal region 9p21.

Genotyping of MTHFR and 9p21 regions, with the well-known mutations, rs1801133 and rs10757274, were tested using 20 DNA samples. The DNA samples had a known genotyping result which were determined using Real-Time PCR. 34-mer length PNA-DNA chimera primer sequences 5'-CTGAAGCACTTGAAGGAGAAGGTGTCTGCGG (GAG)-3' (SEQ ID NO: 16) for the rs1801133 mutation and 5'-CTCC CCCGTGGGTCAAATCTAAGC TGAGTG (TTG)-3' (SEQ ID NO: 24) for the rs10757274 mutation were synthesized according to the methods given above.

DNA were extracted from the samples (buccal swabs) using methods known to one skilled in the art. A standard PCR reaction using forward and reverse primers was performed on the extracted DNA samples. Hybridization and polymerase extension on each of chips were performed as follows. The PCR product was mixed in 1×DNA Polymerase Buffer (Clontech), 20 nmol of $MgCl_2$, 1 unit Titanium Taq DNA Polymerase (Clontech), and all 4 photoactive molecules (PM5, PM6, PM7, PM8) (each 20 pmoles). Hybridization is done in a hybridization chamber at 55° C. for 30 minutes followed by washing the chips in 0.1× Ssarc buffer 40° C. for 5 minutes twice followed by rinsing in DI Water. The chips were then exposed using 365 nm bulb strata-linker for 15 minutes and mixed with 30 µl of DI water. Lastly, the pH of the solution was read using an ISFET pH sensor (Sentron). The results obtained are shown in FIGS. 24A and 24B.

Example 15: Synthesis of Anti-p53 Bound to PBG1

3-bromo-2-iodo benzoic acid, sodium, 4-aminophenol, dimethyl sulfoxide, then tris (2-(2-methoxyethoxy) ethyl) amine, copper chloride (CuCl), 1,3-Bis(2,6-diisopropylphenyl)imidazolium chloride, Palladium(II) acetate (Pd(OAc) 2), Cesium carbonate (Cs2CO3), diethyl malonate, dioxane, Triazabicyclodecene, diisopropyl ether, and N-(3-Dimethylaminopropyl)-N'-ethylcarbodiimide hydrochloride were obtained from Sigma Aldrich.

Step 1: 3-bromo-2-iodo benzoic acid (8 mmol) was dissolved in a KOH solution (9.5 mmol). The mixture was condensed under vacuum at 100° C. and the resultant solid was heated under vacuum at 100° C. for 12 h to yield a dried potassium salt. Metallic sodium (8.35 mmol) was dissolved in 100 mL of methanol, and 4-aminophenol (8.35 mmol) was added. The mixture was condensed and heated under vacuum at 100° C. for 12 h to yield a dried sodium salt. The sodium salt was dissolved in 15 mL of anhydrous dimethyl sulfoxide, and then tris (2-(2-methoxyethoxy) ethyl)amine (TDA-1, 1.0 mL) was added. The mixture was stirred to reach homogeneity at room temperature under anhydrous conditions, and then CuCl (350 mg) and potassium salt powders of the compound were added. The resultant mixture was stirred at 85° C. for 4 h, cooled down to room temperature, washed with a NaOH, filtered with diatomite, and acidified with 1 N HCl to pH value at 2-3. A semisolid precipitate was collected, washed with water, and dried to yield a crude product.

Step 2: The crude product from Step 1 (7.35 mmol) was added to a stirring sulfuric acid solution. The mixture was allowed to react for 30 min at 90° C., and then cooled down to room temperature, diluted with 200 mL of ice water, and filtered. The resultant solid was washed with water, dried, and recrystallized from EtOAc/Methanol to yield a light yellow solid.

Step 3: The compound from Step 2 (7.25 mmol), 1, 3-bi-(2,6-diisopropylphenyl)imidazole chloride (Ipr. HCl 2% by mole), Pd(OAc)2 (2% by mole), Cs2CO3 (4.7 g, 14.5 mmol), diethyl malonate (1.16 g, 7.25 mmol), and 20 mL of dioxane were mixed. The mixture was allowed to react at 80° C. for 24 h, and then cooled down to room temperature, diluted with 100 mL of EtOAc, and filtered to yield a black precipitate. The filtrate was condensed and recrystallized from EtOAc/MeOH to yield a light yellow solid.

Step 4: The compound from Step 3 (0.3 mol), 350 mL of methanol, and a NaOH solution (0.6 mol) were mixed. The mixture was heated, stirred at 40° C., hydrolyzed completely, acidified with acetic acid to yield a white precipitate, filtered, and dried to yield a crude product.

Step 5: Triphosgene (1 mmol) and triethylamine (10 mmol) were added at OC to a stirred solution of the adipic acid monoethyl ester (2 mmol) in dichloromethane (10 ml). Then N-hydroxysuccinimide (2 mmol) was added to the reaction mixture. The reaction mixture was stirred for 40 min at room temperature. After completion of the reaction, the reaction mixture was filtered by suction filtration. The product was formed by the removal of the filtrate by rotary evaporation followed by short-path silica-gel column chromatography using 20% ethyl acetate in hexane. The solution was mixed with Step 5 compound (3 mmol) in DMF (3 ml). The solution was stirred at room temperature overnight and evaporated in vacuum. The residue was dissolved in EtOAc, dried over Na2SO4, and evaporated under reduced pressure.

Step 6: 10 mmol of Triazabicyclodecene and 10 mmol of the compound obtained in Step 5 were dissolved into 20 mL of acetone, and stirred at room temperature for 30 minutes. After completion of the reaction, reaction solution was concentrated under reduced pressure, and the resulting residue was washed with diisopropyl ether, and then dried under reduced pressure.

Step 7: To a stirring solution of the ester from Step 6 (1 equivalent) and methanol (5 mL), KOH (2 molar equivalents) was added at 35 C. The reaction was allowed to continue for 1 hour and then quenched by addition of water (20 mL). The aqueous layer was acidified and the resulting acid was extracted from the aqueous layer by EtOAc.

Step 8: 2 mmol of the compound from Step 7 is mixed along with EDC (8 mmol) and N-hydroxysuccinimide (2 mmol) and the reaction mixture was stirred for 40 min at room temperature. The product was formed by the removal of the filtrate by rotary evaporation followed by short-path silica-gel column chromatography using 20% ethyl acetate in hexane.

Step 9: The solution was mixed with Anti-p53 antibody (3 mmol) in water (3 ml). The reaction was carried out at room temperature overnight and purified using a spin column.

Example 16: Testing Detection of the Photoactive Molecule Anti-p53 Bound to PBG1

Wafers with COOH are prepared as described previously. 4 weight % for 1-ethyl-3-(3-dimethylaminopropyl) carbodiimide and 2 weight % for N-Hydroxysuccinimide (NHS) were added in 94 weight % DI water as reagents to activate the COOH substrate. Wafer substrate is activated by spinning the wafer with this reagent wash solution and then washed away with water.

All Fmoc based amino acids required for p53 validation on the wafer are obtained from Anaspec. The amino acids obtained are Leucine (Leu), Lysine (Lys), Tryptophan (Trp), Aspartic Acid (Asp), Serine (Ser), Phenylalanine (Phe), Threonine (Thr), Glutamic acid (Glu), Glutamine (Gln), Arginine (Arg) and Histidine (His). Ethanolamine is obtained from Sigma Aldrich.

Validation of the wafer by p53 coupling is done by coupling 2 sequences—natural and mutated sequence for p53 antibody. The natural sequence grown is Leu-Lys-Trp-Leu-Asp-Ser-Phe-Thr-Glu-Gln (SEQ ID NO: 25) and mutated sequence grown is Leu-Lys-Trp-Leu-Arg-His-Phe-Thr-Glu-Gln (SEQ ID NO: 26).

Amino acid coupling is done as follows—A Photobase coupling solution containing a polymer, amino acid and photobase is spin coated onto a wafer at 3000 rpm and baked at 65 c for 1 min. in a hot plate. Now the wafer is exposed using a reticle at 80 mj/cm2. and then hard baked at 85 c for 90 sec in a hot plate. Fmoc is deprotected only in the region where it is exposed and the amino acid is coupled simultaneously.

1M Ethanolamine is used for capping the activated COOH which have not been coupled. This is done by spin coating a mixture of polymer+1M Ethanolamine+DI Water and baked at 65 C for 90 secs. Wafer is then stripped with Acetone and IPA and the same process is repeated for coupling the next layer of amino acid.

Natural sequence starts with coupling Leu and is completed by coupling Gln. This sequence is grown on the wafer using a specific mask. Another independent mask is used to grow the mutated sequence similarly. The wafer is diced into chips and bioassay is done to verify p53 sequence assay sensitivity comparing 2 methods of detection. The first method is using fluorescence and the second method is using pH sensing.

Anti-p53 Antibody and Atto 488 Goat ani-mouse IgG are obtained from ABCAM. TBS Buffer, PBST Buffer and BSA are obtained from VWR. The bioassay process is done as follows:

Fluorescence detection: The chip is washed with methanol for 5 mins followed by washing with TBS Buffer for 5 mins. Primary antibody containing PBST+1% BSA+Anti-p53 Antibody is incubation is done on the chip at 37 C for 1 hr. The chip is washed with PBST for 5 mins thrice. This is followed by secondary antibody incubation at 37 C for 1 hr. Secondary antibody contains PBST+1% BSA+Goat Anti-mouse IgG. The chip is washed with PBST for 5 mins thrice. This is followed by DI water washing for 5 mins twice. The chips are dried and scanned under a 488 nm laser scanner.

pH detection: The chip is washed with methanol for 5 mins followed by washing with TBS Buffer for 5 mins. Primary antibody containing PBST+1% BSA+Anti-p53 Antibody photoactive molecule (PBG1-p53) is incubation is done on the chip at 37 C for 1 hr. The chip is washed with PBST for 5 mins thrice. This is followed by DI water washing for 5 mins twice. The chips were dried and exposed using 365 nm bulb strata-linker for 15 minutes and mixed with 30 ul of DI water and the pH of the solution was read using an ISFET pH sensor (Sentron).

The results are shown in Table 6 below:

TABLE 6

Results of ionic vs. fluorescent detection of antibody binding

| | | Detection Method: Fluorescence | | | | Detection Method: Fluorescence | |
|---|---|---|---|---|---|---|---|
| ID | p53 Antibody | Signal | Detected | ID | p53 Antibody | pH | Detected |
| On Natural sequence synthesized | | | | | | | |
| S1 | 1 ng/ml | 65535 | Y | S1 | 1 ng/ml | 12.3 | Y |
| S2 | 100 pg/ml | 12478 | Y | S2 | 100 pg/ml | 11.2 | Y |
| S3 | 10 pg/ml | 2645 | Y | S3 | 10 pg/ml | 9.9 | Y |
| S4 | 1 pg/ml | 856 | N | S4 | 1 pg/ml | 8.4 | Y |
| S5 | 0 pg/ml | 800 | N | S5 | 0 pg/ml | 7.23 | N |
| On Mutant sequence synthesized | | | | | | | |
| S1 | 1 ng/ml | 756 | N | S1 | 1 ng/ml | 7.31 | N |
| S2 | 100 pg/ml | 745 | N | S2 | 100 pg/ml | 7.38 | N |
| S3 | 10 pg/ml | 700 | N | S3 | 10 pg/ml | 7.47 | N |

TABLE 6-continued

Results of ionic vs. fluorescent detection of antibody binding

| | | Detection Method: Fluorescence | | | | Detection Method: Fluorescence | |
|---|---|---|---|---|---|---|---|
| ID | p53 Antibody | Signal | Detected | ID | p53 Antibody | pH | Detected |
| S4 | 1 pg/ml | 536 | N | S4 | 1 pg/ml | 7.45 | N |
| S5 | 0 pg/ml | 275 | N | S5 | 0 pg/ml | 7.38 | N |

The results indicate that the photoactive molecules concept can be incorporated into protein/antibody detection and has a higher sensitivity of <1 pg/ml compared to 10 pg/ml (for fluorescence detection). This may be attributed to that the fact the fluorescence detection includes excitation which leads to higher noise compared to pH sensing. The pH sensing model can be utilized for protein and antibody detection assays.

Example 17: Sequencing

Photoactive sequencing molecules PM 9 (NPPOC-3'-dCTP-PAG1), PM10 (NPPOC-3'-dATP-PAG2), PM11 (NPPOC-3'-dUTP-PBG1) and PM 12 (NPPOC-3'-dGTP-PBG2) are synthesized as given in Examples 5, 6, 7 and 8 by replacing the dNTP's with 3'-NPPOC blocked nucleotides. The NPPOC blocking protects the nucleotide extension until the group is removed (i.e., is a removable blocker). Photoactive sequencing molecules PM9-PM12 are tested for their performance of sequencing on the methylenetetrahydrofolate reductase (MTHFR) gene.

A PNA-DNA chimera sequence 5'-ATGCACCGA-CATGGGC-3' (SEQ ID NO: 18) is synthesized on a Silicon wafer with ISFET wells according to the methods previously described. Genomic DNA samples are obtained in-house from the Vibrant Genomics Labs and sequenced using a commercial synthesizer to determine the sequence of the region of interest. The sequence to be synthesized is 5'-ATGCACCGACATGGGC ATCACTTG-3' (SEQ ID NO: 19), with the sequencing by synthesis component in bold.

A standard PCR reaction using forward and reverse primers is performed on the extracted DNA samples to amplify the MTHFR gene. Hybridization of the amplification product to the PNA-DNA probes and polymerase extension for sequencing by synthesis is performed. The PCR product is mixed in 1×DNA Polymerase Buffer (Clontech), 20 nmol of $MgCl_2$, 1 unit Titanium Taq DNA Polymerase (Clontech), and all 4 photoactive molecules (PM9, PM10, PM11, PM12) (each 20 pmoles).

Hybridization is done in a hybridization chamber at 55° C. for 30 minutes followed by washing the chips in 0.1× Ssarc buffer 40° C. for 5 minutes twice followed by rinsing in DI Water.

The chips are then exposed using 365 nm bulb strata-linker for 15 minutes and mixed with 30 µl of DI water. The pH of the solution is read using an ISFET pH sensor (Sentron).

The exposure to 365 nm light also simultaneously unblocks the NPPOC protection on the 3' end to enable continuation of the polymerization reaction and sequencing by synthesis. This hybridization and extension cycle are repeated multiple times to generate and detect the sequence of the region of interest. The results anticipated are shown in Table 7:

TABLE 7

Expected results of sequencing

| Cycle | pH Reading | PM Call | Detected nucleotide |
|---|---|---|---|
| Cycle 1 | 3.84 | PM10 | A |
| Cycle 2 | 11.2 | PM11 | T |
| Cycle 3 | 2.68 | PM9 | C |
| Cycle 4 | 3.98 | PM10 | A |
| Cycle 5 | 2.66 | PM9 | C |
| Cycle 6 | 11.02 | PM11 | T |
| Cycle 7 | 11.1 | PM11 | T |
| Cycle 8 | 10.15 | PM12 | G |

As shown, the detected nucleotide sequence will be 5'-ATCACTTG-3' (SEQ ID NO: 20), corresponding with the amplification product from the MTHFR amplicon sequence 5'-CAAGTGAT-3' (SEQ ID NO: 21)

Thus, the photoactive sequencing molecules described herein can be utilized to determine the sequence of a polynucleotide using reversible terminator and a photoactive compound attached to the mononucleotides.

OTHER EMBODIMENTS

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A polynucleotide comprising a nucleotide bound to a photoactive group, wherein said photoactive group comprises a photoacid generator or a photobase generator.

2. The polynucleotide of claim 1, wherein said photobase generator produces an organic compound having a pKA of 9 or higher, 10 or higher, 11 or higher, 12 or higher, 13 or higher, or 14 or higher upon exposure to an activating radiation.

3. The polynucleotide of claim 1, wherein said photoacid generator produces an organic compound having a pKA of 5 or lower, 4 or lower, 3 or lower, 2 or lower, or 1 or lower upon exposure to an activating radiation.

4. The polynucleotide of claim 1, wherein said photoacid generator is selected from the group consisting of: an o-acyloxime, a benzoyloxycarbonyl derivative, a photoactive carbamates, an oxime ester compounds, an ammonium compound, a benzoin compound, a dimethoxybenzyl urethane compound, an orthonitrobenzyl urethane compound, an aromatic sulfonamide, an alpha-lactams, and an N-(2-arylethenyl) amide.

5. The polynucleotide of claim 1, wherein said photobase generator is selected from the group consisting of: a 2-hydroxy-2-phenylacetophenone N-cyclohexyl carbamate, an o-nitrobenzyl N-cyclohexyl carbamate, an N-cyclohexyl-2-naphthalene sulfonamide, a 3,5-dimethoxybenzyl N-cyclohexyl carbamate, an N-cyclohexyl p-toluene sulfonamide; and a dibenzoin isophorone dicarbamate.

6. The polynucleotide of claim 1, wherein said photoactive group is photocleavable.

7. The polynucleotide of claim 6, wherein said photoactive group is cleaved via homolytic cleavage.

8. The polynucleotide of claim 1, wherein said photoactive group initiates a downstream reaction upon exposure to an activating radiation.

9. The polynucleotide of claim 1, wherein said photoactive group comprises an ionic organic salt.

10. The polynucleotide of claim 1, wherein said photoactive group comprises an onium salt.

11. The polynucleotide of claim 1, wherein said photoactive group is bound to a nucleobase of said nucleotide.

12. The polynucleotide of claim 1, wherein said photoactive group is bound to a 2' or 5' carbon of said nucleotide.

13. The polynucleotide of claim 1, wherein said nucleotide is bound to a removable blocking group.

14. The polynucleotide of claim 13, wherein said removable blocking group is a reversible terminator.

15. A polynucleotide comprising a nucleotide bound to a photoactive group, wherein said nucleotide is according to Formula I:

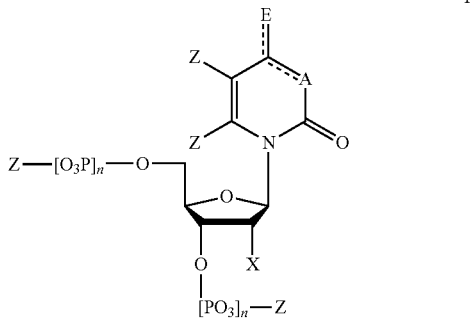

wherein n is from 0-3;

X is selected from the group consisting of: H, OPg, and a photoactive group, where Pg is a protecting group;

A is NH when

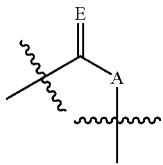

and A is N when

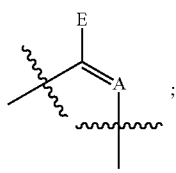

E is O when

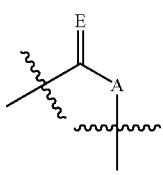

and E is NHZ when

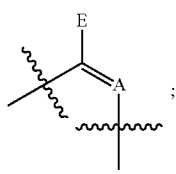

and each Z is independently selected from the group consisting of: H, Me, and a photoactive group; and
wherein at least one of said Z or X is said photoactive group.

16. A polynucleotide comprising a nucleotide bound to a photoactive group, wherein said nucleotide is according to Formula II:

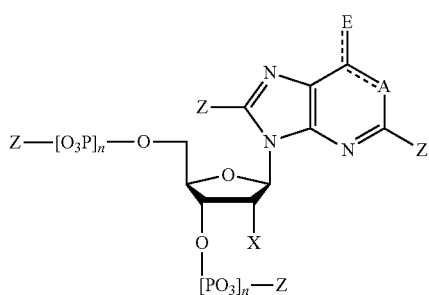

wherein
n is from 0-3;
X is selected from the group consisting of: H, OPg, and a photoactive group, where Pg is a protecting group;
A is NH when

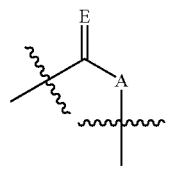

and A is N when

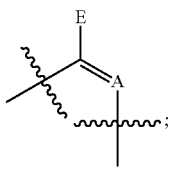

E is O when

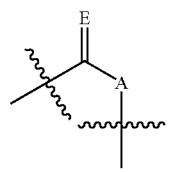

and E is NHZ when

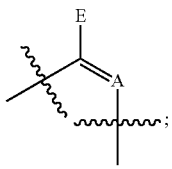

and
each Z is independently selected from the group consisting of: H, Me, and a photoactive group; and
wherein at least one of said Z or X is said photoactive group.

17. A polynucleotide comprising a nucleotide bound to a photoactive group, wherein said nucleotide is selected from the group consisting of:

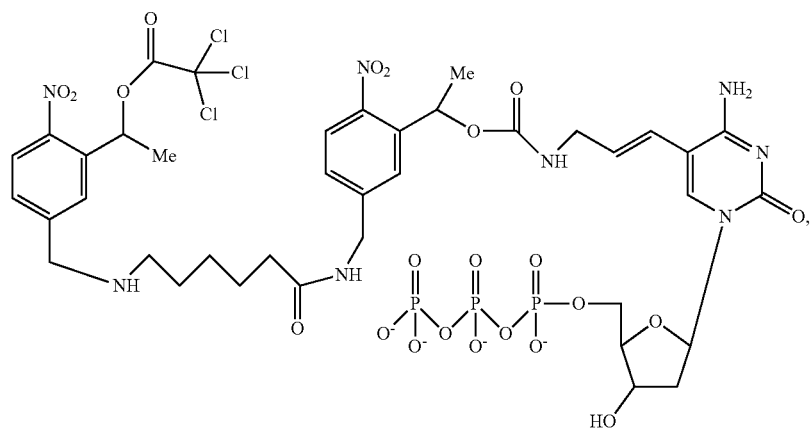
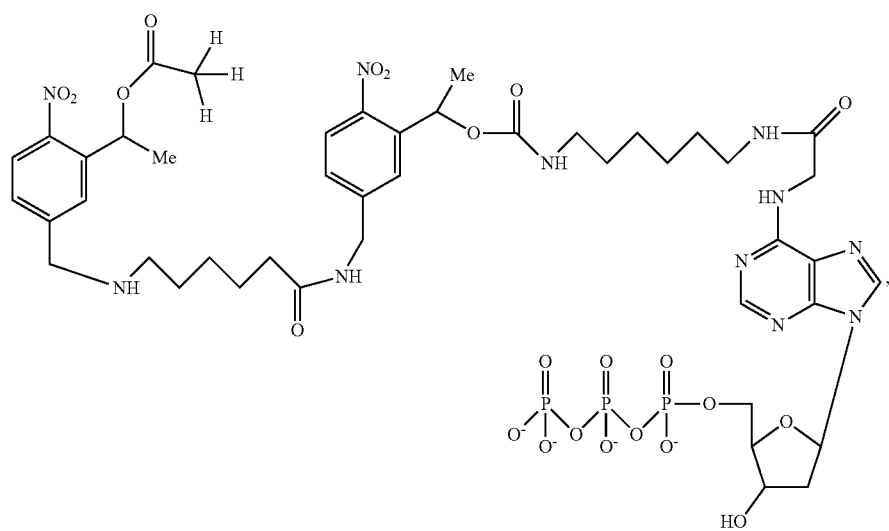
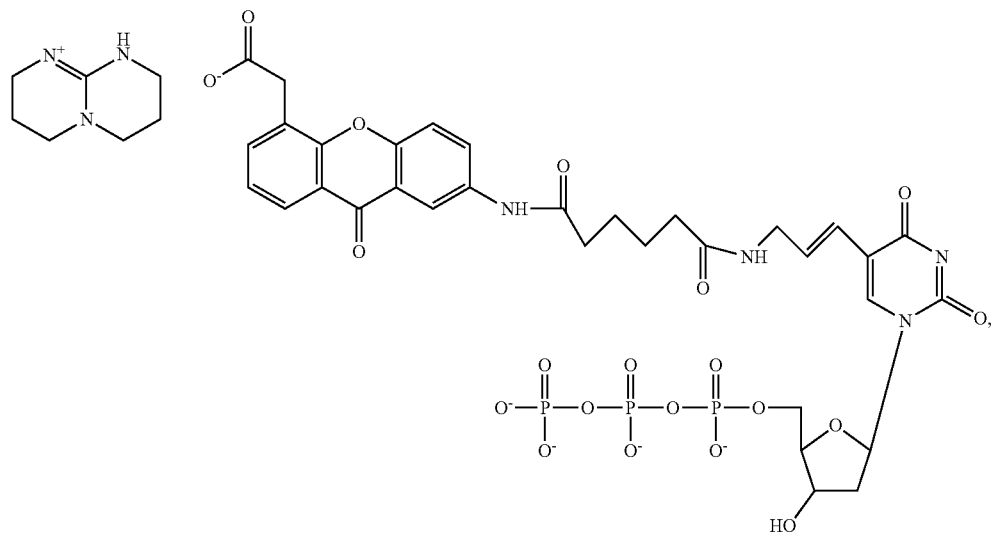

-continued
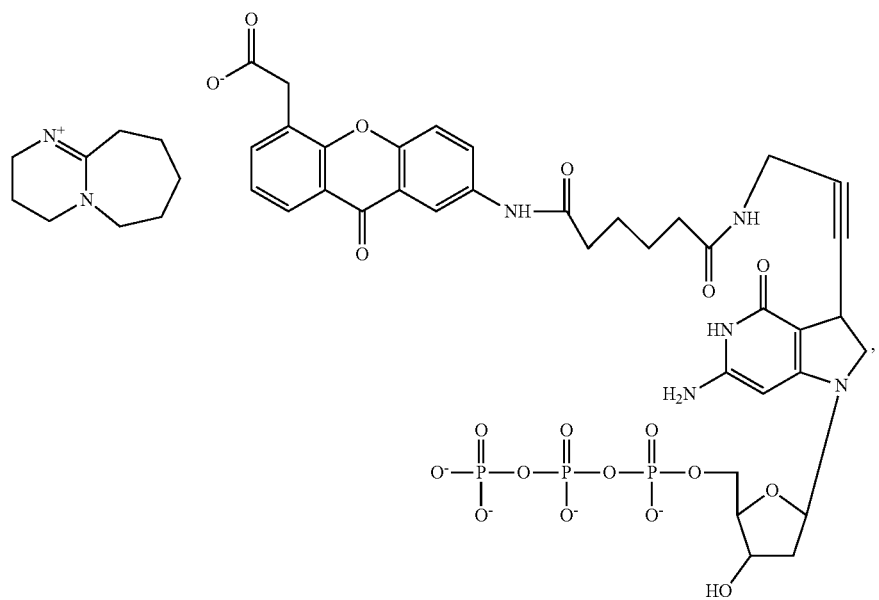
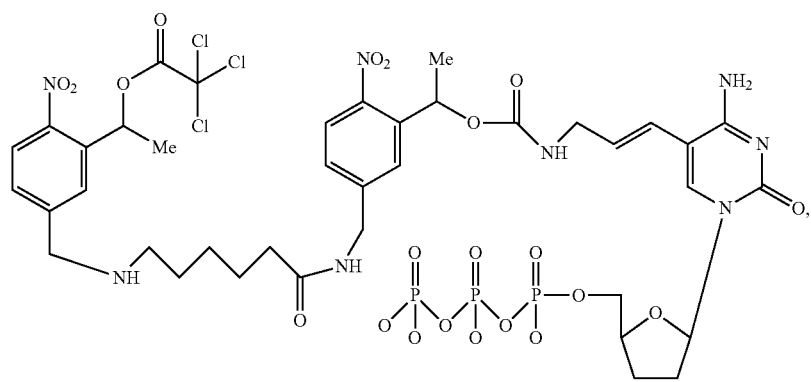
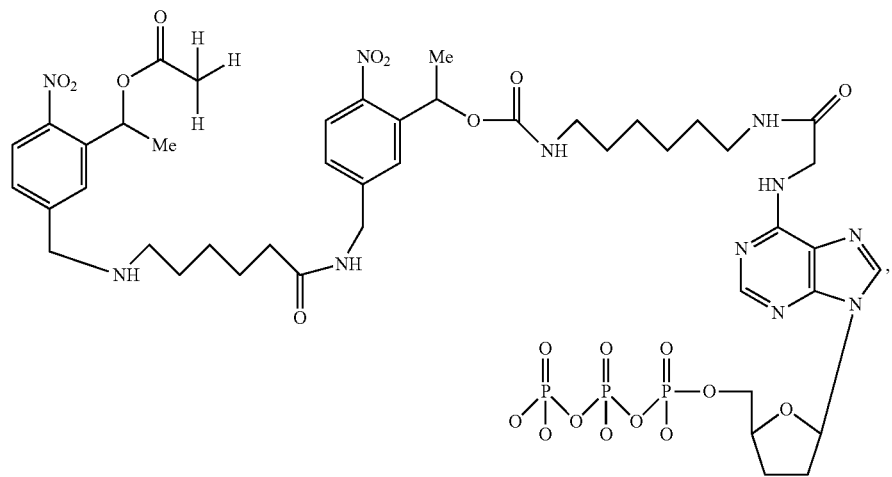

-continued

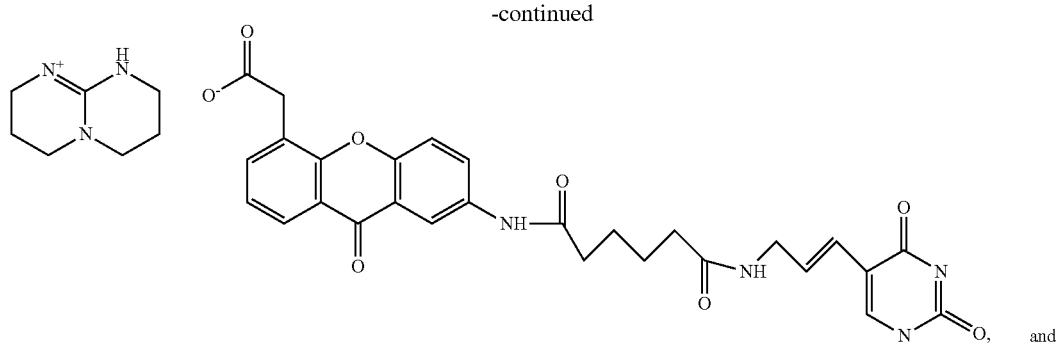

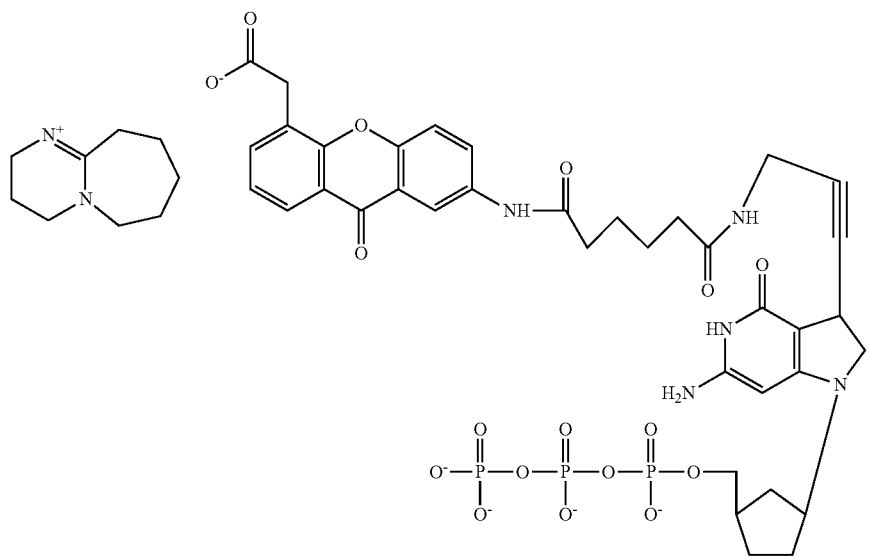

18. The polynucleotide of claim 17, wherein said modified nucleotide is bound to a removable blocking group.

19. The polynucleotide of claim 18, wherein said removable blocking group is a reversible terminator.

20. A polynucleotide comprising a nucleotide bound to a photoactive group, wherein said photoactive group comprises an ionic organic salt.

21. A polynucleotide comprising a nucleotide bound to a photoactive group, wherein said photoactive group comprises an onium salt.

22. A polynucleotide comprising a nucleotide bound to a photoactive group, wherein said photoactive group is bound to a 2' or 5' carbon of said polynucleotide or said single nucleotide.

23. An array comprising a plurality of polynucleotides immobilized to the surface of the array, wherein at least one polynucleotide comprises a nucleotide bound to a photoactive group.

24. The array of claim 23, wherein said photoactive group comprises a photoacid generator or a photobase generator.

25. The array of claim 23, wherein said nucleotide is according to Formula I:

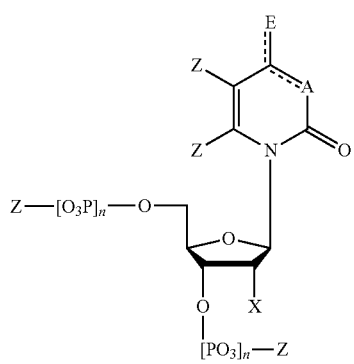

wherein n is from 0-3;

X is selected from the group consisting of: H, OPg, and a photoactive group, where Pg is a protecting group;

A is NH when

[structure]

and A is N when

[structure];

E is O when

[structure]

and E is NHZ when

[structure];

and
  each Z is independently selected from the group consisting of: H, Me, and a photoactive group; and
  wherein at least one of said Z or X is said photoactive group.

26. The array of claim 23, wherein said nucleotide is according to Formula II:

[structure II]

wherein
  n is from 0-3;
  X is selected from the group consisting of: H, OPg, and a photoactive group, where Pg is a protecting group;
  A is NH when

[structure]

and A is N when

[structure];

E is O when

[structure]

and E is NHZ when

[structure];

and
  each Z is independently selected from the group consisting of: H, Me, and a photoactive group; and
  wherein at least one of said Z or X is said photoactive group.

27. The array of claim 23, wherein said nucleotide is selected from the group consisting of:

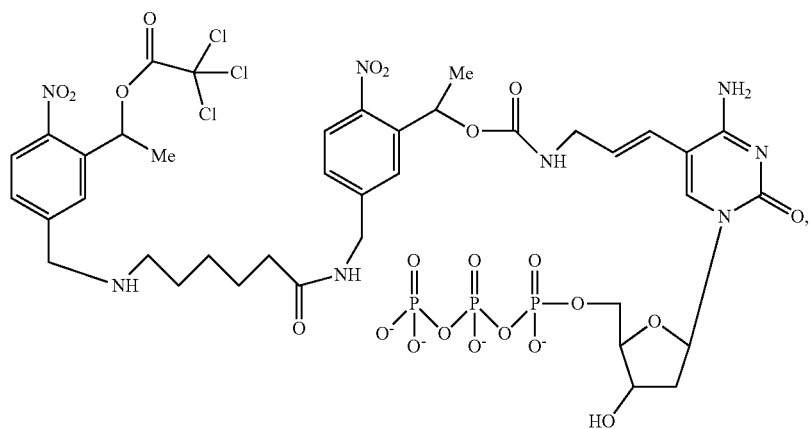
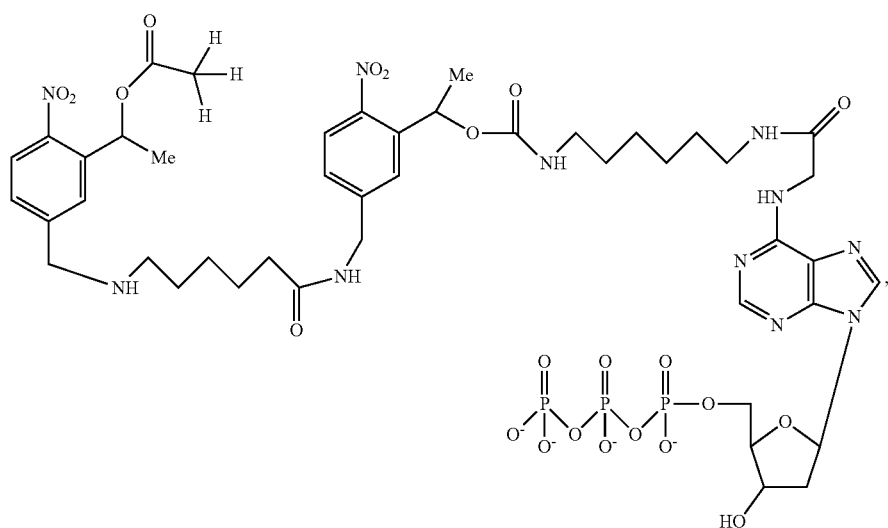
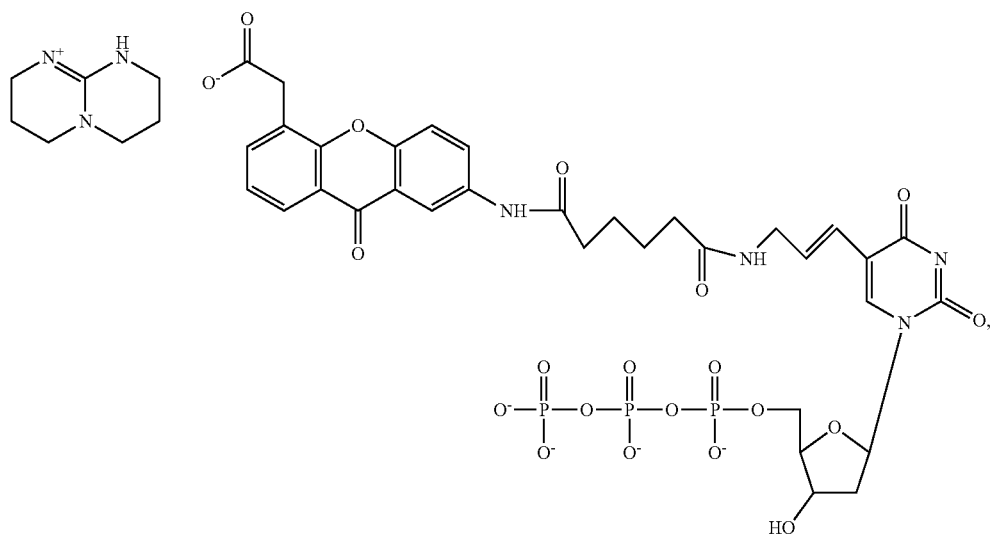

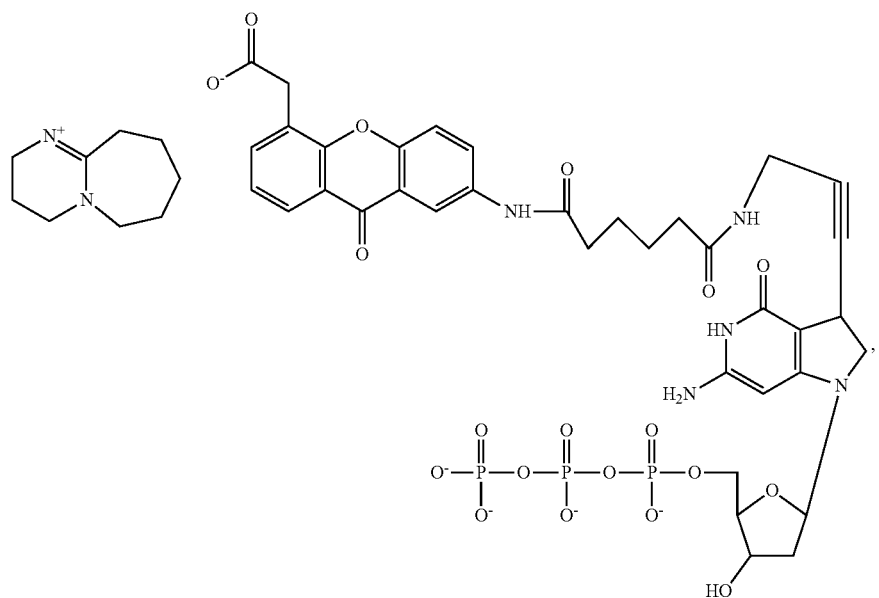
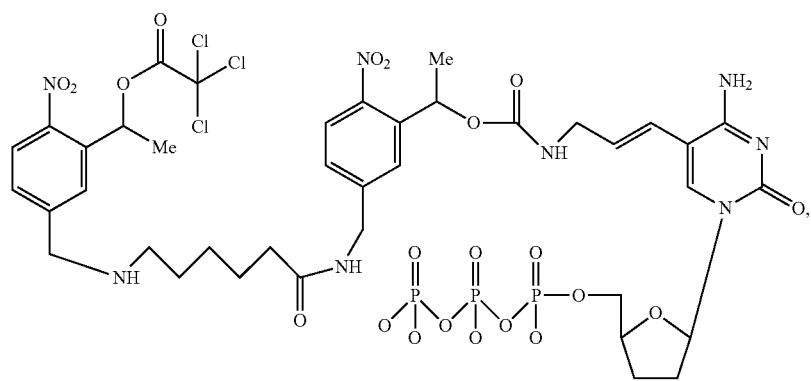
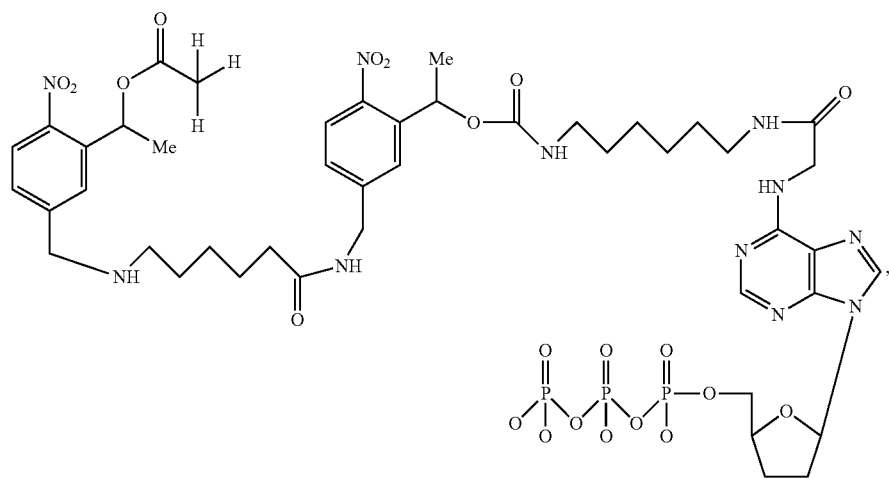

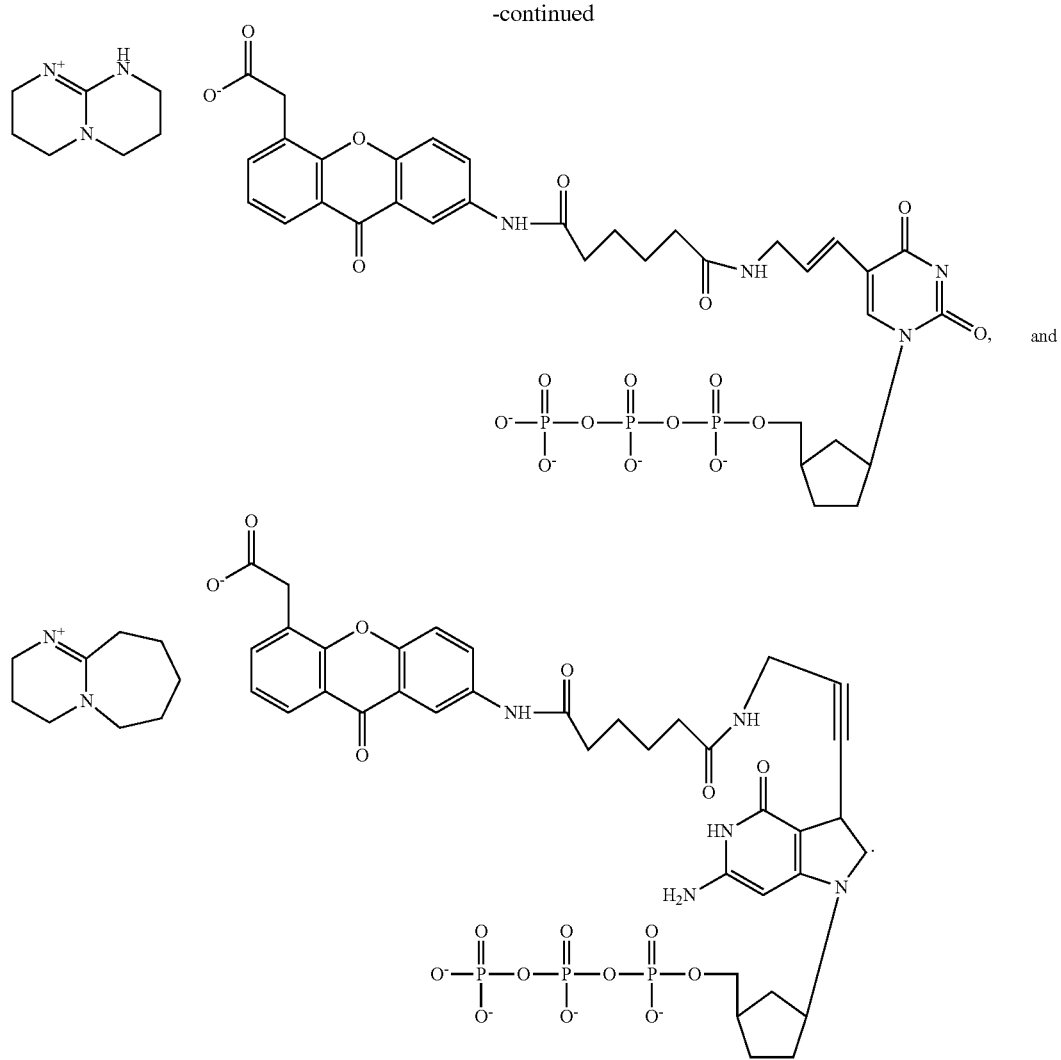
28. The array of claim 27, wherein said modified nucleotide is bound to a removable blocking group.
29. The array of claim 28, wherein said removable blocking group is a reversible terminator.
* * * * *